US012043835B2

(12) United States Patent
Gao et al.

(10) Patent No.: US 12,043,835 B2
(45) Date of Patent: Jul. 23, 2024

(54) METHOD FOR MAKING SITE-DIRECTED MODIFICATION TO PLANT GENOMES BY USING NON-INHERITABLE MATERIALS

(71) Applicant: INSTITUTE OF GENETICS AND DEVELOPMENTAL BIOLOGY, CHINESE ACADEMY OF SCIENCES, Beijing (CN)

(72) Inventors: Caixia Gao, Beijing (CN); Zhen Liang, Beijing (CN); Yanpeng Wang, Beijing (CN); Qiwei Shan, Beijing (CN); Qianna Song, Beijing (CN)

(73) Assignee: INSTITUTE OF GENETICS AND DEVELOPMENTAL BIOLOGY, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 15/558,794

(22) PCT Filed: Mar. 14, 2016

(86) PCT No.: PCT/CN2016/076244
§ 371 (c)(1),
(2) Date: Sep. 15, 2017

(87) PCT Pub. No.: WO2016/155482
PCT Pub. Date: Oct. 6, 2016

(65) Prior Publication Data
US 2018/0163232 A1    Jun. 14, 2018

(30) Foreign Application Priority Data

Mar. 16, 2015  (CN) .......................... 201510114017.4

(51) Int. Cl.
*C12N 15/82* (2006.01)
*C12N 9/22* (2006.01)
*C12N 9/96* (2006.01)
*C12N 15/01* (2006.01)
*C12N 15/11* (2006.01)
*C12N 15/87* (2006.01)
*C12N 15/90* (2006.01)

(52) U.S. Cl.
CPC ........... *C12N 15/8213* (2013.01); *C12N 9/22* (2013.01); *C12N 9/96* (2013.01); *C12N 15/01* (2013.01); *C12N 15/11* (2013.01); *C12N 15/8207* (2013.01); *C12N 15/87* (2013.01); *C12N 15/902* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 5,500,360 A | 3/1996 | Ahlquist et al. |
| 5,736,369 A | 4/1998 | Bowen et al. |
| 5,910,631 A | 6/1999 | Topfer et al. |
| 6,583,335 B1 | 6/2003 | Peffley et al. |
| 6,603,061 B1 | 8/2003 | Armstrong et al. |
| 6,846,970 B1 * | 1/2005 | Christou ............ C12N 15/8201 435/470 |
| 7,799,566 B2 | 9/2010 | Lowe et al. |
| 8,697,359 B1 | 4/2014 | Zhang |
| 9,719,108 B2 | 8/2017 | Samuel et al. |
| 2003/0135891 A1 | 7/2003 | Gould et al. |
| 2011/0189775 A1 | 8/2011 | Ainley et al. |
| 2012/0090053 A1* | 4/2012 | Yoshikawa .............. A01H 3/00 800/298 |
| 2013/0145488 A1* | 6/2013 | Wang ................... C12N 15/895 800/21 |
| 2013/0263324 A1 | 10/2013 | Lassner et al. |

(Continued)

FOREIGN PATENT DOCUMENTS

| CN | 102812034 A | 12/2012 |
| CN | 103343120 A | 10/2013 |

(Continued)

OTHER PUBLICATIONS

Gasiunas et al. Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012). (Year: 2012).*

Yoo et al. Arabidopsis mesophyll protoplasts: a versatile cell system for transient gene expression analysis. Nat Protoc. 2007;2(7):1565-72. (Year: 2007).*

Jiang et al. Demonstration of CRISPR/Cas9/sgRNA-mediated targeted gene modification in *Arabidopsis*, tobacco, sorghum and rice. Nucleic Acids Res. Nov. 2013;41(20):e188. Epub Sep. 2, 2013. (Year: 2013).*

(Continued)

*Primary Examiner* — Cynthia E Collins
(74) *Attorney, Agent, or Firm* — Troutman Pepper Hamilton Sanders LLP

(57) ABSTRACT

The invention disclosed a method for conducting site-directed modification to a plant genome using non-inheritable materials. The method provided in the present invention specifically comprises the following steps: introducing a non-inheritable material into a cell or a tissue or a part of the plant of interest; wherein said non-inheritable material is a nuclease specific to said target fragment or an mRNA expressing said nuclease, thereby the target fragment is cleaved by said nuclease and site-directed modification to the target fragment is achieved through DNA repairing in the plant. By introducing a non-inheritable material of sequence-specific nuclease, site-directed mutation in a plant gene can be achieved, and no exogenous gene or nucleic acid fragments will be integrated into the plant as obtained. Therefore, the present invention can lead to more precise genome function study and higher biosafety in breeding.

7 Claims, 7 Drawing Sheets
Specification includes a Sequence Listing.

(56) References Cited

U.S. PATENT DOCUMENTS

| | | | |
|---|---|---|---|
| 2014/0096284 A1* | 4/2014 | Martin-Ortigosa | A61K 9/5089 800/293 |
| 2015/0059010 A1 | 2/2015 | Cigan | |
| 2015/0067922 A1* | 3/2015 | Yang | C12N 15/8245 800/298 |
| 2016/0145631 A1* | 5/2016 | Voytas | C12N 15/8206 800/295 |

FOREIGN PATENT DOCUMENTS

| | | | |
|---|---|---|---|
| CN | 103382468 A | 11/2013 | |
| CN | 103667338 A | 3/2014 | |
| CN | 103898099 A | 7/2014 | |
| CN | 103952405 A | 7/2014 | |
| CN | 104212778 A | 12/2014 | |
| CN | 104293828 A | 1/2015 | |
| DE | 10 2015 004 187 A1 | 10/2016 | |
| EP | 2 274 973 A1 | 1/2011 | |
| JP | 2002-526080 A | 8/2002 | |
| JP | 2012-523234 A | 10/2012 | |
| WO | WO 2011/072246 * | 6/2011 | C12N 15/10 |
| WO | 2013/142578 A1 | 9/2013 | |
| WO | 2013/176772 A1 | 11/2013 | |
| WO | 2014/018423 | 1/2014 | |
| WO | 2014039872 A1 | 3/2014 | |
| WO | 2014/065596 A1 | 5/2014 | |
| WO | 2014104878 A1 | 7/2014 | |
| WO | 2014/144155 A1 | 9/2014 | |
| WO | 2014161821 A1 | 10/2014 | |
| WO | 2014/194190 A1 | 12/2014 | |
| WO | 2014199358 A1 | 12/2014 | |
| WO | 2015/026885 | 2/2015 | |
| WO | 2016/021973 A1 | 2/2016 | |

OTHER PUBLICATIONS

Wang et al. One-step generation of mice carrying mutations in multiple genes by CRISPR/Cas-mediated genome engineering. Cell. May 9, 2013;153(4):910-8. Epub May 2, 2013. (Year: 2013).*

Klein et al. (1992) Transformation of microbes, plants and animals by particle bombardment. Biotechnology (NY) 10(3):286-91. (Year: 1992).*

Leduc et al. Gene transfer to inflorescence and flower meristems using ballistic microtrgeting. Sex. Plant Reprod. 1994. 7: 135-143. (Year: 1994).*

Barcelo et al. Transgenic cereal (tritodeum) plants obtained at high efficiency by microprojectile bombardment of inflorescence tissue. The Plant Journal. 1994. 5(4), 583-592. (Year: 1994).*

Wang et al. Cotton transformation via pollen tube pathway. Methods Mol Biol. 2013;958:71-7. (Year: 2013).*

Dudas et al. DNA double-strand break repair by homologous recombination. Mutat. Res. Mar. 2004;566(2):131-67. (Year: 2004).*

Kim et al. A guide to genome engineering with programmable nucleases. Nat. Rev. Genet. May 2014;15(5):321-34. Epub Apr. 2, 2014. (Year: 2014).*

Vainsten et al. Permanent genome modifications in plant cells by transient viral vectors. Trends Biotechnol. Aug. 2011;29(8):363-9. Epub Apr. 30, 2011. (Year: 2011).*

Lee et al. RNA-guided genome editing in *Drosophila* with the purified Cas9 protein. G3 (Bethesda). May 28, 2014;4(7):1291-5. (Year: 2014).*

Bassett et al. Highly efficient targeted mutagenesis of *Drosophila* with the CRISPR/Cas9 system. Cell Rep. Jul. 11, 2013;4(1):220-8. Epub Jul. 1, 2013. (Year: 2013).*

Martin-Ortigosa et al. Mesoporous silica nanoparticle-mediated intracellular cre protein delivery for maize genome editing via loxP site excision. Plant Physiol. Feb. 2014;164(2):537-47. Epub Dec. 27, 2013. (Year: 2013).*

Kim et al. Highly efficient RNA-guided genome editing in human cells via delivery of purified Cas9 ribonucleoproteins. Genome Res. Jun. 2014;24(6):1012-9. Epub Apr. 2, 2014. (Year: 2014).*

Fernando et al. Transient gene expression in pine pollen tubes following particle bombardment. Plant Cell Reports. (2000) 19:224-228. (Year: 2000).*

Vasil et al. Transformation of wheat via particle bombardment. Methods Mol. Biol. 2006;318:273-83. (Year: 2006).*

Beckert et al. Synthesis of RNA by in vitro transcription. Methods Mol. Biol. 2011;703:29-41. (Year: 2011).*

Yang et al. Particle-Mediated Gene Delivery In Vivo and In Vitro. Current Protocols in Human Genetics (1997) 12.6.1-12.6.14 John Wiley & Sons Inc. (Year: 1997).*

Bassett et al. CRISPR/Cas9 mediated genome engineering in *Drosophila*. Methods. Sep. 2014;69(2):128-36. Epub Feb. 24, 2014. (Year: 2014).*

Curtin, S.C. et al., "Targeted Mutagenesis of Duplicated Genes in Soybean with Zinc Finger Nucleases", Plant Physiology (Jun. 2011), vol. 156, No. 2, pp. 466-473.

Fang, Rui et al., "New Method of Genome Editing Derived from CRISPR/Cas9", Progress in Biochemistry and Biophysics (Aug. 2013), vol. 40, No. 8, pp. 691-702 and English Abstract Thereof.

International Search Report and Written Opinion Issued in PCT/CN2016/076244, dated Jun. 15, 2016 and English Translation thereof, 10 pages.

Liang, Zhen et al., "Targeted Mutagenesis in Zea Mays Using TALENs and the CRISPR/Cas System", Journal of Genetics and Genomics (Nov. 2013), vol. 41, No. 2, pp. 63-68.

Xiao, An et al., "Progress in Zinc Finger Nuclease Engineering for Targeted Genome Modification", HEREDITAS (Jul. 2011), vol. 33, No. 7, pp. 665-683 and English Abstract Thereof.

Zhang, Jinmai et al., "TALENs: A New Genome Site-Specific Modification Technology", Chinese Bulletin of Life Sciences (Jan. 2013), vol. 25, No. 1, pp. 126-132 and English Abstract Thereof.

Armstrong, et al., "Development and availability of germplasm with high Type II culture formation response", https://mnl.maizegdb.org/mn1/65/146armstrong.html. 3 pages.

Jinek, et al., "A Programmable Dual-RNA-Guided DNA Endonuclease in Adaptive Bacterial Immunity", Science (Aug. 2012) vol. 337, pp. 816-821.

Wang, et al., "Simultaneous editing of three homoeoalleles in hexaploid bread wheat confers heritable resistance to powdery mildew" Nature Biotechnology (Sep. 2014) vol. 32, No. 9, pp. 947-952.

Feng Z et al., "Efficient genome editing in plants using a CRISPR/Cas system," Cell Research, vol. 23, pp. 1229-1232, Aug. 2013.

Woo J.W., et al., "DNA-free genome editing in plants with preassembled CRISPR-Cas9 ribonucleoproteins," Nature Biotechnology, vol. 33, No. 11, pp. 1162-1165, Nov. 2015.

Nathalia Maira Cabral de Medeiros et al., "Recent Advances In Plant DNA Repair", INTECH, 2015, pp. 3-42 (available at http://dx.doi.org/10.5772/59998).

Kaoru Okamoto Yoshiyama, "SOG1: a master regulator of the DNA damage response in plants", Advance Publication by J-Stage, Genes & Genetic Systems, Nov. 26, 2015, pp. 1-34.

Liang et al., "Efficient DNA-free genome editing of bread wheat using CRISPR/Cas9 ribonucleoprotein complexes", Nature Communications, Jan. 18, 2017, 15 pages.

Svitashev et al., "Genome editing in maize directed by CRISPR-Cas9 ribonucleoprotein complexes", Nature Communications, Nov. 16, 2016, 7 pages,.

Zhang et al., "Efficient and transgene-free genome editing in wheat through transient expression of CRISPR/Cas9 DNA or RNA", Nature Communications, Aug. 25, 2016, 7 pages.

Weeks et al., "Rapid production of multiple independent lines of fertile transgenic wheat (*Triticum aestivum*)", Plant Physiol., 1993, vol. 102, pp. 1077-1084.

Chang et al., "Genome editing with RNA-guided Cas9 nuclease in Zebrafish embryos", Cell Research, 2013, vol. 23, pp. 465-472.

Shan et al., "Rapid and Efficient Gene Modification in Rice and Brachypodium Using TALENs", Molecular Plant, 2013, vol. 6, No. 4, pp. 1365-1368.

Song et al., "Application of a transformation method via the pollen-tube pathway in agriculture molecular breeeding", Life Science Journal, 2007, vol. 4, No. 1, pp. 77-79.

(56) References Cited

OTHER PUBLICATIONS

Zahir et al., "The Efficient Virus-Mediated Genome Editing in Plants Using the CRISPR/Cas9 System", Molecular Plant, vol. 8, No. 8, 2015, pp. 1288-1291.
Anonymous: "A Streamlined Method for the Production, Screening, and Application of sgRNAs for CRISPR/Cas9 Gene Editing" Bio Techniques, vol. 57, No. 3, Sep. 2014, p. 157.
Barrangou et al., "CRISPR provides acquired resistance against viruses in prokaryotes", Science, 2007, vol. 315, 1709-1712.
Zetsche et al., "Cpf1 is a single RNA-guided endonuclease of a Class 2 CRISPR-Cas system", Cell, vol. 163, No. 3, 2015, pp. 759-771.
Clough et al., "Floral Dip: a simplified method for Agrobacterium-mediated transformation of *Arabidopsis thaliana*", The Plant Journal, vol. 16, No. 6, 1998, pp. 735-743.
Deltcheva et al., "CRISPR RNA maturation by trans-encoded small RNA and host factor RNase III", Nature, 2011, vol. 471, No. 7340, pp. 602-607.
Gelvin, "Viral-mediated plant transformation gets a boost", Nature Biotechnology, vol. 23, No. 6, 2005, pp. 684-685.
Guilinger et al., "Fusion of catalytically Inactive Cas9 to FokI nuclease improves the specificity of genome modification", Nat Biotechnol., 2014, vol. 32, No. 6, pp. 577-582.
Helenius et al., "Gene delivery into intact plants using the Helios Gene Gun", Plant Molecular Biology Reporter, 2000, vol. 18, No. 3, pp. 287a-287l.
Xing et al., "A CRISPR/Cas9 toolkit for multiplex genome editing in plants", BMC Plant Biology, vol. 14, Article No. 327, 2014, pp. 1-12.
International Search Report and Written Opinion issued by international searching authority in International Application No. PCT/EP2016/061237, dated Feb. 20, 2017.
Jansen et al., "Identification of genes that are associated with DNA repeats in pokaryotes", Molecular Microbiology, 2002, vol. 43, No. 6, pp. 1565-1575.
Krens et al., "Transformation and regeneration in sugar beet (*Beta vulgaris* L.) induced by 'shooter' mutants of Agrobacterium tumefaciens", Euphytica, 1988, vol. 39, No. 3, pp. 185-194.
Bortesi et al., "The CRISPR/Cas9 system for plant genome editing and beyond", Biotechnology Advances, vol. 33, No. 1, Dec. 20, 2014, pp. 41-52.
Mahn et al., "Transient gene expression in shoot apical meristems of sugarbeet seedlings after particle bombardment", Journal of Experimental Botany, 1995, vol. 46, No. 291, pp. 1625-1628.
Makarova et al., "An updated evolutionary classification of CRISPR-Cas systems", Nature Rev. Microbiol., 2015, vol. 13, No. 11, pp. 722-736.
Makarova et al., "Annotation and Classification of CRISPR-Cas Systems", Methods Mol. Biol., 2015, vol. 1311, pp. 47-75.
Makarova et al., "Unification of Cas protein families and a simple scenario for the origin and evolution of CRISPR-Cas systems", Biology Direct, vol. 6, No. 38, 2011, 27 pages.
Mali et al., "CAS9 transcriptional activators for target specificity screening and paired nickases for cooperative genome engineering", Nat Biotechnol., 2013, vol. 31, No. 9, pp. 833-838.
Martin-Ortigosa et al., "Proteolistics: a biolistic method for intracellular delivery of proteins", Transgenic Research, 2014, vol. 23, pp. 743-756.
Baltes et al., "DNA Replicons for Plant Genome Engineering" The Plant Cell, American Society of Plant Biologist, vol. 26, No. 1, Jan. 17, 2014, pp. 151-163.
Quinn et al., "A Streamlined Method for the Production, Screening, Application of sgRNAs for CRISPR/Cas Gene Editing", Molecular Therapy, vol. 22, Supplement 1, 2014, 2 pages.
Ramakrishna et al., "Gene disruption by cell-penetrating peptide-mediated delivery of Cas9 protein and guide RNA", Genome Research, 2014, vol. 24, No. 6, pp. 1020-1027.
Sapranauskas et al., "The *Streptococcus* thermophilus CRISPR/Cas system provides immunity in *Escherichia coli*", Nucleic Acids Research, 2011, vol. 39, No. 21, pp. 9275-9282.

Maruyama et al., "Inhibition of non-homologous end joining increases the efficiency of CRISPR/Cas9-mediated precise [TM: inserted] genome editing", Nat Biotechnol, vol. 33, No. 5, May 2015, pp. 538-542.
Jacobs et al., "Targeted genome modifications in soybean with CRISPR/Cas9", BMC Biotechnology, vol. 15, No. 16, 2015, pp. 1-10.
Van der Oost et al., "Unravelling the structural and mechanistic basis of CRISPR-Cas systems", Nat Rev Microbiol., 2014, vol. 12, No. 7, pp. 479-492.
Wiedenheft et al., "Structures of the RNA-guided surveillance complex from a bacterial immune system", Nature, 2011, vol. 477, No. 7365, pp. 486-489.
Hyun et al. "Site-directed mutagenesis in *Arabidopsis thaliana* using dividing tissue-targeted RGEN of the CRISPR/Cas System to generate heritable null alleles". Planta, vol. 241, No. 1, Oct. 1, 2014, pp. 271-284.
Zhang et al., "The CRISPR/Cas9 System Produces Specific and Homozygous Targeted Gene Editing in Rice in One Generation," Plant Biotechnology Journal, 2014, vol. 12, No. 6, pp. 797-807.
International Search Report and Written Opinion issued by the International Searching Authority in International Application No. PCT/EP2016/061338, dated Aug. 5, 2016.
Abhishek et al., "Tissue Culture Independent Agrobacterium tumefaciens Mediated In Planta Transformation Method for Tropical Maize (*Zea mays.* L)", Proceedings of the National Academy of Sciences, India, Section B, Biological Sciences, 2016, vol. 86, No. 2, pp. 375-384.
Bent et al., "*Arabidopsis* in Planta Transformation. Uses, mechanisms, and Prospects for Transformation of Other Species", Plant Physiology, 2000, vol. 124, No. 4, p. 1540-1547.
Chowrira et al., "Transgenic Grain Legumes Obtained by In Planta Electroporation-Mediated Gene Transfer", Molecular Biotechnology, vol. 5, No. 2, 1996, pp. 85-96.
Razzaq et al., "Development of in planta transformation protocol for wheat", African Journal of Biotechnology, vol. 10, No. 5, 2011, pp. 740-750.
Collins et al., "The Effect of Cotyledon Excision on Reproductive Development in Pea (*Pisum sativum* L.)", Annals of Botany, vol. 38, No. 1, 1974, pp. 181-188.
Springer et al., "A Histological Examination of Tissue Culture Initiation From Immature Embryos of Maize",Protoplasma, 1979, vol. 101, pp. 269-281.
Ma et al., "Plant multiple genome editing vector pYLCRISPR/Cas9P35s-B, complete sequence", GenBank KR 029113, 2015.
European Search Report issued in EP 15202060 dated Aug. 5, 2016.
Hu et al., "Agrobacterium-mediated vacuum infiltration and floral dip transformation of rapid-cycling *Brassica* rapa", BMC Plant Biology, 2019, vol. 19, Article No. 246, 9 pages.
Ghedira et al., "The Efficiency of *Arabidopsis thaliana* Floral Dip Transformation is Determined Not Only by the Agrobacterium Strain Used but Also by the Physiology and the Ecotype of the Dipped Plant", MPMI, vol. 26, No. 7, 2013, pp. 823-832.
Takacs et al., "Ontogeny of the Maize Shoot Apical Meristem", The Plant Cell, vol. 24, Aug. 2012, pp. 3219-3234.
Al-Abed et al. "Split-seed: a new tool for maize researchers", Planta, 2006, vol. 223, pp. 1355-1360.
Elhiti et al., "The use of zygotic embryos as explants for in vitro propagation: an overview", Plant Embryo Culture:Methods and Protocols, Thrope et al. Eds., Methods in Molecular Biology, 2011, vol. 710, pp. 229-255.
Luo et al., "Non-transgenic Plant Genome Editing Using Purified Sequence-Specific Nucleases", Molecular Plant, 2015, No. 8, pp. 1425-1427.
Liang et al., "Genome editing of bread wheat using biolistic delivery of CRISPR/Cas9 in vitro transcripts or ribonucleoproteins", Nature Protocols, 2018, vol. 13, No. 3, pp. 413-430.
Murashige et al., "A Revised Medium for Rapid Growth and Bio Assays with Tobacco Tissue Cultures", Physiologia Plantarum, 1962, vol. 15, p. 473-497.
Dong et al., "Natural variation of TaGASR7-A1 affects grain length in common wheat under multiple cultivation conditions", Mol Breeding, 2014, vol. 34, pp. 937-947.

(56) References Cited

OTHER PUBLICATIONS

Mali et al., "RNA-Guided Human Genome Engineering via Cas9", Science, 2013, vol. 339, No. 6121, pp. 823-826.
Hwang et al., "Efficient In Vivo Genome Editing Using RNA-Guided Nucleases", Nature Biotechnology, 2013, vol. 31, No. 3, pp. 227-229.
Bin Shen et al., "Generation of gene-modified mice via Cas9/RNA-mediated gene targeting", Cell Research, 2013, vol. 23, p. 720-723.

* cited by examiner

```
(SEQ ID NO: 50)  TaGW2-A1  CAGGATGGGGCATTTCTAGAGG
(SEQ ID NO: 51)  TaGW2-B1  CAGGATGGGGTATTTCTAGAGG
(SEQ ID NO: 52)  TaGW2-D1  CAGGATGGGGTATTTCTAGAGG (SEQ ID NO: 53)  T-1  A1   CAGGATGGGGCATTT.TAGAGG     -1bp
(SEQ ID NO: 54)             CAGGATGGGGCATTTCtTAGAGG    +1bp
(SEQ ID NO: 55)       B1   CAGGATGGGTA....TAGAGG      -4bp
(SEQ ID NO: 56)             CAGGATGGGGTATTC/TAGAGG    +112bp
                      D1   CAGG............AGAGG      -13bp
(SEQ ID NO: 57)             CAGGATGGGGTATTTCtAGAGG     +1bp
(SEQ ID NO: 58)  T-3  B1   CAGGATGGGGTATTTCtAGAGG     +1bp
(SEQ ID NO: 59)       D1   CAGGATGGGGTATTTCcTAGAGG    +1bp
(SEQ ID NO: 60)  T-4  A1   CAGGATGGG.........GAGG     -9bp
(SEQ ID NO: 61)             CAGGATGGGGCTA.....GAGG     -5bp
(SEQ ID NO: 62)       B1   CAGGATGGG......TAGAGG      -7bp
(SEQ ID NO: 63)       D1   CAGGATGGGGTATTCaTAGAGG     +1bp
(SEQ ID NO: 64)             CAGGATGGGGTATTC..GAGG      -2bp
(SEQ ID NO: 65)  T-5  B1   CAGGATGGGGTATTTCgTAGAGG    +1bp
(SEQ ID NO: 66)             CAGGATGGGTAT...TAGAGG      -3bp
                      D1   C..................AGG     -18bp
(SEQ ID NO: 67)             CAGGATGGGTAT...TAGAGG      -3bp
(SEQ ID NO: 68)  T-7  B1   CAGGATGGGGTATTTCcTAGAGG    +1bp
(SEQ ID NO: 69)       D1   CAGGATGGGGTATTTCtTAGAGG    +1bp
(SEQ ID NO: 70)             CAGGATGGGGT............   -14bp
                 T-8  B1   CAGGATGG...............   -15bp
(SEQ ID NO: 71)             CAGGATGGGGTATTTCcTAGAGG    +1bp
(SEQ ID NO: 72)       D1   CAGGATGGGGTATTTCtTAGAGG    +1bp
(SEQ ID NO: 73)             CAGGATGGGGT............   -14bp
```

FIG. 2C mRNA-T-OsBADH2b

| | | |
|---|---|---|
| (SEQ ID NO 74) TGCTTGGATGCTTTGAGTActtgcagatcttgcagaATCCTTGGACAAAAGGCA | WT |
| (SEQ ID NO 75) TGCTTGGATGCTTTGAGTActtgcagatcttg-----cttgcagaATCCTTGGACAAAAGGCA | +5 |
| (SEQ ID NO 76) TGCTTGGATGCTTTGAGTActtgcagatcttgcagaATCCTTGGACAAAAGGCA | -1/+1 |
| (SEQ ID NO 77) TGCTTGGATGCTTTGAGTActtgcagatcttgcccgatcttgcagaATCCTTGGACAAAAGGCA | -1/+1 |
| (SEQ ID NO 78) TGCTTGGATGCTTTGAGTActtgcagatcttgcagtcttgcagaATCCTTGGACAAAAGGCA | -1/+1 |
| (SEQ ID NO 79) TGCTTGGATGCTTTGAGTActttgcagatccctgcagaATCCTTGGACAAAAGGCA | -1/+1 |

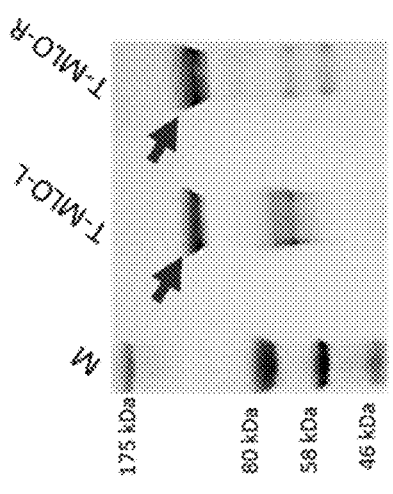

FIG. 3A

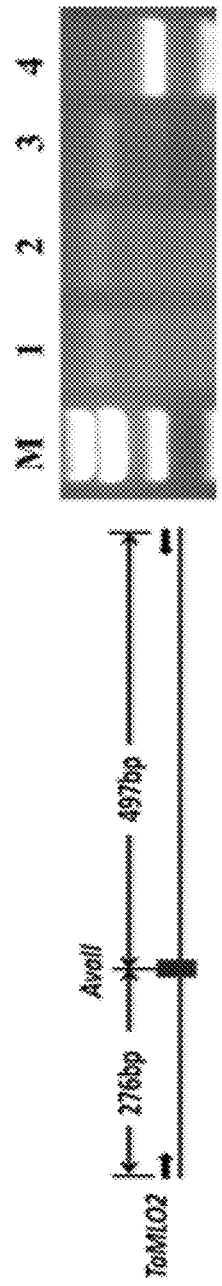

*TaMLO2:*

```
WT: TCGCTGCTGCTCGCCGTgacgcaggacccatctcCGGGATATGCATCTCCGA      (SEQ ID NO: 80)
M1: TCGCTGCTGCTCGCCGTcacgcaggacccaatctcCGGGATATGCATCTCCCA     (SEQ ID NO: 81)    C-A
M2: TCGCTGCTGCTCGCCGTcacgcagga...aatctcCGGGATATGCATCTCCCA    (SEQ ID NO: 82)    -3
M3: TCGCTGCTGCTCGCCGTcacgcagg....aatctcCGGGATATGCATCTCCCA    (SEQ ID NO: 83)    -4
M4: TCGCTGCTGCTCGCCGTcacgcagg......atctcCGGGATATGCATCTCCCA   (SEQ ID NO: 84)    -9
M5: TCGCTGCTGCTCCCCGTcacgc......aatctcCGGTCTATGCATCTCCCA     (SEQ ID NO: 85)    -7
M6: TCGCTGCTGCTCGCCCGTgacgcagga..........cCGGGATATGCATCTCCGA (SEQ ID NO: 87)    -8/+91
```

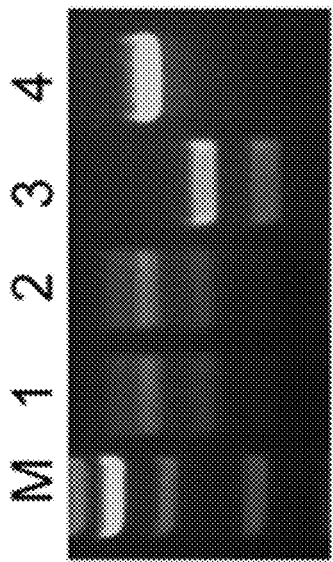
FIG. 4B
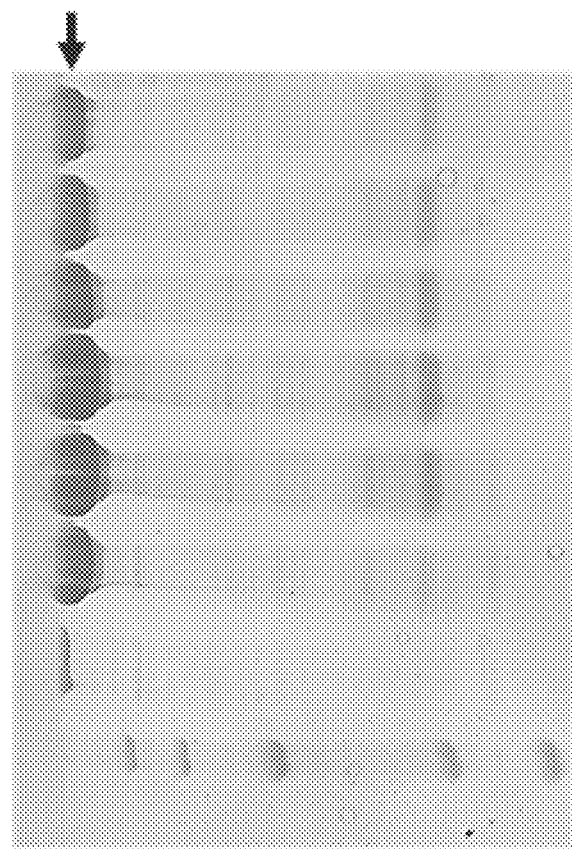
FIG. 4A
FIG. 4C

FIG. 5A

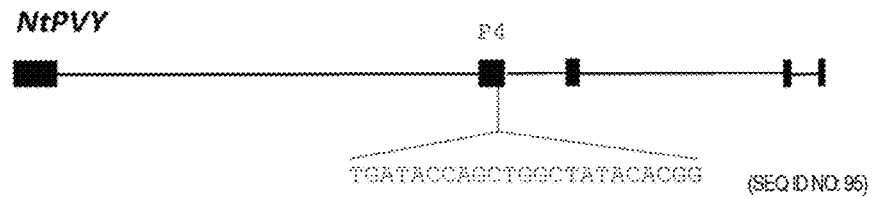

(SEQ ID NO: 95)

FIG. 5B

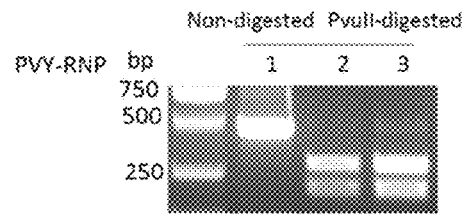

(SEQ ID NO: 96) AGTAAGGGTAAATCTGATACCAGCTGGCTATACACGGTATGCTGAGGATATTTT    WT
(SEQ ID NO: 97) AGTAAGGGT----------------------------------TGCTGAGGATATTTT    -30
(SEQ ID NO: 98) AGTAAGGGTAAATCTGATACCAGCT------ACACGGTATGCTGAGGATATTTT    -6

FIG. 5C

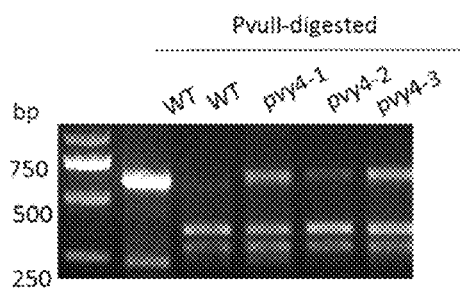

(SEQ ID NO: 99)  Wildtype: TAGTAAGGGTAAATCTGATACCAGCTGGCTATACACGGTATGCTGAGGATATTTT
(SEQ ID NO: 100) pvy4-1:   TAGTA---------------------------ACGGTATGCTGAGGATATTTT   -29
(SEQ ID NO: 101) pvy4-2:   TAGTAAGGGTAAATCTGATACCA-------TACACGGTATGCTGAGGATATTTT   -8
(SEQ ID NO: 102) pvy4-3:   TAGTAAGGGTAAATCTGATACCAGCT------CACGGTATGCTGAGGATATTTT   -7

METHOD FOR MAKING SITE-DIRECTED MODIFICATION TO PLANT GENOMES BY USING NON-INHERITABLE MATERIALS

CROSS-REFERENCE TO RELATED APPLICATIONS

This application is a U.S. National Phase of International Patent Application No. PCT/CN2016/076244, filed on Mar. 14, 2016, which published as WO 2016/155482 A1 on Oct. 6, 2016, and claims priority to Chinese Patent Application No. 201510114017.4, filed on Mar. 16, 2015, all of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Feb. 24, 2019, is named seqlistKWSO244PCTUS_ST25.txt, and is 87,241 bytes in size.

TECHNICAL FIELD

The present invention belongs to the field of plant genetic engineering, and relates to method for making site-directed modification to plant genomes by using non-inheritable materials, specifically to a non-transgenic method for making site-directed modification to plant genome by using protein or mRNA.

TECHNICAL BACKGROUND

Genome editing technology is the most promising means for investigating gene function and improving crops genetically. Currently available genome editing technologies include Zinc finger nucleases (ZFN), Transcription activator-like effector nucleases (TALEN), and Clustered regularly interspaced short palindromic repeats/CRISPR associated systems (CRISPR/Cas9), which are called sequence specific nucleases (SSN). Their common feature is that they can act as an endonuclease to cleave specific DNA sequences, producing DNA double-strand break (DSB). DSB can activate intrinsic repair mechanism of the cell, Non-homologous end joining (NHEJ) and Homologous recombination (HR), so as to repair the DNA damages. Thereby site-directed substitution or insertion mutant can be generated. Currently, genome editing technologies have been efficiently used in some plants (e.g., rice, *Arabidopsis*, maize, wheat) to modify the plant genome, and show significant potential in improving agricultural traits of important crops.

However, although genome editing brings about a promising chance for crop improvement, there is still a great challenge. To conduct genome editing, the sequence-specific nuclease should be expressed in the cell. Currently, the method for expressing the sequence-specific nuclease in plant cells is to deliver an expression vector or DNA fragment expressing the nuclease into the cells via convention transformation approaches (*Agrobacterium*-mediated transformation, particle bombardment, injection and the like). Those inheritable materials randomly integrate into the plant chromosome and transcribe to perform editing. These convention transformation approaches involve the integration of exogenous genes into the plant genome and require selection markers (selection pressure) during the transformation, which may lead to undesirable phenotypes. The application of the plants as obtained would be controlled under GMO regulations. Therefore, it is necessary to establish a method for conducting genome editing in plants without the need of introducing inheritable material DNA.

SUMMARY OF THE INVENTION

The object of the invention is to provide a method for conducting site-directed modification to a target fragment of a target gene in a plant.

The method provided in the present invention for conducting site-directed modification to a target fragment of a target gene in a plant, specifically comprises the following steps: introducing a non-inheritable material into a cell or a tissue or a part of the plant of interest; wherein said non-inheritable material is a nuclease specific to said target fragment or an mRNA expressing said nuclease, thereby the target fragment is cleaved by said nuclease and site-directed modification to the target fragment is achieved through DNA repairing in the plant.

In the present method, a non-inheritable material is introduced in a cell or a tissue or a part of the plant of interest. The non-inheritable material can express a nuclease for conducting site-directed modification to the target fragment, or the non-inheritable material can direct act on the target fragment and achieve the site-directed modification. Along with or after the site-directed modification, said non-inheritable material can be degraded by the metabolic mechanism in the cell. The modified cell or tissue can be regenerated into an intact plant by conventional tissue culture. Consequently, a transgene-free mutant plant is obtained, in which only the target fragment is modified and no exogenous inheritable material has been introduced.

In the present method, said nuclease is a TALEN nuclease, a Zinc finger nuclease, a CRISPR/Cas9 nuclease, or any other nuclease that can achieve genome editing.

Correspondingly, the non-inheritable material can be selected from any one of following (a)-(c):

(a) the non-inheritable material is a TALEN nuclease, or a mRNA capable of expressing paired TALEN proteins; wherein the TALEN protein is composed of a DNA binding domain capable of recognizing and binding to the target fragment, and a Fok I domain.

In one embodiment of the invention (Example 1), said non-inheritable material is composed of mRNAs of SEQ ID NO: 3 and 4. In another embodiment of the invention (Example 2), said non-inheritable material is composed of proteins of SEQ ID NOS: 7 and 8.

(b) the non-inheritable material is a Zinc finger nuclease or a mRNA capable of expressing paired ZFN proteins; wherein the ZFN protein is composed of a DNA binding domain capable of recognizing and binding to the target fragment, and a Fok I domain.

(c) the non-inheritable material is composed of a Cas9 protein or a mRNA capable of expressing a Cas9 protein, and a guide RNA; wherein said guide RNA is an RNA with a palindromic structure which is formed by partial base-pairing between a crRNA and a tracrRNA; said crRNA contains an RNA fragment capable of complementarily binding to the target fragment.

In one embodiment of the invention (Example 3), said non-inheritable material is composed of a protein as shown in SEQ ID NO: 10 and a sgRNA as shown in SEQ ID NO: 11. In another embodiment of the invention (Example 4), said non-inheritable material is composed of a protein as shown in SEQ ID NO: 10 and a sgRNA as shown in SEQ ID NO: 12.

In the present method, said cell may be any cell into which the non-inheritable material can be introduced and which can regenerate into an intact plant through tissue culture. Said tissue may be any tissue into which the non-inheritable material can be introduced and which can regenerate into an intact plant through tissue culture. Said part of the plant is a part of an intact plant (not an ex vivo part) into which the non-inheritable material can be introduced.

Specifically, said cell can be a protoplast cell or a suspension cell. Said tissue can be a callus, an immature embryo, or a mature embryo. Said part of the plant can be a leaf, a shoot apex, a hypocotyl, a young spike or a pollen tube.

In said method, the approach for introducing the non-inheritable material into a cell or a tissue or a part of the plant of interest can be particle bombardment, PEG-mediated protoplast transformation, pollen tube approach, or any other approach that can be used for introducing the non-inheritable material.

In said method, the site-specific modification is nucleotide insertion, deletion, and/or replacement in the target fragment.

Another object of the invention is to provide a method for making a transgene-free mutant plant.

The method of the invention for making a transgene-free mutant plant specifically can comprises the following steps: conducting a site-directed modification to a target fragment of a target gene in a plant of interest, thereby a plant is obtained in which the functions of the target gene are lost or changed and the genome thereof is free of integrated exogenous gene.

In the present invention, the plant can be a monocotyledon or a dicotyledon. In some embodiments, the plant is rice, maize, wheat or tobacco.

Compared with the inheritable material DNA, protein and mRNA are two types of non-inheritable materials which can be easily degraded in the cell by the defense mechanism. Through the transient introduction of an mRNA or a protein of sequence-specific nuclease, mutants with site-directed knocked out genes can be obtained without the integration of the sequence-specific nuclease gene or vector fragment in the plane genome, namely, transgene-free. The method of the invention achieves higher biosafety, and the crop varieties produced by the method would not be regulated as GMO. The present invention has significant values in basic study and crop breeding.

BRIEF DESCRIPTION OF THE DRAWINGS

FIG. 3 shows mutagenesis of wheat MLO gene by transformation of wheat protoplasts with MLO-TALEN proteins. A: SDS-PAGE results showing prokaryotic expression and purification of T-MLO-L and T-MLO-R for the MLO target site. B: PCR/RE results showing the mutations in target site generated by the TALEN proteins in the protoplasts. C: the sequencing results indicate in vitro generated TALEN proteins induced mutations at the target site. WT represents wild-type gene sequence, "–" represents a sequence with deletion, "+" represents a sequence with insertion, the number after "–/+" represents the number of the deleted or inserted nucleotides.

FIG. 4 shows mutagenesis of wheat TaGASR7 gene by transformation of wheat protoplasts with Cas9 protein and in vitro transcribed sgRNA. A: SDS-PAGE results showing prokaryotic expression and purification of Cas9 protein. B: PCR/RE results showing the mutations in target site generated by Cas9 protein and in vitro transcribed sgRNA. C: the sequencing results indicate in vitro generated Cas9 protein and in vitro transcribed sgRNA induced mutations at the target site. WT represents wild-type gene sequence, "–" represents a sequence with deletion, "+" represents a sequence with insertion, the number after "–/+" represents the number of the deleted or inserted nucleotides.

FIG. 5 shows that NtPVY gene mutations were generated by co-transformation of Cas9 protein and in vitro transcribed sgRNA into tobacco protoplasts, and mutant plants were obtained by regeneration. A: PCR/RE results of the protoplasts showing the mutations in target site generated by Cas9 protein and in vitro transcribed sgRNA. B: the sequencing results indicate co-transformation of in vitro generated Cas9 protein and in vitro transcribed sgRNA into tobacco protoplasts induced mutations at the target site. C: Detection of mutant plants regenerated from the protoplasts, and sequencing results of the target sites. WT represents wild-type gene sequence, "–" represents a sequence with deletion, "+" represents a sequence with insertion, the number after "–/+" represents the number of the deleted or inserted nucleotides.

DETAILED EMBODIMENTS

Figure 1A:
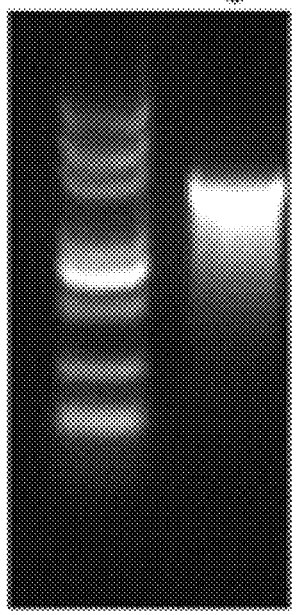
FIG. 1 shows that TaGW2 gene mutations were generated by transforming wheat immature embryo with Cas9 mRNA and sgRNA. A: a gel electrophoretogram of Cas9-mRNA in vitro transcribed with a mRNA transcription kit (AM1344, Ambion). B: PCR/RE results showing the mutations in target site of TaGW2 in T0 plants generated by Cas9 mRNA and sgRNA-GW2-C14. C: the sequencing results indicate in vitro transcribed Cas9 mRNA and sgRNA-GW2-C14 induced mutations at the target site. WT represents wild-type gene sequence, "–" represents a sequence with deletion, "+" represents a sequence with insertion, the number after "–/+" represents the number of the deleted or inserted nucleotides.

The experimental methods used in the following Examples are all conventional methods, unless otherwise indicated.

The materials, reagents used in the following Examples are all commercially available, unless otherwise indicated.

The wheat variety Bobwhite is disclosed in "Weeks, J. T. et al. Rapid production of multiple independent lines of fertile transgenic wheat. Plant Physiol. 102: 1077-1084, (1993)", and can be obtained from the Institute of Genetics and Developmental Biology of the Chinese Academy of Sciences.

Wheat TaMLO gene-targeting TALENs vector T-MLO is disclosed in "Wang, Y, Cheng, X., Shan, Q., Zhang, Y, Liu, J., Gao, C., and Qiu, J. L. (2014). Simultaneous editing of three homoeoalleles in hexaploid bread wheat confers heritable resistance to powdery mildew. Nature Biotechnology.

32, 947-951", and can be obtained from the Institute of Genetics and Developmental Biology of the Chinese Academy of Sciences.

Prokaryotic expression vector pGEX-4T was obtained from Shanghai BeiNuo Biotechnology Co. Ltd., Cat. No. 1110024.

Cas9-mRNA in vitro transcription vector pXT7-Cas9 was disclosed in "Chang N, Sun C, Gao L, Zhu D, Xu X, et al. 2013. Genome editing with RNA-guided Cas9 nuclease in zebrafish embryos. Cell research 23: 465-72", and can be obtained from the authors.

pT7-gRNA vector was disclosed in "A programmable dual-RNA-guided DNA endonuclease in adaptive bacterial immunity. Science 337(6096): 816-821", and can be obtained from the Institute of Genetics and Developmental Biology of the Chinese Academy of Sciences.

Maize variety Hill was disclosed in "Armstrong, C. L., Green, C. E.& Phillips, R. L. Development and availability of germplasm with high type II culture formation response. Maize Genet. Coop. News Lett. 65, 92-93 (1991)", and can be obtained from the Institute of Genetics and Developmental Biology of the Chinese Academy of Sciences.

Solutions used in the preparation and transformation of rice protoplast are shown in Tables 1-5.

TABLE 1

50 ml enzymolysis solution

| | The amount added | Final Concentration |
|---|---|---|
| Cellulase R10 | 0.75 g | 1.5% |
| Macerozyme R10 | 0.375 g | 0.75% |
| mannitol | 5.4651 g | 0.6M |
| 2-(N-Morpholino)ethanesulfonic acid | 0.1066 g | 10 mM |
| made up to 50 ml with double distilled water, pH adjusted to 5.7 with KOH; incubated in 55° C. water bath for 10 min, and cooled at room temperature before adding | | |
| CaCl$_2$ | 0.0735 g | 10 mM |
| BSA | 0.05 g | 0.1% |
| filtered with a 0.45 μm filter | | |

TABLE 2

500 ml W5

| | The amount added | Final Concentration |
|---|---|---|
| NaCl | 4.5 g | 154 mM |
| CaCl$_2$ | 9.189 g | 125 mM |
| KCl | 0.1864 g | 5 mM |
| 2-(N-Morpholino)ethanesulfonic acid | 0.2132 g | 2 mM |
| made up to 500 ml with double distilled water, pH adjusted to 5.7 with NaOH | | |

TABLE 3

10 ml MMG solution

| | The amount added | Final Concentration |
|---|---|---|
| mannitol (0.8M) | 5 ml | 0.4M |
| MgCl$_2$ (1M) | 0.15 ml | 15 mM |
| 2-(N-Morpholino)ethanesulfonic acid (200 mM) | 0.2 ml | 4 mM |
| double distilled water | Made up to 10 ml | |

TABLE 4

4 ml PEG solution

| | The amount added | Final Concentration |
|---|---|---|
| PEG4000 | 1.6 g | 40% |
| mannitol (0.8M) | 1 ml | 0.2M |
| CaCl$_2$ (1M) | 0.4 ml | 0.1M |
| double distilled water | Made up to 4 ml | |

TABLE 5

250 ml WI solution

| | The amount added | Final Concentration |
|---|---|---|
| mannitol | 27.324 g | 0.6M |
| KCl | 0.07456 g | 4 mM |
| 2-(N-Morpholino)ethanesulfonic acid (200 mM) | 0.2135 g | 4 mM |
| made up to 250 ml with double distilled water, pH adjusted to 5.7 with KOH | | |

% in above Tables 1-5 indicates weight-volume percentage, g/100 ml.

The medium used for wheat tissue culture include:

Hypertonic medium: MS minimal medium, 90 g/L mannitol, 5 mg/L 2,4-D, 30 g/L sucrose, and 3 g/L, phytogel, pH 5.8.

Induction medium: MS minimal medium, 2 mg/L 2,4-D, 0.6 mg/L cupric sulfate, 0.5 mg/L casein hydrolysates, 30 g/L, sucrose, and 3 g/L phytogel, pH 5.8.

Differentiation medium: MS minimal medium, 0.2 mg/L kinetin, 30 g/L sucrose, and 3 g/L phytogel, pH 5.8.

Rooting medium: ½ of MS minimal medium, 0.5 mg/L ethanesulfonic acid, 0.5 mg/L α-naphthylacetic acid, 30 g/L, sucrose, and 3 g/L phytogel, pH 5.8.

Example 1. Site-Directed Editing of TaGW2 by Transforming Wheat Immature Embryo with In Vitro Transcribed Cas9 mRNA and sgRNA I. Design of the Target Fragment: Target-C14

Target-C14:
                                    SEQ ID NO: 18
5'- CCAGGATGGGGTATTTCTAGAGG-3' (in the conserved region of exon 8 of wheat TaGW2, Groups A, B and D;).

II. In Vitro Transcription and Purification of Cas9-mRNA 1. pXT7-Cas9 vector was digested with XbaI. The digested product was purified with a purification kit (Axygen) to a concentration of higher than 100 ng/μl, and designated as pXT7-Cas9-XbaI.

2. The purified product pXT7-Cas9-XbaI was transcribed with an in vitro transcription kit (AM1344, Ambion). The product was purified with a mRNA purification kit (AM1908, Ambion) to a concentration of higher than 500 ng/μl. The Agarose gel electrophoretogram of the in vitro transcribed Cas9-mRNA was shown in FIG. 1A.

III. In Vitro Transcription of sgRNA Against the Target Site

1. The Target Site of TaGW2 was Constructed in the pTaU6-gRNA Vector

The following single-stranded oligonucleotides with sticky ends (underlined) were synthesized:

```
C14F:
                                  (SEQ ID NO: 19)
5'-CTTGCAGGATGGGGTATTTCTAG-3';

C14R:
                                  (SEQ ID NO: 20)
5'-AAACCTAGAAATACCCCATCCTG-3'.
```

Double-stranded DNA with sticky ends was formed through annealing between C14F/C14R, and inserted between the two BbsI restriction sites in pTaU6-gRNA plasmid, resulting in a pTaU6-gRNA plasmid containing C14 site. The positive plasmid was verified by sequencing. A recombinant plasmid, which was obtained by inserting the DNA fragment as shown in 5'-CTTGCAGGATGGGGTAT-TTCTAG-3' (SEQ ID NO: 19) in forward direction at the BbsI restriction site of pTaU6-gRNA plasmid, was positive, and designated as pTaU6-gRNA-C14.

2. In Vitro Amplification and Purification of the DNA Fragment of T7-TaGW2-gRNA Primer Design

```
T7-TaGW2-F:
                                  (SEQ ID NO: 21)
TAATACGACTCACTATAGGCAGGATGGGGTATTTCTAG;

gRNA-PCR-R:
                                  (SEQ ID NO: 22)
AGCACCGACTCGGTGCCACTT.
```

PCR amplification was performed with pTaU6-gRNA-C14 as the template. PCR product was purified with a PCR purification kit (AP-GX-250G, Axygen) to a concentration of higher than 100 ng/μl. The resulted PCR product is a sgRNA containing T7 promoter and the TaGW2 target site, and designated as T7-TaGW2-gRNA.

3. In Vitro Transcription of the sgRNA Containing the TaGW2 Target Site sgRNA-GW2-C14 (as shown in SEQ ID NO:17) was in vitro transcribed with a T7 in vitro transcription kit (E2040S, NEB).

IV. Site Directed Editing of Wheat TaGW2 Gene by Particle Bombardment Transformation of In Vitro Transcribed Cas9-mRNA and In Vitro Transcribed sgRNA 1. Loading In Vitro Transcribed Cas9-mRNA and In Vitro Transcribed sgRNA to 0.6 nm Gold Powder 5 μl 0.6 nm gold powder, 3 μl Cas9-mRNA, 1 μl sgRNA-GW2-C14, 1 μl 5M ammonium acetate, 20 μl isopropanol were mixed and precipitated at −20° C. for 1 h, so as to allow the Cas9-mRNA and sgRNA-GW2-C14 to attach to the gold powder. The mixture was centrifuged at 1000 rpm for 5 sec and washed in 100 μl dehydrated alcohol after discarding the supernate, then centrifuged at 1000 rpm for 5 sec again and resuspended in 20 μl dehydrated alcohol after discarding the supernate.

2. Transformation of Wheat Recipient Materials Using Particle Bombardment

1) Immature embryo of the wheat variety KN199 was taken and treated for 4 hours using hypertonic medium.
2) A particle bombardment device was used to bombard the wheat immature embryo that was hypertonically cultured in step 1). 20 μl of the sgRNA-Cas9-mRNA mixture was loaded on the membrane and bombarded; the bombarding distance for each bombardment was 6 cm, the bombarding pressure was 1100 psi, the bombarding diameter was 2 cm.
3) The wheat immature embryo bombarded in step 2) was hypertonically cultured for 16 hours;
4) The wheat immature embryo hypertonically cultured in step 3) were then sequentially subjected to 14 days of callus tissue induction culture, 28 days of differentiation culture, and 14-28 days of rooting culture, so as to obtain wheat plants.
5) DNA was extracted from the wheat seedlings generated in step 4) and mutants with gene knocked-out (site-directed) were detected through PCR/RE tests (for specific test method, please refer to step IV). Wild-type wheat variety Kn199 was used as control.

Since there is a sequence recognized by the restriction endonuclease XbaI in the target fragment of wheat endogenous gene TaGW2, XbaI was used to perform the PCR/RE tests. The primers used in PCR amplification are primers specific to Groups A, B and D, having the following sequences:

```
TaGW2-AF:
                                  (SEQ ID NO: 23)
5'- CTGCCATTACTTTGTATTTTGGTAATA-3';

TaGW2-BF:
                                  (SEQ ID NO: 24)
5'- GTTCAGATGGCAATCTAAAAGTT-3';

TaGW2-DF:
                                  (SEQ ID NO: 25)
5'- GCATGTACTTTGATTGTTTGCGTGA-3';

TaGW2-R:
                                  (SEQ ID NO: 26)
5'- TCCTTCCTCTCTTACCACTTCCC-3'.
```

Figure 1B:
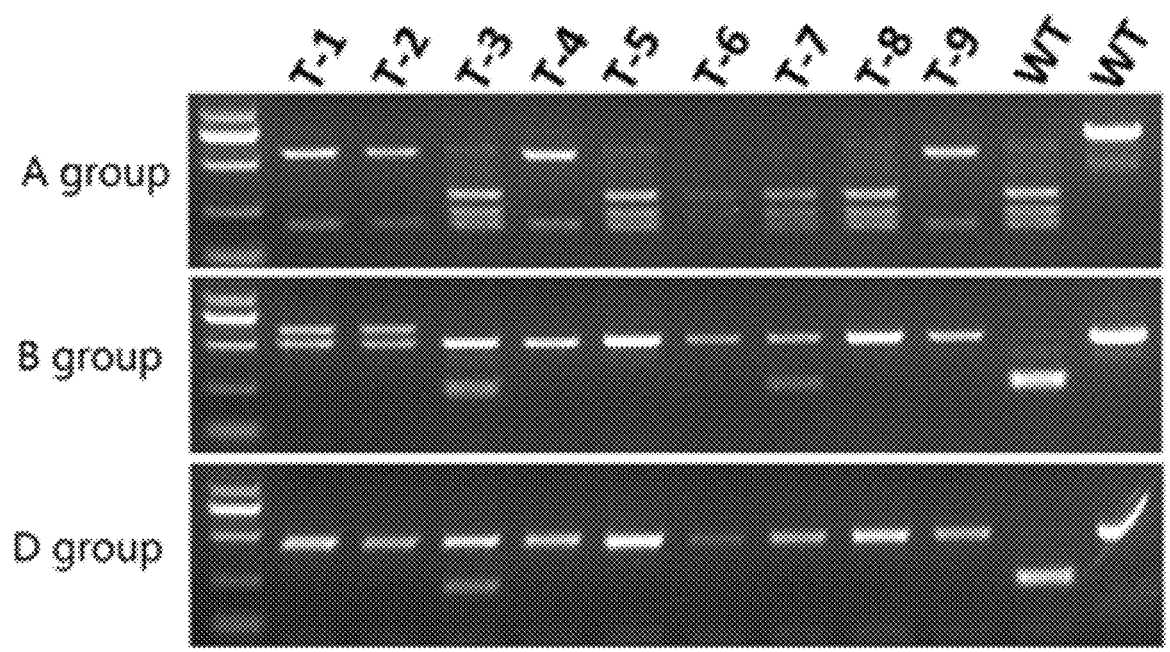

The results of some detection tests indicate that mutations occurred in the target site of wheat TaGW2 gene. Bands were recovered for sequencing. The sequencing results indicate that insertion/deletion (indel) occurred in the target site of wheat TaGW2 gene (FIGS. 1 B and C).

Example 2. Site-Directed Editing of OsBADH2 Gene by Transforming Rice Protoplasts with In Vitro Transcribed TALEN mRNA I. TALEN Target Fragment The sequence of rice BADH2 gene is shown in SEQ ID NO:1.

TALEN target fragment is located in the fourth exon of rice BADH2 gene, and has the following sequence:
5'-GCTGGATGCTTTGAGTActttgca-gatcttgcagaATCCTTGGACAAAAGGC-3' (SEQ ID NO: 27; positions 1589-1640 of SEQ ID NO: 1); the lower case letters in the middle represent a spacer sequence; and the flanking uppercase letters represent the sequences recognized by the TALEN modules (designated as L-b and R-b). Underlined is the sequence recognized by BglII.

II. Design and Synthesis of Talen Encoding Genes

The TALEN protein that recognizes L-b in the target sequence was designated as T-BADH2b-L, while the encoding sequence is shown in positions 7-2952 of SEQ ID NO: 2. Positions 7-27 of SEQ ID NO: 2 encodes foe a nucleic localization signal (NLS); positions 463-2154 encodes for the L-b sequence recognizing module protein; positions 2350-2953 (603 bp) encodes for an endonuclease Fok I.

The TALEN protein that recognizes R-b in the target sequence was designated as T-BADH2b-R, while the encoding sequence is shown in positions 3085-6018 of SEQ ID NO:2. Positions 3085-3105 of SEQ ID NO: 2 encodes foe a nucleic localization signal (NLS); positions 3541-5232 encodes for the L-b sequence recognizing module protein; positions 5428-6018 (591 bp) encodes for an endonuclease Fok I.

Positions 2953-3006 of SEQ ID NO: 2 encodes for T2A which is composed of 18 amino acids and allows T-BADH2b-L and T-BADH2b-R expressed in a same expression cassette to break into two individual proteins.

III. In Vitro Synthesis of mRNA of TALEN Gene

The two components of TALEN for rice BADH2 gene, T-BADH2b-L and T-BADH2b-R, were in vitro transcribed with an mRNA transcription kit (Ambion) by using the T7 promoter to initiate the transcription. mRNA-L-T-OsBADH2b and mRNA-R-T-OsBADH2b were obtained, and PolyA tails were added to the 3' end thereof for increasing the stability of the mRNA.

The sequence of mRNA-L-T-OsBADH2b is shown in SEQ ID NO: 3, and the sequence of mRNA-R-T-OsBADH2b is shown in SEQ ID NO: 4.

IV. Introduction of the Mixture of two mRNAs of TALEN Obtained by In Vitro Transcription into Rice Protoplasts 1. Preparation of the Materials The rice variety as used is Nipponbare. Seeds were rinsed in 75% ethanol, then treated with 2.5% sodium hypochlorite for 20 min, washed with sterile water for more than 5 times, and cultured on ½ MS medium for 7-10 days under 26° C., 12 h light (150 µmol·m$^{-1}$·s$^{-1}$). 15 seeds may be cultured in a big glass culture bottle. For one experiment, 40-60 seedlings are required and the amount of isolated protoplasts is sufficient for transformation of 6 plasmids.

2. Isolation of Protoplasts

1) Shoots and leaf sheathes were used for isolation of protoplasts. They were cut into 0.5 mm threads;
2) The threads were transferred to 0.6M mannitol solution immediately, placed in dark for 10 min;
3) The mannitol solution was removed by filtration, and the threads were transferred into enzymolysis solution, treated in a vacuum pump for 30 min at −15~−20 (mmHg) in dark;
4) the samples were digested for additional 4-5 hours with gentle shaking (on a shaker at a speed of 10 rpm);
5) equal volume of W5 solution was added after digestion and the solution should be shaken for 10 sec so as to release the protoplasts;
6) the protoplasts were filtrated into a 50 ml round bottom centrifuge tube using a 40 µm Nylon filter membrane, and W5 solution was added for washing;
7) 250 g centrifugation for 3 min for precipitating the protoplasts, and the supernatant was discarded;
8) the protoplasts were resuspended in 10 ml W5, centrifuged at 250 g for 5 min, and the supernatant was discarded;
9) the protoplasts were resuspended by adding a proper amount of MMG solution. The concentration of the protoplasts is 2×10$^6$/ml, as determined by counting with a haemocytometer.

Note: all the above steps were performed under room temperature.

3. Transformation of Protoplasts 1) 10 µg mRNA-L-T-OsBADH2b and 10 µg mRNA-R-T-OsBADH2b were added into a 2 ml centrifuge tube. 200 µl of the protoplasts (about 4×10$^5$ cells) were added. Then 220 µl of fresh PEG solution was added and mixed. Transformation was performed in dark for 10-20 min under room temperature;
2) after transformation, 880 µl W5 was added slowly and mixed by reversing, 250 g centrifugation for 3 min, and the supernatant was discarded;
3) the protoplasts was resuspended by adding 1 ml WI, and transferred to a 6-well plate (with pre-added 1 ml WI), and then cultured at RT or 28° C. in the dark for 6-16 hours (for 48 hours if the protoplasts are used for genomic DNA extraction);
4. Using PCR/RE experiments to analyze the mutagenesis of rice endogenous gene BADH2 resulted from in vitro transcribed TALEN 48 hours after the transformation of the protoplasts, genomic DNA was extracted, which was used as template for PCR/RE (Polymerase Chain Reaction/Restriction digestion) experiment analysis. At the same time, the protoplasts of wild-type rice variety Nipponbare were used as a control. PCR/RE analysis method is based on Shan, Q. et al. Rapid and efficient gene modification in rice and Brachypodium using TALENs. Molecular Plant (2013). Since the target site of rice endogenous gene BADH2 contains the recognition sequence of restriction endonuclease BglII, the restriction endonuclease BglII was used in the experiment for conducting the PCR/RE test. Primers used in the PCR amplification are:

```
OsBADH-F:
                                    (SEQ ID NO: 28)
5'-GATCCCGCAGCGGCAGCTCTTCGTCG-3';

OsBADH2-R:
                                    (SEQ ID NO: 29)
5'-GAGGAATAAAATCTCAAATGTCTTCAACTT-3'.
```

Figure 2A:
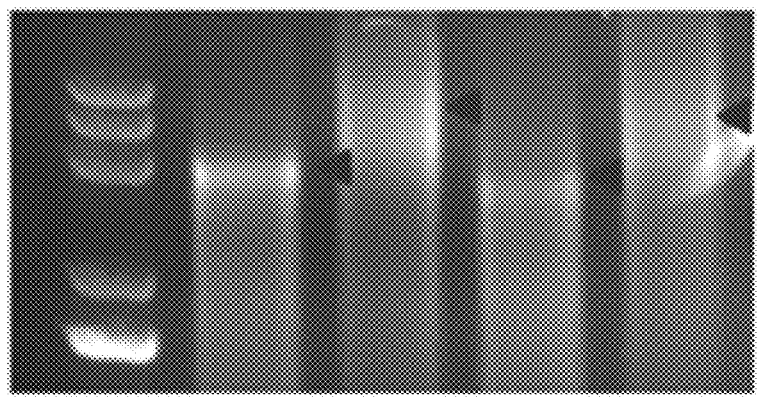
FIG. 2 shows that OsBADH2 gene mutations were generated by transiently transforming rice protoplasts with mRNA-TALEN. A: a gel electrophoretogram showing in vitro transcription of T-BADH2b-L and T-BADH2b-R with a mRNA transcription kit (AM1344, Ambion), and a PolyA tail was added to the 3'end of the mRNA. B: PCR/RE results showing the mutations in target site generated by in vitro transcribed mRNA in the protoplasts. C: the sequencing results indicate in vitro transcribed mRNA induced mutations at the target site. WT represents wild-type gene sequence, "–" represents a sequence with deletion, "+" represents a sequence with insertion, the number after "–/+" represents the number of the deleted or inserted nucleotides.
Figure 2B:
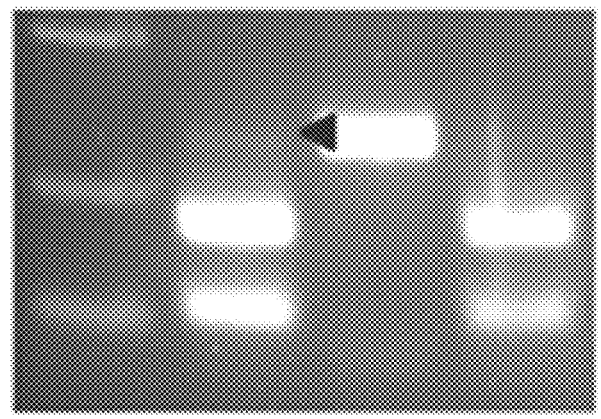

The results of PCR/RE experiments can be seen in FIG. 2B, and the results showed that: mutations occurred at the target site of BADH2 gene, and the mutagenesis efficiency is about 5%. The bands in the figure were recovered and sequenced, and the sequencing results showed that insertion/deletion (indel) occurred at the target site of BADH2 gene (FIG. 2C).

Example 3. Expression and Purification of TALEN Proteins in a Prokaryotic Expression System, and Transformation of the Same into Wheat Protoplasts or Immature Embryos for Site-Directed Modification of MLO Gene I. Selection of Target Sequences and Design of the TALENs A conserved region in exon 2 of wheat MLO gene was used as the target sequence to design a pair of TALENs (consisting of TAL-MLO-L protein and TAL-MLO-R protein; TAL-MLO-L protein is composed of two functional fragments, namely a fragment specifically binds to upstream nucleotides of the target sequence and a Fok I endonuclease with EL mutation; TAL-MLO-R protein is composed of two functional fragments, namely a fragment specifically binds to downstream nucleotides of the target sequence and a Fok I endonuclease with KK mutation). The target sequences of said TALENs in TaMLO-A, TaMLO-B and TaMLO-D genes are listed as follows:

TaML0-A gene:
(SEQ ID NO: 30)
5'-TCGCTGCTGCTCGCCGTcacgcaggacccaatctcCGGGATATGCAT
CTCCCA-3';

TaML0-B gene:
(SEQ ID NO: 31)
5'-TCGCTGCTGCTCGCCGTgacgcaggacccatctcCGGGATATGCAT
CTCCGA-3';

TaML0-D gene:
(SEQ ID NO: 32)
5'-TCGCTGCTGCTCGCCGTgacgcaggacccaatctcCGGGATATGCAT
CTCCGA-3'.

In the wheat cell, when the TAL-L fragment and TAL-R fragment bind to respective binding region, the two different monomer Fok I endonucleases (Fok I endonuclease with EL mutation and Fok I endonuclease with KK mutation) will form an active Fok I dimmer endonuclease which cleaves in the target sequence region (including the target sequence and the flanking sequences) to generate a double-strand break. During the repair of said break by the cell, a number of mutations will be introduced. Here, "mutation" has a broad meaning, including insertion, deletion, replacement and the like, most of which result in loss of gene function.

In the above target sequences, the underlined portion is the recognition sequence of restriction nuclease AvaII which can be cut by AvaII. After the generation of break, if a mutation occurs and interrupts the AvaII recognition sequence, the target sequence cannot be cut by AvaII; if no mutation occurs, the target sequence can be cut by AvaII.

II. Expression and Purification of TALEN Proteins for MLO Gene Target in a Prokaryotic Expression System 1. Construction of Prokaryotic Expression Vectors for Expressing TALEN Proteins 1) Encoding regions of TAL-L (SEQ ID NO: 5) and TAL-R (SEQ ID NO: 6) of the TALEN gene were constructed into a prokaryotic expression vector pGEX-4T, so that a recombinant vector was obtained with the TAL-L encoding region (SEQ ID NO: 5) inserted between the BamHI and XbaI sites of pGEX-4T in a forward direction, while the TAL-R encoding region (SEQ ID NO: 6) inserted between the XbaI and BamHI sites of pGEX-4T in a forward direction. The recombinant vector was transformed into *E. coli* BL21. A positive colony was inoculated into LB medium supplemented with ampicillin and chloramphenicol and cultured under 37° C. over night. The culture was then inoculated to 5 ml fresh LB medium at a ratio of 1:100, cultured under 37° C. at 225 rpm to OD600≈0.5. 1 ml of the culture was taken as the negative control (no induction). Controls of empty pGEX-4T vector were also set up, with or without induction. For the remaining culture, IPTG was added (final concentration of 1 mM) to induce expression under 37° C. at 225 rpm for 8 h.

2) 1 ml of each of the control or induced culture was taken and centrifuged at 12000 rpm for 10 min to collect the bacteria cells, discarding the supernatant. The cells were resuspended by adding 50 µL protein loading buffer, boiled for 7 min. The supernatant was analyzed by 10% SDS-PAGE. The molecular weight of each TALEN protein is about 100 Kda. The amino acid sequence of the TAL-MLO-L protein is shown in SEQ ID NO: 7. The amino acid sequence of the TAL-MLO-R protein is shown in SEQ ID NO: 8.

2. Purification of TALEN Proteins

The bacteria culture was centrifuged under 4° C. for 10 min to collect the bacteria cells. 10 ml lysis buffer (50 mM Tris-HCl, 2 mM EDTA, 100 mM NaCl, 1 mg/ml lysozyme, pH 8.5) was added to the pellet, mixed on ice for 45 min. After ultrasonication, pellet was collected by centrifugation, washed with 4M Imidazole. The pellet obtained after a further centrifugation was dissolved in 50 mM phosphate buffer (containing 8M Urea) of pH 7.4. (FIG. 3A)

III. Introduction of the Purified TALEN Proteins into Wheat Protoplasts for Site-Directed Editing of the MLO Gene The purified TALEN proteins against the target site of MLO gene were introduced into protoplasts of wheat variety Bobwhite via PEG-mediated approach as follows:

1. Growth of Wheat Seedling

Wheat seeds were grown in a culturing room, under 25±2° C., illuminance 1000 Lx, 14-16 h light/d, for about 1-2 weeks.

2. Isolation of Protoplast

1) Tender leaves of wheat were taken, and the middle part thereof was cut into 0.5-1 mm threads using a cutter blade, placed into 0.6M of mannitol solution (using water as solvent) for 10 min in dark. The mixture was then filtrated using a filter, then placed in 50 ml enzymolysis solution for 5 h of digestion (0.5 h enzymolysis in vacuum, then 4.5 h slow shaking at 10 rpm).

Note: The temperature during enzymolysis should be kept between 20-25° C., the reaction should be carried out in the dark; and the solution should be gently shaken after the reaction so as to release the protoplasts.

2) the enzymolysis product was diluted by adding 10 ml of W5, and filtrated into a 50 ml round bottom centrifuge tube using a 75 µm Nylon filter membrane.

Note: The Nylon filter membrane should be submerged in 75% (volume percentage) ethanol, washed with water and then soaked in W5 for 2 min before use.

3) 23° C., 100 g centrifugation for 3 min, and the supernatant was discarded.

4) the pellet was suspended with 10 ml W5, placed on ice for 30 min; the protoplasts eventually formed sedimentation, and the supernatant was discarded.

5) the protoplasts were suspended by adding a proper amount of MMG solution, placed on ice until transformation.

Note: The concentration of the protoplasts needs to be determined by microscopy (×100). The amount of protoplasts was $2 \times 10^5$/ml to $1 \times 10^6$/ml.

3. Transformation of Wheat Protoplast 1) 15 µg TALEN proteins (TAL-MLO-L protein and TAL-MLO-R protein mixed in equal amount) or 20 µg T-MLO vector (control) were added into a 2 ml centrifuge tube. 200 µl of the isolated protoplasts was added using a pipette and then mixed by gentle patting, kept still for 3-5 min. Then 250 µl of PEG4000 was added and mixed by gentle patting. Transformation was performed in dark for 30 min;

2) 900 µl W5 (room temperature) was added and mixed by reversing, 100 g centrifugation for 3 min, and the supernatant was discarded;

3) 1 ml W5 was added and mixed by reversing, the content was gently transferred to a 6-well plate (with pre-added 1 ml W5), and then cultured at 23° C. overnight.

4. Using PCR/RE Experiments to Analyze the Mutagenesis of Wheat Endogenous Gene MLO Resulted from Purified TALEN Proteins 48 hours after the transformation of wheat protoplasts, genomic DNA was extracted, which was used as template for PCR/RE (Polymerase Chain Reaction/Restriction digestion) experiment analysis. At the same time, the protoplasts transformed with T-MLO plasmid or protoplasts of wild-type wheat variety Bobwhite were used as control. PCR/RE analysis method is based on Shan, Q. et al. Rapid and efficient gene modification in rice and Brachypodium using TALENs. Molecular Plant (2013). Since the target fragment of wheat endogenous gene MLO contains the recognition sequence of restriction endonuclease AvaII, AvaII was used in the experiment for conducting the PCR/RE test. Primers used in the PCR amplification were:

```
TaMLO-F:
                                        (SEQ ID NO: 33)
5'-TCATCGTCTCCGTCCTCCTGGAGCA-3';

TaMLO-R:
                                        (SEQ ID NO: 34)
5'-TGGTATTCCAAGGAGGCGGTCTCTGTCT-3'.
```

The results of PCR/RE experiments showed that: mutations occurred at the target site of MLO gene. The bands were recovered and sequenced, and the sequencing results showed that insertion/deletion (indel) occurred at the target site of MLO gene. (FIGS. 3B and 3C)

IV. Site-Directed Editing of the MLO Gene by Introduction of the TALEN Proteins Using Particle Bombardment Generally, transformation of an expression plasmid into cells by particle bombardment is using gold powder as the carrier to carry the DNA plasmid into the cells. However, for proteins, gold powder is not suitable as the carrier as it is difficult to bind a protein to the gold powder. In the present invention, silica is used as the carrier for transforming proteins with particle bombardment.

1. Loading Proteins to Silica

Silica Au-MSN with aperture of 10 nm was used as the carrier. 20 mg of Au-MSN was added to 5 ml phosphate buffer (PBS) of pH 7.4 for sonication, and then 7 mg of purified TAL-MLO-L protein and TAL-MLO-R protein were added. The mixture was stirred under 22° C. for 24 hours, centrifuged at 12000 rpm. The supernatant was discarded. Pellet was suspended with PBS buffer.

2. Transformation of Wheat Recipient Materials Using Particle Bombardment

1) Immature embryo of the wheat variety Bobwhite was taken and treated for 4 hours using hypertonic medium.
2) A particle bombardment device was used to bombard the wheat immature embryo that was hypertonically cultured in step 1). Au-MSN loaded with TALEN proteins (5 µl, 20 µg/µl) was loaded on the membrane and bombarded; the bombarding distance for each bombardment was 6 cm, the bombarding pressure was 1100 psi, the bombarding diameter was 2 cm.
3) The wheat immature embryo bombarded in step 2) was hypertonically cultured for 16 hours;
4) The wheat immature embryo hypertonically cultured in step 3) were then sequentially subjected to 14 days of callus tissue induction culture, 28 days of differentiation culture, and 14-28 days of rooting culture, so as to obtain wheat plants.
5) DNA was extracted from the wheat seedlings generated in step 4) and mutants with gene knocked-out (site-directed) were detected through PCR/RE tests (for specific test method, please refer to step III). Wild-type wheat variety Bobwhite was used as control.

The detection results of some mutants indicate that mutations occurred in the target site of wheat MLO gene. Bands were recovered for sequencing. The sequencing results indicate that insertion/deletion (indel) occurred in the target site of wheat MLO gene.

The above results demonstrated that site-directed editing of a target site can be achieved by introducing nuclease protein into wheat. The mutants obtained by this method are free of exogenous DNA, and the protein as introduced will be degraded by the plant cell. Therefore, the mutants obtained by this method are transgene-free plants, having high biosafety.

Example 4. Site-Directed Editing of TaGASR7 Gene by Co-Transformation of a Cas9 Protein Expressed and Purified in Prokaryotic Expression System and an In Vitro Transcribed sgRNA I. Design of the Target Fragment: Target-C5

```
Target-C5:
                                        (SEQ ID NO: 35)
5'-CCGCCGGGCACCTACGGCAAC-3'; (in the TaGASR7 gene as shown in Genbank No. EU095332, positions 248-268).
```

II. Prokaryotic Expression and Purification of Cas9 Protein

1. Cas9 gene (optimized for plant codon usage and added with NLS at both ends) was constructed into a prokaryotic expression vector pGEX-4T, so that a recombinant vector was obtained with a Cas9 gene of SEQ ID NO: 9 (optimized for plant codon usage and added with NLS at both ends) inserted between BamHI and SpeI of the pGEX-4T vector. The recombinant vector was transformed into E. coli BL21. A positive colony was inoculated into LB medium supplemented with ampicillin and chloramphenicol and cultured under 37° C. over night. The culture was then inoculated to 5 ml fresh LB medium at a ratio of 1:100, cultured under 37° C. at 225 rpm to OD600≈0.5. 1 ml of the culture was taken as the negative control (no induction). Controls of empty pGEX-4T vector were also set up, with or without induction. For the remaining culture, IPTG was added (final concentration of 1 mM) to induce expression under 37° C. at 225 rpm for 8 h.

2. 1 ml of each of the control or induced culture was taken and centrifuged at 12000 rpm for 10 min to collect the bacteria cells, discarding the supernatant. The cells were resuspended by adding 50 µL protein loading buffer, boiled for 7 min. The supernatant was analyzed by 10% SDS-PAGE. The molecular weight of the Cas9 protein is about 200 KDa. The amino acid sequence of the Cas9 protein is shown in SEQ ID NO: 10.

2. Purification of the Cas9 Protein

The bacteria culture was centrifuged under 4° C. for 10 min to collect the bacteria cells. 10 ml lysis buffer (50 mM Tris-HCl, 2 mM EDTA, 100 mM NaCl, 1 mg/ml lysozyme, pH 8.5) was added to the pellet, mixed on ice for 45 min. After ultrasonication, pellet was collected by centrifugation, washed with 4M Imidazole. The pellet obtained after a further centrifugation was dissolved in 50 mM phosphate buffer (containing 8M Urea) of pH 7.4. (FIG. 4A)

III. In Vitro Transcription of the sgRNA of the Target Site

1. The Target Site of TaGASR7 was Constructed into the pT7-gRNA Vector

C5 is the DNA sequence coding for the RNA that can complementarily bind to target-C5.

The following single-stranded oligonucleotides with sticky ends (underlined) were synthesized:

C5F:
(SEQ ID NO: 36)
5'-<u>CTTG</u>TTGCCGTAGGTGCCCGG-3';

C5R:
(SEQ ID NO: 37)
5'-<u>AAAC</u>CCGGGCACCTACGGCAA-3'.

Double-stranded DNA with sticky ends was formed through oligonucleotides annealing process, and inserted between the two BbsI restriction sites in pT7-gRNA plasmid, resulting in a pT7-gRNA plasmid containing the C5 site. The positive plasmid was verified by sequencing. A recombinant plasmid, which was obtained by inserting the DNA fragment as shown in 5'-CTTGTTGCCGTAGGTGCCCGG-3' (SEQ ID NO: 36) in forward direction at the BbsI restriction site of pT7-gRNA plasmid, was positive and designated as pT7-gRNA-C5.

2. In Vitro Transcription of the sgRNA Containing Target Site of TaGASR7

With the T7 promoter for initiate the transcription, sgRNA for the TaGASR7 gene was in vitro transcribed using an mRNA transcription kit (Ambion) into sgRNA-GASR7-C5 (SEQ ID NO: 11), and a PolyA tail was added to the 3'end thereof for increasing the stability of the mRNA.

IV. Editing the TaGASR7 Gene by Co-Transformation of the Cas9 Protein and the In Vitro Transcribed sgRNA into Wheat Protoplasts 1. The Preparation of Protoplasts is Identical to Example 3.

2 Transformation of the Protoplasts 1) 15 μg purified Cas9 protein and 20 μg sgRNA-GASR7-C5 were added into a 2 ml centrifuge tube. 200 μl of the protoplasts (about 4×10⁵ cells) was added and then 250 μl of fresh PEG solution was added and mixed. Transformation was performed in dark for 30 min;

2) 900 μl W5 (room temperature) was added and mixed by reversing, 100 g centrifugation for 3 min, and the supernatant was discarded;

3) 1 ml W5 was added and mixed by reversing, the content was gently transferred to a 6-well plate (with pre-added 1 ml W5), and then cultured at 23° C. overnight.

3. Using PCR/RE Experiments to Analyze the Mutagenesis of Wheat Endogenous Gene TaGASR7 Resulted from Purified Cas9 Protein and the In Vitro Transcribed sgRNA.

48 hours after the transformation of wheat protoplasts, genomic DNA was extracted, which was used as template for PCR/RE (Polymerase Chain Reaction/Restriction digestion) experiment analysis. At the same time, the protoplasts of wild-type wheat variety Bobwhite were used as control. PCR/RE analysis method is based on Shan, Q. et al. Rapid and efficient gene modification in rice and Brachypodium using TALENs. Molecular Plant (2013). Since the target site (positions 248-268 of Genbank No. EU095332) of wheat endogenous gene TaGASR7 (Genbank No. EU095332) contains the recognition sequence (5'-CCSGG-3') of restriction endonuclease NciI, NciI was used in the experiment for conducting the PCR/RE test. Primers used in the PCR amplification were:

TaGASR7-F:
(SEQ ID NO: 38)
5'-GGAGGTGATGGGAGGTGGGGG-3';

TaGASR7-R:
(SEQ ID NO: 39)
5'-CTGGGAGGGCAATTCACATGCCA-3'.

The results of PCR/RE experiments showed that mutations occurred at the target site of TaGASR7 gene. The bands in the figure were recovered and sequenced, and the sequencing results showed that insertion/deletion (indel) occurred at the target site of TaGASR7 gene. (FIGS. 4B and C).

V. Site-Directed Editing of Wheat TaGASR7 Gene Through Particle Bombardment Transformation of Purified Cas9 Protein and In Vitro Transcribed sgRNA 1. Loading Purified Cas9 Protein and In Vitro Transcribed sgRNA to Silica Silica Au-MSN with aperture of 10 nm was used as the carrier. 20 mg of Au-MSN was added to 5 ml phosphate buffer (PBS) of PH 7.4 for sonication. Then 7 mg of purified Cas9 protein was added. The mixture was stirred under 22° C. for 24 hours, centrifuged at 12000 rpm. The supernatant was discarded. Pellet was suspended with PBS buffer. 4 μl of the in vitro transcribed sgRNA (250 ng/μl) was added into 10 μl Cas9 protein-Au-MSN (10 μg/μl) carrier. Then 12.5 μl 2.5M CaCl₂) and 5 μl 0.1M spermidine were added, centrifuged at 5000 rpm for 15 s, discarding the supernatant. The Au-MSN carrying Cas9 protein and coated with mRNA was washed with 100% ethanol twice, and resuspended in 5 μl 100% ethanol, designated sgRNA-Cas9-Au-MSN.

2. Transformation of Wheat Recipient Materials Using Particle Bombardment

1) Immature embryo of the wheat variety Bobwhite was taken and treated for 4 hours using hypertonic medium.

2) A particle bombardment device was used to bombard the wheat immature embryo that was hypertonically cultured in step 1). 5 μl of sgRNA-Cas9-Au-MSN was loaded on the membrane and bombarded; the bombarding distance for each bombardment was 6 cm, the bombarding pressure was 1100 psi, the bombarding diameter was 2 cm.

3) The wheat immature embryo bombarded in step 2) was hypertonically cultured for 16 hours;

4) The wheat immature embryo hypertonically cultured in step 3) were then sequentially subjected to 14 days of callus tissue induction culture, 28 days of differentiation culture, and 14-28 days of rooting culture, so as to obtain wheat plants.

5) DNA was extracted from the wheat seedlings generated in step 4) and mutants with gene knocked-out (site-directed) were detected through PCR/RE tests (for specific test method, please refer to step IV). Wild-type wheat variety Bobwhite was used as control.

The detection results of some mutants indicate that mutations occurred in the target site of wheat TaGASR7 gene. Bands were recovered for sequencing. The sequencing results indicate that insertion/deletion (indel) occurred in the target site of wheat TaGASR7 gene.

Example 5. Site-Directed Editing of Maize
Endogenous ZmIPK Gene by Introducing Purified
Cas9 Protein and sgRNA into Plant Via Pollen
Tube Approach I. Design of the Target Fragment: Target-C2

Target-C2:
                                    SEQ ID NO: 40
5'-CCGAGCTCGACCACGCCGCCGAC-3'; (position 393-415 of the gene ZmIPK as shown in Genbank No.

AY172635).

II. Prokaryotic Expression and Purification of Cas9 Protein
Identical to Example 3, step II.
III. In Vitro Transcription of the sgRNA of the Target Site
1. The Target Site of ZmIPK was Constructed into the pT7-gRNA Vector
C2 is the DNA sequence coding for the RNA that can complementarily bind to target-C2.
The following single-stranded oligonucleotides with sticky ends (underlined) were synthesized:

C2-1F:
                                    (SEQ ID NO: 41)
    5'-AGCAGTCGGCGGCGTGGTCGAGCT-3';

C2-1R:
                                    (SEQ ID NO: 42)
    5'-AAACAGCTCGACCACGCCGCCGAC-3'.

Double-stranded DNA with sticky ends was formed through oligonucleotides annealing process, and inserted between the two BbsI restriction sites in pT7-gRNA plasmid, resulting in a pT7-gRNA plasmid containing the C2 site. The positive plasmid was verified by sequencing. A recombinant plasmid, which was obtained by inserting the DNA fragment as shown in 5'-AGCAGTCGGCGGCGTGGTCGAGCT-3' (SEQ ID NO: 41) in forward direction at the BbsI restriction site of pT7-gRNA plasmid, was positive and designated as pT7-gRNA-C2.

2. In Vitro Transcription of the sgRNA Containing Target Site of ZmIPK

With the T7 promoter for initiate the transcription, sgRNA for the ZmIPK gene was in vitro transcribed using an mRNA transcription kit (Ambion) into sgRNA-IPK-C2 (SEQ ID NO: 12), and a PolyA tail was added to the 3'end thereof for increasing the stability of the mRNA.

IV. Site-Directed Editing of Maize Endogenous ZmIPK Gene by Introducing Purified Cas9 Protein and In Vitro Transcribed sgRNA Via Pollen Tube Approach Strong plants of maize inbred Hill in the field were selected as the recipient materials. The plants were self-fertilized at 14: 00-16:00 of a sunny day. 16-20 hr post pollination, namely 10:00-12:00 of the next day, the styles of the recipients were cut. A mixture of 10 µg/µl Cas9 protein and 250 ng/µl sgRNA was dripped to the incision. The stigmas were bagged until fructifcation. The obtained maize seeds were grown, and genomic DNA was extracted for use in the PCR/RE experiment as a template. Wild type maize variety Hill was set as control in parallel. PCR/RE analysis method is based on Shan, Q. et al. Rapid and efficient gene modification in rice and Brachypodium using TALENs. Molecular Plant (2013). Since the target fragment (positions 393-415 of Genbank No. AY172635) of maize endogenous gene ZmIPK (Genbank No. AY172635) contains the recognition sequence (5'-GAGCTC-3') of restriction endonuclease SacI, the restriction endonuclease SacI was used in the experiment for conducting the PCR/RE test. Primers used in the PCR amplification were:

ZmIPK-1F:
                                    (SEQ ID NO: 43)
    5'- TCGCAGCCCCTGGCAGAGCAA-3';

ZmIPK-1R:
                                    (SEQ ID NO: 44)
    5'- GAGACCTGGGAGAAGGAGACGGATCC-3'.

The results of PCR/RE experiments showed that: mutations occurred at the target site of ZmIPK gene. The uncut bands was recovered and sequenced, and the sequencing results showed that insertion/deletion (indel) occurred at the target site of ZmIPK gene.

Example 6. Site-Directed Editing of NtPVY Gene
by Co-Transformation of a Cas9 Protein Expressed
and Purified in Prokaryotic Expression System and
an In Vitro Transcribed sgRNA into Tobacco
Protoplasts, and the Regeneration into Plants I. Design of the Target Fragment: Target-P4

Target-P4:
                                    (SEQ ID NO: 45)
    5'-TGATACCAGCTGGCTATACACGG-3'

II. Prokaryotic Expression and Purification of Cas9 Protein is Identical to Example 3.
III. In Vitro Transcription of the sgRNA of the Target Site
1. The Target Site of NtPVY was Constructed into the pHSN401 Vector
P4 is the DNA sequence coding for the RNA that can complementarily bind to target-P4.
The following single-stranded oligonucleotides with sticky ends (underlined) were synthesized:

P4-F:
                                    (SEQ ID NO: 46)
    5'-ATTGTGATACCAGCTGGCTATACA-3';

P4-R:
                                    (SEQ ID NO: 47)
    5'-AAACTGTATAGCCAGCTGGTATCA-3 '.

Double-stranded DNA with sticky ends was formed through oligonucleotides annealing process, and inserted between the two BsaI restriction sites in the pHSN401 plasmid, resulting in a pHSN401 plasmid containing P4. The positive plasmid was verified by sequencing. A recombinant plasmid, which was obtained by inserting the DNA fragment as shown in 5'-ATTGTGATACCAGCTGGCTATACA-3' (SEQ ID NO: 46) in forward direction at the BsaI restriction site of pHSN401 plasmid, was positive and designated as p pHSN401-P4.

2. In Vitro Transcription of the sgRNA Containing Target Site of NTPVY

With the T7 promoter for initiate the transcription, sgRNA for the NTPVY gene (SEQ ID NO:13, 14, 15) was in vitro transcribed using an mRNA transcription kit (Ambion) into sgRNA-PVY-P4 (SEQ ID NO:16).

IV. Editing of NtPVY Gene by Co-Transformation of a Cas9 Protein and In Vitro Transcribed sgRNA into Tobacco Protoplasts.

1. Preparation of the Materials

The tobacco variety as used is Honghua Dajinyuan. Seeds were treated with 20% sodium hypochlorite for 20 min, and washed with sterile water for 5 times. Then the seeds were cultured on ½ MS medium under 25° C., 16 h light.

2. Isolation of Protoplasts 1) 6 leaves of 30 day old tobacco plants were selected and cut into sections of about 1 cm under sterile conditions. The sections were placed in a culture plate containing 15 ml enzymolysis solution. The plate was sealed and kept in the dark under 25° C. overnight (most preferable 12 h).

2) After the enzymolysis reaction, a suitable amount of W5 solution was added. The plate was gently shaken to release the protoplasts. Then the protoplast suspension was filtered with 100 μm and 40 μm sterile filter, centrifuged at 70 g for 5 min, discarding the supernatant.

3) The protoplasts were resuspended by adding 5 ml 22% sucrose solution. Then, 2 ml W5 solution was added and centrifuged at 70 g for 5 min. Protoplasts now suspended at the interface.

4) The protoplasts were taken from the interface. 5 ml W5 solution was added and mixed following by 70 g centrifugation for 5 min.

5) The supernatant was discarded. 1 ml MMG transformation solution was added to resuspended the protoplasts. The yield of the protoplasts was determined by microscopy.

3. Transformation and Regeneration of the Protoplasts 1) 20 μg purified Cas9 protein and 20 μg mRNA-PVY-P4 were added into a 14 ml centrifuge tube. 300 μl of the protoplast (about 5×10⁵ cells) was added following by 300 μl of fresh PEG solution, mixed and kept in dark for 20 min.

2) 10 ml W5 was added and mixed, 70 g centrifugation for 3 min, and the supernatant was discarded; this step was repeated.

3) 1 ml of K3:H medium containing 0.6% Sea Plaque agarose (incubated in 40-45° C. water bath before use) was added and mixed. The mixture was transformed into a sterile 30 mm culture plate.

4) After solidification of the medium, the plate was placed in the dark under 24° C. for 24 h, the cultured in dark for another 6 d until the first cell division occurred.

5) The agarose gel was transferred into a 90 mm culture plate, and a suitable amount of liquid A medium was added. Cultivation was continued under 24° C. in dark.

6) 3-4 weeks later, visible callus emerged in the plate. And the callus reached diameters of 8-10 mm after cultivation of 5-6 weeks.

7) The calli were transferred to differentiation medium and cultured for 1-2 weeks until adventitious buds were formed on the surface.

8) Adventitious buds of 3-4 cm were cut and transferred to rooting medium to induce the generation of roots, until the formation of intact plants.

9) The seedlings were transplanted in soil when the roots reach a certain length.

DNA of the transgenic tobacco was extracted and used as the template for PCR/RE (Polymerase Chain Reaction/Restriction digestion) analysis. Wild type tobacco DNA was used as control in parallel. PCR/RE analysis method is based on Shan, Q. et al. Rapid and efficient gene modification in rice and Brachypodium using TALENs. Molecular Plant (2013). Since the target fragment of tobacco endogenous gene NtPVY contains the recognition sequence (5'-CAGCTG-3') of restriction endonuclease PvuII, the restriction endonuclease PvuII was used in the PCR/RE test. Primers used in the PCR amplification were:

```
NtPVY-F:
                                      (SEQ ID NO: 48)
5'-TGGATTAGATGTTTTCAAATGC-3';

NtPVY-R:
                                      (SEQ ID NO: 49)
5'-CATTCTTTTGGGGACGGACAAA-3'.
```

The results of PCR/RE experiments showed that co-transformation of Cas9 protein and in vitro transcribed sgRNA into tobacco protoplasts resulted in mutations in the target site of NtPVY gene. The uncut bands was recovered and sequenced, and the sequencing results showed that insertion/deletion (indel) occurred at the target site of NtPVY gene (FIGS. 5 A and B). In addition, the regenerated transgenic tobacco plants also showed mutation in the target site of NtPVY gene. The sequencing results showed that insertion/deletion (indel) occurred at the target site of NtPVY gene (FIG. 5 C).

Solution for Tobacco protoplast isolation and culture are listed in following Table 6-10.

TABLE 6

50 ml enzymolysis solution

|  | The amount added | Final Concentration |
|---|---|---|
| Cellulase R10 | 0.6 | 1.2% |
| Macerozyme R10 | 0.3 | 0.6% |
| made up to 50 ml with K4 medium, pH adjusted to 5.6 with KOH; centrifugation at 7000 g for 10 min; filtered with a 0.22 μm filter. | | |

TABLE 7

500 ml W5

|  | The amount added | Final Concentration |
|---|---|---|
| NaCl | 4.5 g | 154 mM |
| CaCl₂ | 9.189 g | 125 mM |
| KCl | 0.1864 g | 5 mM |
| Glucose | 0.45 g | 5 mM |
| made up to 500 ml with double distilled water, pH adjusted to 5.8 with KOH, autoclaved. | | |

TABLE 8

10 ml transformation solution

|  | The amount added | Final Concentration |
|---|---|---|
| mannitol (0.8M) | 6.33 ml | 0.5M |
| MgCl₂ (1M) | 0.15 ml | 15 mM |
| MES | 0.01 g | 0.1% |
| made up to 10 ml with double distilled water, pH adjusted to 5.8 with KOH, autoclaved. | | |

TABLE 9

4 ml PEG solution

| | The amount added | Final Concentration |
|---|---|---|
| PEG4000 | 1.6 g | 40% |
| mannitol (0.8M) | 2 ml | 0.4M |
| Ca(NO3)$_2$ | | 0.1M | made up to 4 ml with double distilled water, pH adjusted to 8-9 with KOH, autoclaved.

TABLE 10

Stock solution for Tobacco protoplast isolation and culture

| Medium (ml/L) | A | H | K3 | MS | MS mopho |
|---|---|---|---|---|---|
| 1000 mg/50 ml Stock | | | | | |
| KNO$_3$ | 50.5 | 95 | 125 | 95 | 95 |
| NH$_4$NO$_3$ | | 40 | 30 | 12.5 | 82.5 |
| CaCl$_2$·2H$_2$O | 22 | 30 | 45 | 22 | 36.5 |
| MgSO$_4$·7H$_2$O | 37 | 15 | 12.5 | 18.5 | 18.5 |
| 1000 mg/100 ml | | | | | |
| (NH$_4$)$_2$SO$_4$ | 0 | 0 | 25 | 0 | 0 |
| KH$_2$PO | 0 | 13.6 | 17 | 0 | 17 |
| NaH$_2$PO$_4$ | 0 | 0 | 15 | 0 | 0 |
| (NH4)succinate | 5 | 0 | 0 | 0 | 0 |
| CaHPO$_4$ | 0 | 0 | 0 | 5 | 0 |
| Microelements (MS microelements 10× from Sigma, 100 ml/l) | | | | | |
| | 100 | 100 | 100 | 100 | 100 |
| Carbohydrates (g/l) final concentration | | | | | |
| Sucrose (+) | 30 | 30 | 30 | 20 | 30 |
| D-sorbitol | 0 | 0 | 45.5 | 20 | 0 |
| D-Mannital | 0 | 0 | 45.5 | 20 | 0 |
| Hormones (mg/l final concentration) | | | | | |
| 2,4-D | 0 | 1.5 | 5 | 1.5 | 0 |
| Kinetin | 0 | 0 | 0 | 0 | 0.2 |
| Vitamins (mg/l final concentration) | | | | | |
| PyridoxineHCl | 0.5 | 0.5 | 0.5 | 1.5 | 0.5 |
| Thiamine HCl | 0.1 | 0.1 | 0.1 | 10 | 0.1 |
| Nicotinic acid | 0 | 0.5 | 0.5 | 0.5 | 0.5 |
| Inositol | 100 | 100 | 100 | 100 | 100 |
| Other organics (mg/l final concentration) | | | | | |
| Glycine | 2 | 2 | 2 | 7.5 | 2 |
| L-Glutamine | 0 | 0 | 0 | 877 | 0 |
| L-Asparagine | 0 | 0 | 0 | 266 | 0 |
| Caseinhydrolysate | 400 | 400 | 400 | 0 | 0 |

The invention claimed is:

1. A method for conducting site-directed modification to a target fragment of a target gene in a plant of interest comprising introducing a non-inheritable material into a tissue of the plant of interest by particle bombardment using particles comprising silica and/or gold; wherein said non-inheritable material is a nuclease of a CRISPR associated system specific to said target fragment, wherein the target fragment is cleaved by said nuclease, and wherein a site-directed modification to the target fragment is achieved through a DNA repairing event in the plant;

wherein said tissue is a hypertonically cultured immature or mature embryo; and wherein the non-inheritable material is composed of a mixture of an in vitro transcribed Cas9 mRNA comprising a nuclear localization sequence (NLS) and an in vitro transcribed guide RNA; wherein said guide RNA is an RNA with a palindromic structure which is formed by partial base-pairing between a crRNA and a tracrRNA; said crRNA contains an RNA fragment capable of complementarily binding to the target fragment, wherein the mixture of the Cas9 mRNA and the guide RNA is precipitated on the particles, by combining the Cas9 mRNA, the guide RNA, and the particles with ammonium acetate and isopropanol, incubating the Cas9 mRNA, the guide RNA, and the particles, collecting the particles with bound Cas9 mRNA and guide RNA by centrifugation, resuspending the collected particles with dehydrated ethanol, collecting the washed particles with bound Cas9 mRNA and guide RNA by centrifugation, and resuspending the collected particles in absolute ethanol before adding the collected particles to a membrane of a particle bombardment device, wherein the DNA template is prepared to a concentration of greater than 100 ng/µl and the DNA template is in vitro transcribed to produce the guide RNA, and wherein the guide RNA is present in a concentration of 250 ng/µl.

2. The method of claim 1, wherein the site-directed modification is nucleotide insertion, deletion, and/or replacement in the target fragment.

3. A method for making a transgene-free mutant plant, specifically comprising the following steps:

conducting a site-directed modification to a target fragment of a target gene in a plant of interest according to the method of claim 1, subjecting the modified immature or mature embryo to callus induction culture;

subjecting the induced callus to differentiation culture; and subjecting the differentiated callus to rooting culture, resulting in a plant in which the functions of the target gene are lost or changed and the genome of the plant is free of an integrated exogenous gene.

4. The method of claim 1, wherein the guide RNA is an sgRNA.

5. The method of claim 1, wherein the non-inheritable material is introduced into the tissue, and wherein the tissue is the immature embryo.

6. The method of claim 1, wherein the non-inheritable material is introduced into the tissue, and wherein the tissue is the mature embryo.

7. The method of claim 1, wherein the particle comprises Silica Au-MSN.

* * * * *

SEQUENCE LISTING

<160> NUMBER OF SEQ ID NOS: 102

<210> SEQ ID NO 1
<211> LENGTH: 5860
<212> TYPE: DNA
<213> ORGANISM: Oryza sativa

<400> SEQUENCE: 1

```
atggccacgg cgatcccgca gcggcagctc ttcgtcgccg cgagtggcg cgccccgcg      60
ctcggccgcc gcctccccgt cgtcaacccc gccaccgagt ccccatcgg taccctcctc     120
ttcaccctct ccaccctctg cttctgcctc tgattagcct ttttgttgtt gttgttgttg    180
ctgctgtttt ttgcgtgtcg gtgcgcaggc gagatcccgc cgggcacggc ggaggacgtg    240
gacgcggcgg tggcggcggc gcgggaggcg ctgaagagga accggggccg cgactgggcg    300
cgcgcgccgg gcgccgtccg ggccaagtac ctccgcgcaa tcgcggccaa ggtagggtgg    360
tgactacccc caccccccc cccccccca acgcgacccg cgtgcgtgtg ttccgtacag      420
ggggaggagc tccgcgtggc tctccagtag gttttgagc cccaaatcga tcgatatgct     480
ctagttttaa gtttgctgct taaattcctc aagggtttag tttgcaacca atccttatt     540
ttagcttcg tataagcccc ccatatgatg tgcgtgcgtc ggcatcggaa gtgcgtatcc     600
tctgttctgg actaggaatt ggccataggt tgatcgacag ttcgagtatt ctgcttctgt    660
ttggaataag ttggaagcat ggctgattgt gtatctggat gctgttttg tggtgattcg     720
tttcaagctc ttgttaattg atgggttcaa gcggagaggg tgcgcaacaa caagtgtata    780
tggctcacgg ccatgggtgt gcacatttga ttggtgcgca acaacaagtg tatattgttt    840
gtgtgcttcg ttagttggca ggtcctagtc actaaatcac tattggattg gtactagtta    900
cttttgtgcc ttgacgatgg gactggatta ctagccttt ggttgccttt gtggtattcc     960
```

```
gttgttatgg gcctgttgat ggatggatcc ctttaattc tagtgccaaa tgcatgctag    1020
atttctcaca gtttttctct tcaggttata tttctcgtat ttcctttcc taaaggattg    1080 ctttttcatg tattttctgg catatatagg ttattattat tattattctc cagaacaaga   1140
ttacccatat tatggatcac tagtgtacac ttttttggat gaaaaaccta cttactgaaa   1200
gtaaaacagt gaccagtgca cactttactt gaactgtcaa accatcaatt ttctagcaaa   1260 gcagggatg ctagccttcc agtctaaatg acagtaaact actatacttt tgtccgtagg    1320
tttggaaata tgctaattc tatcataaaa attttcatgg catatgcgag cattttatga    1380
tcaccttttc ccttttctt cagataatcg agaggaaatc tgagctggct agactagaga    1440
cgcttgattg tgggaagcct cttgatgaag cagcatggga catggtatgt ggccagttat   1500
ccactgtatg aatatgtagt tgcctacaca gcaatctttc ctgaacatga atcctgatgt    1560
atgatattcc atttgtcagg acgatgttgc tggatgcttt gagtactttg cagatcttgc    1620 agaatcctg gacaaaaggc aaaatgcacc tgtctctctt ccaatggaaa actttaaatg    1680
ctatcttcgg aaagagccta tcggtgtagt tgggttgatc acaccttggt atttcacatt   1740
tttctctcat cctgcgctta tatttattta tgacccaagc atggtactaa atagtactag    1800
taacatgcat atactgaatg agtttacaac tttacatgat tttttgaac tatgaaagtt    1860 gaagacattt gagattttat tcctcttctc ttgtgcaaac atattattgt ctcacaaatt   1920
gtacctagca gctactctct ccgtttcata ttataagtcg tttgactttt ttcctagtca    1980
aaatgtgtta agtttgacca agtttataga aaaatttagc aacatctaaa atatcaaagt   2040
catgttttag tgttttttca ggctctcatg taagcaattt tgatgtgccc tctccttct    2100 tcttaatata atgatacaca gctcttgtgt attcaaagga aaatatatat atatataatg   2160
atacacacct ctcctccgtg ttaatgcagc tcatttgttc tgtcccggtt caaatatcta    2220 ttttctcat atgttgtcag catgattcac ttaatttagt atatagaaga tgccattatt    2280
tatgtctgga atcttactgc agaagggaaa acaattgata acggaattga ttgcattcta    2340
atttgttgtt tctttgttat gttcttatcg acaattacaa atttgattct gagaatcatg   2400
ttcgggatgt gtatttctac tgcaggaact atcctctcct gatggcaaca tggaaggtag    2460
ctcctgccct ggctgctggc tgtacagctg tactaaaacc atctgaattg gcttccgtgt   2520
aagtttaaca tgttaacttg ttaatgtcat acccatgcta gttgcaatga catttgattt    2580
taaaatgttg tggcatgtcc atgctgcaag caatgtaatt tgaaatctct ctctatcatt   2640
aattaccagg acttgtttgg agcttgctga tgtgtgtaaa gaggttggtc ttccttcagg    2700
tgtgctaaac atagtgactg gattaggttc tgaagccggt gctcctttgt catcacaccc   2760
tggtgtagac aaggtacagc tattcctcct gtaatcatgt atacccatc aatgaaatg     2820 atattcctct caatacatgg tttatgtttt ctgttaggtt gcatttactg ggagttatga   2880
aactggtaaa aagattatgg cttcagctgc tcctatggtt aaggtttgtt tccaaatttc   2940
tgtggatatt ttttgttctc tttctactaa ctctctatta tcaattctca atgttgtcct    3000
tttcttttaa ctcctttact ttttagaatt gtgatcaaga cactttgagc atcattctag    3060
tagccagttc tatcctgttt cttaccttt tatggttcgt cttttcttga cagcctgttt     3120
cactggaact tggtggaaaa agtcctatag tggtgtttga tgatgttgat gttgaaaaag   3180
gtacatgcca cttgctatga ttaactaatt ctgaagtgcg ggactttgta aagcacttaa   3240
ctgagctgga tgctagaccc ccaaaagccc ttttggtgt cttgggcttg ttgcagaaat    3300
actggtccca gacgagcagg atgcaagaaa attaactact tttgccactg attagtattt   3360
```

```
cttagaagtt acacctcaag gattagcaat actttcttaa aatgtgctat tgattaaaaa    3420
gatgtcctgt attattttga gcagatcttg tactggttga tcggcttgca tgaaaatatt    3480
gttgaggatt ataatgccat gccaactgag taaagaaaag agttgtaaaa tatgttatgc    3540
aacatgaata tatatgtgat ttcatttttc cttttctttt tcgtggcaag gaaggcagtt    3600
aggaaggact gatgtgaaaa gcacaagtac tattcttagt tctggaaaac tgtgttcttt    3660
attttcctaa ctacaattca ccttgattag tcagtaactt gatattggca attctagctg    3720
attatgaatt ctgtttatat ttcactaatt ttgaatcttt aattacattt tatggttgaa    3780
atttaacgtt ttgtctggtt atggactctg tttgtattca ctcaatttgg atcttccatt    3840
agatttcatt gttggtcctt cttcttgtac agctgttgag tggactctct ttggttgctt    3900
ttggaccaat ggccagattt gcagtgcaac atcgcgtctt attcttcatg taagcattga    3960
atatatccgt caatcataat ctattgttgt acttgatttt ttttctgatc aactcctgag    4020
ttcagattat tatatgatgc cattactatt gcacagagcg aataaaattg tatttatgca    4080
cagcatgtat tttgagtaat atatgcattg cctattattt aatatataga ttgtagcact    4140
taattttgtg tccatgtctc tatgatgttt attactttat tattgccggc atgaagcaac    4200
tttgaactct atgttgatct tgaactaaaa ttgaaattaa ttggcttatt gctattaatg    4260
atatagcttt cagcttcttg ctcctgacca tgaaagttt gcagaaaaaa atcgctaaag    4320
aatttcaaga aaggatggtt gcatgggcca aaaatattaa ggtgtcagat ccacttgaag    4380
agggttgcag gcttgggccc gttgttagtg aaggacaggt accacatgta aactttttct    4440
aaattcaaaa aagaaatgcc actgatcaat ggtaggtcct tccaagcctt attgctggat    4500
tgttgcactg ttttgtcaat tttgtgtaat atagttctga atgaattagt cggtgtatgc    4560
tcttgctagt tgctagtatg tggtacaggg tcttcctact ttgagcaaat tcgtgttaaa    4620
atgcattgat gaaaaggcca ccttttccgta ggtttatctt gtcataattt aaaccccaat    4680
aaaattttaa tttttgttt tgaccccatg gcactttaat gaaatcactt agccatgagc    4740
ttttgtatat attttcaaag caccagaatg tttagatggt tgttggaaa tcttacacat    4800
cctattgcct tgtgtcagta tgagaagatt aagcaatttg tatctaccgc caaaagccaa    4860
ggtgctacca ttctgactgg tggggttaga cccaaggtaa taatctacta cacggttgta    4920
tataggta cccacatatc attatgaagt agaaataatc ttgtatgttt ttgtcagcat    4980
ctggagaaag gtttctatat tgaacccaca atcattactg atgtcgatac atcaatgcaa    5040
atttggaggg aagaagtttt tggtccagtg ctctgtgtga agaatttag cactgaagaa    5100
gaagccattg aattggccaa cgatactcag tgagtttttt ttttaataca gttcattgtc    5160
ctgttcaatc ttgcagcata tgtatatact ctgtggcata tgaacttatt ctgctactac    5220
tactttgat agttatggtc tggctggtgc tgtgctttcc ggtgaccgcg agcgatgcca    5280
gagattaact gaggtatatc caagtgaagg gggttggcat tgtttgattc atatgacatg    5340
gttgcatcaa gctgatattc aagaatctca tttattactt gcattctatg catctccagt    5400
tcttccctgg actccggtca atgttaatat agtttgtttg ctagtagtat gctactccaa    5460
ttaagttgct cttcacttcc acatcatctg atccatgact ttatatttga ccccttttt    5520
ttgcaaaaga aagggaaata cttaacgaaa atttcctact gcaggagatc gatgccggaa    5580
ttatctgggt gaactgctcg caaccctgct tctgccaagc tccatgggc gggaacaagc    5640
gcagcggctt tggacgcgag ctcggagaag ggtgggtagc acacaacaat ctcactttaa    5700
```

| | |
|---|---|
| aacaccattt cgatcgtctg atgatctcga cctgacatca tgcctttggt attttcattc | 5760 |
| acttttcagg ggcattgaca actacctaag cgtcaagcaa gtgacggagt acgcctccga | 5820 |
| tgagccgtgg ggatggtaca atccccttc caagctgtaa | 5860 |

<210> SEQ ID NO 2
<211> LENGTH: 6021
<212> TYPE: DNA
<213> ORGANISM: Artificial Sequence
<220> FEATURE:
<223> OTHER INFORMATION: TALEN sequence

<400> SEQUENCE: 2

| | |
|---|---|
| atggctccta agaaaaagcg caaagtcggt atccatggcg ttccctctag aatggtggat | 60 |
| ctacgcacgc tcggctacag tcagcagcag caagagaaga tcaaaccgaa ggtgcgttcg | 120 |
| acagtggcgc agcaccacga ggcactggtg ggccatgggt tacacacgc gcacatcgtt | 180 |
| gcgctcagcc aacaccccggc agcgttaggg accgtcgctg tcacgtatca gcacataatc | 240 |
| acggcgttgc cagaggcgac acacgaagac atcgttgggc tcggcaaaca gtggtccggc | 300 |
| gcacgcgccc tggaggcctt gctcacggat gcggggagt tgagaggtcc gccgttacag | 360 |
| ttggacacag gccaacttgt gaagattgca aaacgtggcg gcgtgaccgc aatggaggca | 420 |
| gtgcatgcat cgcgcaatgc actgacgggt gccccctga acctgacccc ggaccaagtg | 480 |
| gtggctatcg ccagcaacaa tggcggcaag caagcgctcg aaacggtgca gcggctgttg | 540 |
| ccggtgctgt gccaggacca tggcctgact ccggaccaag tggtggctat cgccagccac | 600 |
| gatggcggca agcaagcgct cgaaacggtg cagcggctgt tgccggtgct gtgccaggac | 660 |
| catggcctga ccccggacca agtggtggct atcgccagca cggtggcgg caagcaagcg | 720 |
| ctcgaaacgg tgcagcggct gttgccggtg ctgtgccagg accatggcct gaccccggac | 780 |
| caagtggtgg ctatcgccag caacaatggc ggcaagcaag cgctcgaaac ggtgcagcgg | 840 |
| ctgttgccgg tgctgtgcca ggaccatggc ctgaccccgg accaagtggt ggctatcgcc | 900 |
| agcaacaatg gcggcaagca agcgctcgaa acggtgcagc ggctgttgcc ggtgctgtgc | 960 |
| caggaccatg gcctgacccc ggaccaagtg gtggctatcg ccagcaacat ggcggcaag | 1020 |
| caagcgctcg aaacggtgca gcggctgttg ccggtgctgt gccaggacca tggcctgacc | 1080 |
| ccggaccaag tggtggctat cgccagcaac ggtggcggca agcaagcgct cgaaacggtg | 1140 |
| cagcggctgt tgccggtgct gtgccaggac catggcctga ccccggacca agtggtggct | 1200 |
| atcgccagca acaatggcgg caagcaagcg ctcgaaacgg tgcagcggct gttgccggtg | 1260 |
| ctgtgccagg accatggcct gactccggac caagtggtgg ctatcgccag ccacgatggc | 1320 |
| ggcaagcaag cgctcgaaac ggtgcagcgg ctgttgccgg tgctgtgcca ggaccatggc | 1380 |
| ctgaccccgg accaagtggt ggctatcgcc agcaacggtg gcggcaagca agcgctcgaa | 1440 |
| acggtgcagc ggctgttgcc ggtgctgtgc caggaccatg gcctgacccc ggaccaagtg | 1500 |
| gtggctatcg ccagcaacgg tggcggcaag caagcgctcg aaacggtgca gcggctgttg | 1560 |
| ccggtgctgt gccaggacca tggcctgacc ccggaccaag tggtggctat cgccagcaac | 1620 |
| ggtggcggca agcaagcgct cgaaacggtg cagcggctgt tgccggtgct gtgccaggac | 1680 |
| catggcctga ccccggacca agtggtggct atcgccagca caatggcgg caagcaagcg | 1740 |
| ctcgaaacgg tgcagcggct gttgccggtg ctgtgccagg accatggcct gaccccggac | 1800 |
| caagtggtgg ctatcgccag caacattggc ggcaagcaag cgctcgaaac ggtgcagcgg | 1860 |
| ctgttgccgg tgctgtgcca ggaccatggc ctgaccccgg accaagtggt ggctatcgcc | 1920 |

```
agcaacaatg gcggcaagca agcgctcgaa acggtgcagc ggctgttgcc ggtgctgtgc    1980
caggaccatg gcctgacccc ggaccaagtg gtggctatcg ccagcaacgg tggcggcaag    2040
caagcgctcg aaacggtgca gcggctgttg ccggtgctgt gccaggacca tggcctgacc    2100
ccggaccaag tggtggctat cgccagcaac attggcggca agcaagcgct cgaaagcatt    2160
gtggcccagc tgagccggcc tgatccggcg ttggccgcgt tgaccaacga ccacctcgtc    2220
gccttggcct gcctcggcgg acgtcctgcc atggatgcag tgaaaaaggg attgccgcac    2280
gcgccggaat tgatcagaag agtcaatcgc cgtattggcg aacgcacgtc ccatcgcgtt    2340
gccggatccc agctggtgaa gtccgagctg aagaaaaaa agagcgagct gcgccacaag    2400
ctcaagtacg tgccccacga gtacatcgag ctgatcgaga tcgcccgcaa cagcacccaa    2460
gaccgcatcc tggagatgaa agtgatggag ttcttcatga aggtgtacgg ctaccgcggc    2520
aagcacctgg gcggctcccg caagcccgat ggcgccatct acaccgtggg ctcccccatc    2580
gactatggcg tcattgtcga caccaaggcc tactccggcg gctacaactt acccatcggt    2640
caggccgacg agatgcaacg ctacgtgaag gagaaccaga cccgcaataa gcacattaat    2700
cccaacgagt ggtggaaggt gtacccctcc tccgtgaccg agttcaaatt cctgttcgtg    2760
tccggccact tcaagggcaa ttataaggcc caactgaccc gcctgaacca aagaccaac    2820 tgcaacggcg ccgtgctgtc cgtggaggaa ctgctgatcg gcggcgagat gatcaaggct    2880
ggtaccctga ccctggaaga ggtgcgccgc aagttcaaca atggtgaaat caatttcagg    2940
tccggcggcg agagggcag aggaagtctt ctaacatgcg gtgacgtgga ggagaatccc    3000
ggccctagga tggactacaa agaccatgac ggtgattata aagatcatga catcgattac    3060
aaggatgacg atgacaagat ggcccccaag aagaagagga aggtgggcat tcacggggtg    3120
ccggctagaa tggtggatct acgcacgctc ggctacagtc agcagcagca agagaagatc    3180
aaaccgaagg tgcgttcgac agtggcgcag caccacgagg cactggtggg ccatgggttt    3240
acacacgcgc acatcgttgc gctcagccaa cacccggcag cgttagggac cgtcgctgtc    3300
acgtatcagc acataatcac ggcgttgcca gaggcgacac acgaagacat cgttggcgtc    3360
ggcaaacagt ggtccggcgc acgcgccctg gaggccttgc tcacggatgc gggggagttg    3420
agaggtccgc cgttacagtt ggacacaggc caacttgtga agattgcaaa acgtggcggc    3480
gtgaccgcaa tggaggcagt gcatgcatcg cgcaatgcac tgacgggtgc ccccctgaac    3540
ctgaccccgg accaagtggt ggctatcgcc agcaacaatg gcggcaagca agcgctcgaa    3600
acggtgcagc ggctgttgcc ggtgctgtgc caggaccatg gcctgactcc ggaccaagtg    3660
gtggctatcg ccagccacga tggcggcaag caagcgctcg aaacggtgca gcggctgttg    3720
ccggtgctgt gccaggacca tggcctgact ccggaccaag tggtggctat cgccagccac    3780
gatggcggca agcaagcgct cgaaacggtg cagcggctgt gccggtgct gtgccaggac    3840 catggcctga ccccggacca agtggtggct atcgccagca acgtggcgg caagcaagcg    3900 ctcgaaacgg tgcagcggct gttgccggtg ctgtgccagg accatggcct gaccccggac    3960
caagtggtgg ctatcgccag caacggtggc ggcaagcaag cgctcgaaac ggtgcagcgg    4020
ctgttgccgg tgctgtgcca ggaccatggc ctgaccccgg accaagtggt ggctatcgcc    4080
agcaacggtg cggcaagca agcgctcgaa acggtgcagc ggctgttgcc ggtgctgtgc    4140
caggaccatg gcctgacccc ggaccaagtg gtggctatcg ccagcaacgg tggcggcaag    4200
caagcgctcg aaacggtgca gcggctgttg ccggtgctgt gccaggacca tggcctgacc    4260
```

```
ccggaccaag tggtggctat cgccagcaac aatggcggca agcaagcgct cgaaacggtg    4320
cagcggctgt tgccggtgct gtgccaggac catggcctga ccccggacca agtggtggct    4380
atcgccagca acgtggcgg caagcaagcg ctcgaaacgg tgcagcggct gttgccggtg    4440
ctgtgccagg accatggcct gactccggac caagtggtgg ctatcgccag ccacgatggc    4500
ggcaagcaag cgctcgaaac ggtgcagcgg ctgttgccgg tgctgtgcca ggaccatggc    4560
ctgaccccgg accaagtggt ggctatcgcc agccacgatg cggcaagca agcgctcgaa    4620 acggtgcagc ggctgttgcc ggtgctgtgc caggaccatg gcctgacccc ggaccaagtg    4680
gtggctatcg ccagcaacat ggcggcaag caagcgctcg aaacggtgca gcggctgttg    4740
ccggtgctgt gccaggacca tggcctgacc ccggaccaag tggtggctat cgccagcaac    4800
attggcggca agcaagcgct cgaaacggtg cagcggctgt tgccggtgct gtgccaggac    4860
catggcctga ccccggacca agtggtggct atcgccagca caatggcgg caagcaagcg    4920 ctcgaaacgg tgcagcggct gttgccggtg ctgtgccagg accatggcct gaccccggac    4980
caagtggtgg ctatcgccag caacaatggc ggcaagcaag cgctcgaaac ggtgcagcgg    5040
ctgttgccgg tgctgtgcca ggaccatggc ctgaccccgg accaagtggt ggctatcgcc    5100
agcaacattg cggcaagca agcgctcgaa acggtgcagc ggctgttgcc ggtgctgtgc    5160
caggaccatg gcctgacccc ggaccaagtg gtggctatcg ccagcaacgg tggcggcaag    5220
caagcgctcg aaagcattgt ggcccagctg agccggcctg atccggcgtt ggccgcgttg    5280
accaacgacc acctcgtcgc cttggcctgc ctcggcggac gtcctgccat ggatgcagtg    5340
aaaaagggat tgccgcacgc gccggaattg atcagaagag tcaatcgccg tattggcgaa    5400
cgcacgtccc atcgcgttgc cggatctcaa ctagtcaaaa gtgaactgga ggagaagaaa    5460
tctgaacttc gtcataaatt gaaatatgtg cctcatgaat atattgaatt aattgaaatt    5520
gccagaaatt ccactcagga tagaattctt gaaatgaagg taatggaatt ttttatgaaa    5580
gtttatggat atagaggtaa acatttgggt ggatcaagga aaccggacgg agcaatttat    5640
actgtcggat ctcctattga ttacggtgtg atcgtggata ctaaagctta tagcggaggt    5700
tataatctgc caattggcca agcagatgaa atggagcgat atgtcgaaga aaatcaaaca    5760
cgaaacaaac atctcaaccc taatgaatgg tggaaagtct atccatcttc tgtaacggaa    5820
tttaagtttt tatttgtgag tggtcacttt aaaggaaact acaaagctca gcttacacga    5880
ttaaatcata tcactaattg taatggagct gttcttagtg tagaagagct tttaattggt    5940
ggagaaatga ttaaagccgg cacattaacc ttagaggaag tgagacggaa atttaataac    6000
ggcgagataa acttttaata g    6021
```

<210> SEQ ID NO 3
<211> LENGTH: 2954
<212> TYPE: DNA
<213> ORGANISM: Artificial Sequence
<220> FEATURE:
<223> OTHER INFORMATION: mRNA-L-T-OsBADH2

<400> SEQUENCE: 3

```
atggctccta agaaaaagcg caaagtcggt atccatggcg ttccctctag aatggtggat      60
ctacgcacgc tcggctacag tcagcagcag caagagaaga tcaaaccgaa ggtgcgttcg     120
acagtggcgc agcaccacga ggcactggtg ggccatgggt ttacacacgc gcacatcgtt     180
gcgctcagcc aacacccggc agcgttaggg accgtcgctg tcacgtatca gcacataatc     240
acggcgttgc cagaggcgac acacgaagac atcgttggcg tcggcaaaca gtggtccggc     300
```

```
gcacgcgccc tggaggcctt gctcacggat gcggggagt tgagaggtcc gccgttacag    360
ttggacacag gccaacttgt gaagattgca aaacgtggcg gcgtgaccgc aatggaggca    420
gtgcatgcat cgcgcaatgc actgacgggt gccccctga acctgacccc ggaccaagtg    480
gtggctatcg ccagcaacaa tggcggcaag caagcgctcg aaacggtgca gcggctgttg    540
ccggtgctgt gccaggacca tggcctgact ccggaccaag tggtggctat cgccagccac    600 gatgcggca agcaagcgct cgaaacggtg cagcggctgt gccggtgct gtgccaggac    660 catggcctga ccccggacca agtggtggct atcgccagca acggtggcgg caagcaagcg    720
ctcgaaacgg tgcagcggct gttgccggtg ctgtgccagg accatggcct gaccccggac    780
caagtggtgg ctatcgccag caacaatggc ggcaagcaag cgctcgaaac ggtgcagcgg    840
ctgttgccgg tgctgtgcca ggaccatggc ctgaccccgg accaagtggt ggctatcgcc    900
agcaacaatg gcggcaagca agcgctcgaa acggtgcagc ggctgttgcc ggtgctgtgc    960
caggaccatg gcctgacccc ggaccaagtg gtggctatcg ccagcaacat ggcggcaag   1020 caagcgctcg aaacggtgca gcggctgttg ccggtgctgt gccaggacca tggcctgacc   1080
ccggaccaag tggtggctat cgccagcaac ggtggcggca agcaagcgct cgaaacggtg   1140
cagcggctgt tgccggtgct gtgccaggac atggcctga ccccggacca agtggtggct   1200
atcgccagca acaatggcgg caagcaagcg ctcgaaacgg tgcagcggct gttgccggtg   1260
ctgtgccagg accatggcct gactccggac caagtggtgg ctatcgccag ccacgatggc   1320
ggcaagcaag cgctcgaaac ggtgcagcgg ctgttgccgg tgctgtgcca ggaccatggc   1380
ctgaccccgg accaagtggt ggctatcgcc agcaacggtg gcggcaagca agcgctcgaa   1440
acggtgcagc ggctgttgcc ggtgctgtgc caggaccatg gcctgacccc ggaccaagtg   1500
gtggctatcg ccagcaacgg tggcggcaag caagcgctcg aaacggtgca gcggctgttg   1560
ccggtgctgt gccaggacca tggcctgacc ccggaccaag tggtggctat cgccagcaac   1620
ggtggcggca agcaagcgct cgaaacggtg cagcggctgt tgccggtgct gtgccaggac   1680
catggcctga ccccggacca agtggtggct atcgccagca acaatggcgg caagcaagcg   1740
ctcgaaacgg tgcagcggct gttgccggtg ctgtgccagg accatggcct gaccccggac   1800
caagtggtgg ctatcgccag caacattggc ggcaagcaag cgctcgaaac ggtgcagcgg   1860
ctgttgccgg tgctgtgcca ggaccatggc ctgaccccgg accaagtggt ggctatcgcc   1920
agcaacaatg gcggcaagca agcgctcgaa acggtgcagc ggctgttgcc ggtgctgtgc   1980
caggaccatg gcctgacccc ggaccaagtg gtggctatcg ccagcaacgg tggcggcaag   2040
caagcgctcg aaacggtgca gcggctgttg ccggtgctgt gccaggacca tggcctgacc   2100
ccggaccaag tggtggctat cgccagcaac attggcggca agcaagcgct cgaaagcatt   2160
gtggcccagc tgagccggcc tgatccggcg ttggccgcgt tgaccaacga ccacctcgtc   2220
gccttggcct gcctcggcgg acgtcctgcc atggatgcag tgaaaaaggg attgccgcac   2280
gcgccggaat tgatcagaag agtcaatcgc cgtattggcg aacgcacgtc ccatcgcgtt   2340
gccggatccc agctggtgaa gtccgagctg aagaaaaaaa agagcgagct gcgccacaag   2400
ctcaagtacg tgccccacga gtacatcgag ctgatcgaga tcgcccgcaa cagcaccaa   2460 gaccgcatcc tggagatgaa agtgatggag ttcttcatga aggtgtacgg ctaccgcggc   2520
aagcacctgg gcggctcccg caagcccgat ggcgccatct acaccgtggg ctcccccatc   2580
gactatggcg tcattgtcga caccaaggcc tactccggcg gctacaactt acccatcggt   2640
```

```
caggccgacg agatgcaacg ctacgtgaag gagaaccaga cccgcaataa gcacattaat    2700
cccaacgagt ggtggaaggt gtaccccctcc tccgtgaccg agttcaaatt cctgttcgtg    2760
tccggccact tcaagggcaa ttataaggcc caactgaccc gcctgaacca caagaccaac    2820
tgcaacggcg ccgtgctgtc cgtggaggaa ctgctgatcg gcggcgagat gatcaaggct    2880
ggtaccctga ccctggaaga ggtgcgccgc aagttcaaca atggtgaaat caatttcagg    2940
tccggcggcg gtag                                                      2954

<210> SEQ ID NO 4
<211> LENGTH: 2940
<212> TYPE: DNA
<213> ORGANISM: Artificial Sequence
<220> FEATURE:
<223> OTHER INFORMATION: mRNA-R-T-OsBADH2b

<400> SEQUENCE: 4
atgcccaaga agaagaggaa ggtgggcatt cacggggtgc cggctagaat ggtggatcta      60
cgcacgctcg gctacagtca gcagcagcaa gagaagatca aaccgaaggt gcgttcgaca     120
gtggcgcagc accacgaggc actggtgggc catgggttta cacacgcgca catcgttgcg     180
ctcagccaac acccggcagc gttagggacc gtcgctgtcc cgtatcagca cataatcacg     240
gcgttgccag aggcgacaca cgaagacatc gttggcgtcg gcaaacagtg gtccggcgca     300
cgcgccctgg aggccttgct cacgcgatgcg ggggagttga gaggtccgcc gttacagttg     360
gacacaggcc aacttgtgaa gattgcaaaa cgtggcggcg tgaccgcaat ggaggcagtg     420
catgcatcgc gcaatgcact gacgggtgcc cccctgaacc tgaccccgga ccaagtggtg     480
gctatcgcca gcaacaatgg cggcaagcaa gcgctcgaaa cggtgcagcg gctgttgccg     540
gtgctgtgcc aggaccatgg cctgactccg gaccaagtgg tggctatcgc cagccacgat     600
ggcggcaagc aagcgctcga aacggtgcag cggctgttgc cggtgctgtg ccaggaccat     660
ggcctgactc cggaccaagt ggtggctatc gccagccacg atggcggcaa gcaagcgctc     720
gaaacggtgc agcggctgtt gccggtgctg tgccaggacc atggcctgac cccggaccaa     780
gtggtggcta tcgccagcaa cggtggcggc aagcaagcgc tcgaaacggt gcagcggctg     840
ttgccggtgc tgtgccagga ccatggcctg accccggacc aagtggtggc tatcgccagc     900
aacggtggcg gcaagcaagc gctcgaaacg gtgcagcggc tgttgccggt gctgtgccag     960
gaccatggcc tgaccccgga ccaagtggtg gctatcgcca gcaacggtgg cggcaagcaa    1020
gcgctcgaaa cggtgcagcg gctgttgccg gtgctgtgcc aggaccatgg cctgaccccg    1080
gaccaagtgg tggctatcgc cagcaacggt ggcggcaagc aagcgctcga aacggtgcag    1140
cggctgttgc cggtgctgtg ccaggaccat ggcctgaccc cggaccaagt ggtggctatc    1200
gccagcaaca atgcggcaa gcaagcgctc gaaacggtgc agcggctgtt gccggtgctg    1260
tgccaggacc atggcctgac cccggaccaa gtggtggcta tcgccagcaa cggtggcggc    1320
aagcaagcgc tcgaaacggt gcagcggctg ttgccggtgc tgtgccagga ccatggcctg    1380
actccggacc aagtggtggc tatcgccagc cacgatggcg gcaagcaagc gctcgaaacg    1440
gtgcagcggc tgttgccggt gctgtgccag gaccatggcc tgaccccgga ccaagtggtg    1500
gctatcgcca gccacgatgg cggcaagcaa gcgctcgaaa cggtgcagcg gctgttgccg    1560
gtgctgtgcc aggaccatgg cctgaccccg gaccaagtgg tggctatcgc cagcaacatt    1620
ggcggcaagc aagcgctcga aacggtgcag cggctgttgc cggtgctgtg ccaggaccat    1680
ggcctgaccc cggaccaagt ggtggctatc gccagcaaca ttggcggcaa gcaagcgctc    1740
```

```
gaaacggtgc agcggctgtt gccggtgctg tgccaggacc atggcctgac cccggaccaa    1800
gtggtggcta tcgccagcaa caatggcggc aagcaagcgc tcgaaacggt gcagcggctg    1860
ttgccggtgc tgtgccagga ccatggcctg accccggacc aagtggtggc tatcgccagc    1920
aacaatggcg gcaagcaagc gctcgaaacg gtgcagcggc tgttgccggt gctgtgccag    1980
gaccatggcc tgaccccgga ccaagtggtg gctatcgcca gcaacattgg cggcaagcaa    2040
gcgctcgaaa cggtgcagcg gctgttgccg gtgctgtgcc aggaccatgg cctgaccccg    2100
gaccaagtgg tggctatcgc cagcaacggt ggcggcaagc aagcgctcga aagcattgtg    2160
gcccagctga gccggcctga tccggcgttg ccgcgttga ccaacgacca cctcgtcgcc     2220
ttggcctgcc tcggcggacg tcctgccatg gatgcagtga aaagggatt gccgcacgcg     2280 ccggaattga tcagaagagt caatcgccgt attggcgaac gcacgtccca tcgcgttgcc    2340
ggatctcaac tagtcaaaag tgaactggag gagaagaaat ctgaacttcg tcataaattg    2400
aaatatgtgc tcatgaata tattgaatta attgaaattg ccagaaattc cactcaggat     2460
agaattcttg aaatgaaggt aatggaattt tttatgaaag tttatggata tagaggtaaa    2520 catttggggtg atcaaggaa accggacgga gcaatttata ctgtcggatc tcctattgat    2580
tacggtgtga tcgtggatac taaagcttat agcggaggtt ataatctgcc aattggccaa    2640
gcagatgaaa tggagcgata tgtcgaagaa aatcaaacac gaaacaaaca tctcaaccct    2700
aatgaatggt ggaaagtcta tccatcttct gtaacggaat ttaagttttt atttgtgagt    2760
ggtcacttta aaggaaacta caaagctcag cttacacgat taaatcatat cactaattgt    2820
aatggagctg ttcttagtgt agaagagctt ttaattggtg gagaaatgat taaagccggc    2880
acattaacct tagaggaagt gagacggaaa tttaataacg gcgagataaa cttttaatag    2940

<210> SEQ ID NO 5
<211> LENGTH: 2050
<212> TYPE: DNA
<213> ORGANISM: Artificial Sequence
<220> FEATURE:
<223> OTHER INFORMATION: TAL-L encoding sequence

<400> SEQUENCE: 5
atggtggatc tacgcacgct cggctacagt cagcagcagc aagagaagat caaaccgaag      60
gtgcgttcga cagtggcgca gcaccacgag gcactggtgg ccatgggtt tacacacgcg      120 cacatcgttg cgctcagcca acaccccggca gcgttaggga ccgtcgctgt cacgtatcag     180
cacataatca cggcgttgcc agaggcgaca cacgaagaca tcgttggcgt cggcaaacag     240
tggtccggcg cacgcgccct ggaggccttg ctcacggatg cgggggagtt gagaggtccg      300
ccgttacagt tggacacagg ccaacttgtg aagattgcaa acgtggcgg cgtgaccgca       360 atggaggcag tgcatgcatc gcgcaatgca ctgacgggtg ccccctgaa cctgaccccg       420 gaccaagtgg tggctatcgc cagccacgat ggcggcaagc aagcgctcga aacggtgcag      480
cggctgttgc cggtgctgtg ccaggaccat ggcctgaccc cggaccaagt ggtggctatc      540
gccagcaaca atggcggcaa gcaagcgctc gaaacggtgc agcggctgtt gccggtgctg      600
tgccaggacc atggcctgac tccggaccaa gtggtggcta tcgccagcca cgatggcggc      660
aagcaagcgc tcgaaacggt gcagcggctg ttgccggtgc tgtgccagga ccatggcctg      720
accccggacc aagtggtggc tatcgccagc aacggtggcg gcaagcaagc gctcgaaacg      780
gtgcagcggc tgttgccggt gctgtgccag gaccatggcc tgaccccgga ccaagtggtg      840
```

```
gctatcgcca gcaacaatgg cggcaagcaa gcgctcgaaa cggtgcagcg gctgttgccg      900
gtgctgtgcc aggaccatgg cctgactccg gaccaagtgg tggctatcgc cagccacgat      960
ggcggcaagc aagcgctcga acggtgcag cggctgttgc cggtgctgtg ccaggaccat      1020
ggcctgaccc cggaccaagt ggtggctatc gccagcaacg gtggcggcaa gcaagcgctc      1080
gaaacggtgc agcggctgtt gccggtgctg tgccaggacc atggcctgac cccggaccaa      1140
gtggtggcta tcgccagcaa caatggcggc aagcaagcgc tcgaaacggt gcagcggctg      1200
ttgccggtgc tgtgccagga ccatggcctg actccggacc aagtggtggc tatcgccagc      1260
cacgatggcg gcaagcaagc gctcgaaacg gtgcagcggc tgttgccggt gctgtgccag      1320
gaccatggcc tgaccccgga ccaagtggtg gctatcgcca gcaacggtgg cggcaagcaa      1380
gcgctcgaaa cggtgcagcg gctgttgccg gtgctgtgcc aggaccatgg cctgaccccg      1440
gaccaagtgg tggctatcgc cagccacgat ggcggcaagc aagcgctcga acggtgcag      1500
cggctgttgc cggtgctgtg ccaggaccat ggcctgaccc cggaccaagt ggtggctatc      1560
gccagcaaca atggcggcaa gcaagcgctc gaaacggtgc agcggctgtt gccggtgctg      1620
tgccaggacc atggcctgac tccggaccaa gtggtggcta tcgccagcca cgatggcggc      1680
aagcaagcgc tcgaaacggt gcagcggctg ttgccggtgc tgtgccagga ccatggcctg      1740
actccggacc aagtggtggc tatcgccagc cacgatggcg gcaagcaagc gctcgaaacg      1800
gtgcagcggc tgttgccggt gctgtgccag gaccatggcc tgaccccgga ccaagtggtg      1860
gctatcgcca gcaacaatgg cggcaagcaa gcgctcgaaa cggtgcagcg gctgttgccg      1920
gtgctgtgcc aggaccatgg cctgaccccg gaccaagtgg tggctatcgc cagcaacggt      1980
ggcggcaagc aagcgctcga aagcattgtg gcccagctga gccggcctga tccggcgttg      2040
gccgcgttga                                                              2050
```

<210> SEQ ID NO 6
<211> LENGTH: 2152
<212> TYPE: DNA
<213> ORGANISM: Artificial Sequence
<220> FEATURE:
<223> OTHER INFORMATION: TAL-R encoding sequence

<400> SEQUENCE: 6

```
atggtggatc tacgcacgct cggctacagt cagcagcagc aagagaagat caaaccgaag       60
gtgcgttcga cagtggcgca gcaccacgag gcactggtgg ccatgggtt tacacacgcg       120
cacatcgttg cgctcagcca cacccggca gcgttaggga ccgtcgctgt cacgtatcag       180
cacataatca cggcgttgcc agaggcgaca cacgaagaca tcgttggcgt cggcaaacag       240
tggtccggcg cacgcgccct ggaggccttg ctcacggatg cgggggagtt gagaggtccg       300
ccgttacagt tggacacagg ccaacttgtg aagattgcaa acgtggcgg cgtgaccgca       360
atggaggcag tgcatgcatc gcgcaatgca ctgacgggtg ccccctgaa cctgaccccg       420
gaccaagtgg tggctatcgc cagcaacaag ggcggcaagc aagcgctcga acggtgcag       480
cggctgttgc cggtgctgtg ccaggaccat ggcctgaccc cggaccaagt ggtggctatc       540
gccagcaaca agggcggcaa gcaagcgctc gaaacggtgc agcggctgtt gccggtgctg       600
tgccaggacc atggcctgac cccggaccaa gtggtggcta tcgccagcaa caagggcggc       660
aagcaagcgc tcgaaacggt gcagcggctg ttgccggtgc tgtgccagga ccatggcctg       720
accccggacc aagtggtggc tatcgccagc aacattggcg gcaagcaagc gctcgaaacg       780
gtgcagcggc tgttgccggt gctgtgccag gaccatggcc tgaccccgga ccaagtggtg       840
```

-continued

```
gctatcgcca gcaacaaggg cggcaagcaa gcgctcgaaa cggtgcagcg gctgttgccg      900
gtgctgtgcc aggaccatgg cctgaccccg gaccaagtgg tggctatcgc cagcaacatt      960
ggcggcaagc aagcgctcga acggtgcag cggctgttgc cggtgctgtg ccaggaccat      1020
ggcctgaccc cggaccaagt ggtggctatc gccagcaacg gtggcggcaa gcaagcgctc     1080
gaaacggtgc agcggctgtt gccggtgctg tgccaggacc atggcctgac cccggaccaa     1140
gtggtggcta tcgccagcaa caagggcggc aagcaagcgc tcgaaacggt gcagcggctg     1200
ttgccggtgc tgtgccagga ccatggcctg actccggacc aagtggtggc tatcgccagc     1260
cacgatggcg gcaagcaagc gctcgaaacg gtgcagcggc tgttgccggt gctgtgccag     1320
gaccatggcc tgaccccgga ccaagtggtg gctatcgcca gcaacattgg cggcaagcaa     1380
gcgctcgaaa cggtgcagcg gctgttgccg gtgctgtgcc aggaccatgg cctgaccccg     1440
gaccaagtgg tggctatcgc cagcaacggt ggcggcaagc aagcgctcga acggtgcag    1500
cggctgttgc cggtgctgtg ccaggaccat ggcctgaccc cggaccaagt ggtggctatc     1560
gccagcaaca ttggcggcaa gcaagcgctc gaaacggtgc agcggctgtt gccggtgctg     1620
tgccaggacc atggcctgac cccggaccaa gtggtggcta tcgccagcaa cggtggcggc     1680
aagcaagcgc tcgaaacggt gcagcggctg ttgccggtgc tgtgccagga ccatggcctg     1740
actccggacc aagtggtggc tatcgccagc cacgatggcg gcaagcaagc gctcgaaacg     1800
gtgcagcggc tgttgccggt gctgtgccag gaccatggcc tgactccgga ccaagtggtg     1860
gctatcgcca ccacgatgg cggcaagcaa gcgctcgaaa cggtgcagcg gctgttgccg     1920
gtgctgtgcc aggaccatgg cctgactccg gaccaagtgg tggctatcgc cagccacgat     1980
ggcggcaagc aagcgctcga acggtgcag cggctgttgc cggtgctgtg ccaggaccat    2040
ggcctgaccc cggaccaagt ggtggctatc gccagcaaca agggcggcaa gcaagcgctc     2100
gaaagcattg tggcccagct gagccggcct gatccggcgt tggccgcgtt ga            2152
```

<210> SEQ ID NO 7
<211> LENGTH: 683
<212> TYPE: PRT
<213> ORGANISM: Artificial Sequence
<220> FEATURE:
<223> OTHER INFORMATION: TAL-MLO-L

<400> SEQUENCE: 7

```
Met Val Asp Leu Arg Thr Leu Gly Tyr Ser Gln Gln Gln Gln Glu Lys
1               5                   10                  15

Ile Lys Pro Lys Val Arg Ser Thr Val Ala Gln His His Glu Ala Leu
            20                  25                  30

Val Gly His Gly Phe Thr His Ala His Ile Val Ala Leu Ser Gln His
        35                  40                  45

Pro Ala Ala Leu Gly Thr Val Ala Val Thr Tyr Gln His Ile Ile Thr
    50                  55                  60

Ala Leu Pro Glu Ala Thr His Glu Asp Ile Val Gly Val Gly Lys Gln
65                  70                  75                  80

Trp Ser Gly Ala Arg Ala Leu Glu Ala Leu Leu Thr Asp Ala Gly Glu
                85                  90                  95

Leu Arg Gly Pro Pro Leu Gln Leu Asp Thr Gly Gln Leu Val Lys Ile
            100                 105                 110

Ala Lys Arg Gly Gly Val Thr Ala Met Glu Ala Val His Ala Ser Arg
        115                 120                 125
```

-continued

```
Asn Ala Leu Thr Gly Ala Pro Leu Asn Leu Thr Pro Asp Gln Val Val
    130                 135                 140

Ala Ile Ala Ser His Asp Gly Gly Lys Gln Ala Leu Glu Thr Val Gln
145                 150                 155                 160

Arg Leu Leu Pro Val Leu Cys Gln Asp His Gly Leu Thr Pro Asp Gln
                165                 170                 175

Val Val Ala Ile Ala Ser Asn Asn Gly Gly Lys Gln Ala Leu Glu Thr
            180                 185                 190

Val Gln Arg Leu Leu Pro Val Leu Cys Gln Asp His Gly Leu Thr Pro
        195                 200                 205

Asp Gln Val Val Ala Ile Ala Ser His Asp Gly Gly Lys Gln Ala Leu
    210                 215                 220

Glu Thr Val Gln Arg Leu Leu Pro Val Leu Cys Gln Asp His Gly Leu
225                 230                 235                 240

Thr Pro Asp Gln Val Val Ala Ile Ala Ser Asn Gly Gly Lys Gln
                245                 250                 255

Ala Leu Glu Thr Val Gln Arg Leu Leu Pro Val Leu Cys Gln Asp His
                260                 265                 270

Gly Leu Thr Pro Asp Gln Val Val Ala Ile Ala Ser Asn Asn Gly Gly
        275                 280                 285

Lys Gln Ala Leu Glu Thr Val Gln Arg Leu Leu Pro Val Leu Cys Gln
    290                 295                 300

Asp His Gly Leu Thr Pro Asp Gln Val Val Ala Ile Ala Ser His Asp
305                 310                 315                 320

Gly Gly Lys Gln Ala Leu Glu Thr Val Gln Arg Leu Leu Pro Val Leu
                325                 330                 335

Cys Gln Asp His Gly Leu Thr Pro Asp Gln Val Val Ala Ile Ala Ser
            340                 345                 350

Asn Gly Gly Lys Gln Ala Leu Glu Thr Val Gln Arg Leu Leu Pro
        355                 360                 365

Val Leu Cys Gln Asp His Gly Leu Thr Pro Asp Gln Val Val Ala Ile
    370                 375                 380

Ala Ser Asn Asn Gly Gly Lys Gln Ala Leu Glu Thr Val Gln Arg Leu
385                 390                 395                 400

Leu Pro Val Leu Cys Gln Asp His Gly Leu Thr Pro Asp Gln Val Val
                405                 410                 415

Ala Ile Ala Ser His Asp Gly Gly Lys Gln Ala Leu Glu Thr Val Gln
            420                 425                 430

Arg Leu Leu Pro Val Leu Cys Gln Asp His Gly Leu Thr Pro Asp Gln
        435                 440                 445

Val Val Ala Ile Ala Ser Asn Gly Gly Lys Gln Ala Leu Glu Thr
    450                 455                 460

Val Gln Arg Leu Leu Pro Val Leu Cys Gln Asp His Gly Leu Thr Pro
465                 470                 475                 480

Asp Gln Val Val Ala Ile Ala Ser His Asp Gly Gly Lys Gln Ala Leu
                485                 490                 495

Glu Thr Val Gln Arg Leu Leu Pro Val Leu Cys Gln Asp His Gly Leu
            500                 505                 510

Thr Pro Asp Gln Val Val Ala Ile Ala Ser Asn Asn Gly Gly Lys Gln
        515                 520                 525

Ala Leu Glu Thr Val Gln Arg Leu Leu Pro Val Leu Cys Gln Asp His
    530                 535                 540

Gly Leu Thr Pro Asp Gln Val Val Ala Ile Ala Ser His Asp Gly Gly
```

-continued

```
                          545                 550                 555                 560
Lys Gln Ala Leu Glu Thr Val Gln Arg Leu Leu Pro Val Leu Cys Gln
                    565                 570                 575

Asp His Gly Leu Thr Pro Asp Gln Val Val Ala Ile Ala Ser His Asp
                580                 585                 590

Gly Gly Lys Gln Ala Leu Glu Thr Val Gln Arg Leu Leu Pro Val Leu
                595                 600                 605

Cys Gln Asp His Gly Leu Thr Pro Asp Gln Val Val Ala Ile Ala Ser
            610                 615                 620

Asn Asn Gly Gly Lys Gln Ala Leu Glu Thr Val Gln Arg Leu Leu Pro
625                 630                 635                 640

Val Leu Cys Gln Asp His Gly Leu Thr Pro Asp Gln Val Val Ala Ile
                        645                 650                 655

Ala Ser Asn Gly Gly Gly Lys Gln Ala Leu Glu Ser Ile Val Ala Gln
                    660                 665                 670

Leu Ser Arg Pro Asp Pro Ala Leu Ala Ala Leu
                675                 680

<210> SEQ ID NO 8
<211> LENGTH: 717
<212> TYPE: PRT
<213> ORGANISM: Artificial Sequence
<220> FEATURE:
<223> OTHER INFORMATION: TAL-MLO-R

<400> SEQUENCE: 8

Met Val Asp Leu Arg Thr Leu Gly Tyr Ser Gln Gln Gln Gln Glu Lys
1               5                   10                  15

Ile Lys Pro Lys Val Arg Ser Thr Val Ala Gln His His Glu Ala Leu
            20                  25                  30

Val Gly His Gly Phe Thr His Ala His Ile Val Ala Leu Ser Gln His
        35                  40                  45

Pro Ala Ala Leu Gly Thr Val Ala Val Thr Tyr Gln His Ile Ile Thr
    50                  55                  60

Ala Leu Pro Glu Ala Thr His Glu Asp Ile Val Gly Val Gly Lys Gln
65                  70                  75                  80

Trp Ser Gly Ala Arg Ala Leu Glu Ala Leu Leu Thr Asp Ala Gly Glu
                85                  90                  95

Leu Arg Gly Pro Pro Leu Gln Leu Asp Thr Gly Gln Leu Val Lys Ile
            100                 105                 110

Ala Lys Arg Gly Gly Val Thr Ala Met Glu Ala Val His Ala Ser Arg
        115                 120                 125

Asn Ala Leu Thr Gly Ala Pro Leu Asn Leu Thr Pro Asp Gln Val Val
    130                 135                 140

Ala Ile Ala Ser Asn Lys Gly Gly Lys Gln Ala Leu Glu Thr Val Gln
145                 150                 155                 160

Arg Leu Leu Pro Val Leu Cys Gln Asp His Gly Leu Thr Pro Asp Gln
                165                 170                 175

Val Val Ala Ile Ala Ser Asn Lys Gly Gly Lys Gln Ala Leu Glu Thr
            180                 185                 190

Val Gln Arg Leu Leu Pro Val Leu Cys Gln Asp His Gly Leu Thr Pro
        195                 200                 205

Asp Gln Val Val Ala Ile Ala Ser Asn Lys Gly Gly Lys Gln Ala Leu
    210                 215                 220

Glu Thr Val Gln Arg Leu Leu Pro Val Leu Cys Gln Asp His Gly Leu
```

```
                225                 230                 235                 240
Thr Pro Asp Gln Val Val Ala Ile Ala Ser Asn Ile Gly Gly Lys Gln
                    245                 250                 255

Ala Leu Glu Thr Val Gln Arg Leu Leu Pro Val Leu Cys Gln Asp His
                260                 265                 270

Gly Leu Thr Pro Asp Gln Val Val Ala Ile Ala Ser Asn Lys Gly Gly
                275                 280                 285

Lys Gln Ala Leu Glu Thr Val Gln Arg Leu Leu Pro Val Leu Cys Gln
            290                 295                 300

Asp His Gly Leu Thr Pro Asp Gln Val Val Ala Ile Ala Ser Asn Ile
305                 310                 315                 320

Gly Gly Lys Gln Ala Leu Glu Thr Val Gln Arg Leu Leu Pro Val Leu
                325                 330                 335

Cys Gln Asp His Gly Leu Thr Pro Asp Gln Val Val Ala Ile Ala Ser
                340                 345                 350

Asn Gly Gly Gly Lys Gln Ala Leu Glu Thr Val Gln Arg Leu Leu Pro
            355                 360                 365

Val Leu Cys Gln Asp His Gly Leu Thr Pro Asp Gln Val Val Ala Ile
        370                 375                 380

Ala Ser Asn Lys Gly Gly Lys Gln Ala Leu Glu Thr Val Gln Arg Leu
385                 390                 395                 400

Leu Pro Val Leu Cys Gln Asp His Gly Leu Thr Pro Asp Gln Val Val
                405                 410                 415

Ala Ile Ala Ser His Asp Gly Gly Lys Gln Ala Leu Glu Thr Val Gln
                420                 425                 430

Arg Leu Leu Pro Val Leu Cys Gln Asp His Gly Leu Thr Pro Asp Gln
            435                 440                 445

Val Val Ala Ile Ala Ser Asn Ile Gly Gly Lys Gln Ala Leu Glu Thr
        450                 455                 460

Val Gln Arg Leu Leu Pro Val Leu Cys Gln Asp His Gly Leu Thr Pro
465                 470                 475                 480

Asp Gln Val Val Ala Ile Ala Ser Asn Gly Gly Gly Lys Gln Ala Leu
                485                 490                 495

Glu Thr Val Gln Arg Leu Leu Pro Val Leu Cys Gln Asp His Gly Leu
                500                 505                 510

Thr Pro Asp Gln Val Val Ala Ile Ala Ser Asn Ile Gly Gly Lys Gln
            515                 520                 525

Ala Leu Glu Thr Val Gln Arg Leu Leu Pro Val Leu Cys Gln Asp His
        530                 535                 540

Gly Leu Thr Pro Asp Gln Val Val Ala Ile Ala Ser Asn Gly Gly Gly
545                 550                 555                 560

Lys Gln Ala Leu Glu Thr Val Gln Arg Leu Leu Pro Val Leu Cys Gln
                565                 570                 575

Asp His Gly Leu Thr Pro Asp Gln Val Val Ala Ile Ala Ser His Asp
                580                 585                 590

Gly Gly Lys Gln Ala Leu Glu Thr Val Gln Arg Leu Leu Pro Val Leu
            595                 600                 605

Cys Gln Asp His Gly Leu Thr Pro Asp Gln Val Val Ala Ile Ala Ser
        610                 615                 620

His Asp Gly Gly Lys Gln Ala Leu Glu Thr Val Gln Arg Leu Leu Pro
625                 630                 635                 640

Val Leu Cys Gln Asp His Gly Leu Thr Pro Asp Gln Val Val Ala Ile
                645                 650                 655
```

```
Ala Ser His Asp Gly Gly Lys Gln Ala Leu Glu Thr Val Gln Arg Leu
                660                 665                 670

Leu Pro Val Leu Cys Gln Asp His Gly Leu Thr Pro Asp Gln Val Val
        675                 680                 685

Ala Ile Ala Ser Asn Lys Gly Gly Lys Gln Ala Leu Glu Ser Ile Val
    690                 695                 700

Ala Gln Leu Ser Arg Pro Asp Pro Ala Leu Ala Ala Leu
705                 710                 715

<210> SEQ ID NO 9
<211> LENGTH: 4204
<212> TYPE: DNA
<213> ORGANISM: Artificial Sequence
<220> FEATURE:
<223> OTHER INFORMATION: Cas9 gene

<400> SEQUENCE: 9
```

| | | | | | |
|---|---|---|---|---|---|
| atggcccta | agaagaagag | aaaggtcggt | attcacggcg | ttcctgcggc | gatggacaag | 60 |
| aagtatagta | ttggtctgga | cattgggacg | aattccgttg | gctgggccgt | gatcaccgat | 120 |
| gagtacaagg | tccttccaa | gaagtttaag | gttctgggga | acaccgatcg | gcacagcatc | 180 |
| aagaagaatc | tcattggagc | cctcctgttc | gactcaggcg | agaccgccga | agcaacaagg | 240 |
| ctcaagagaa | ccgcaaggag | acggtataca | agaaggaaga | ataggatctg | ctacctgcag | 300 |
| gagattttca | gcaacgaaat | ggcgaaggtg | gacgattcgt | tctttcatag | attggaggag | 360 |
| agtttcctcg | tcgaggaaga | taagaagcac | gagaggcatc | ctatctttgg | caacattgtc | 420 |
| gacgaggttg | cctatcacga | aaagtacccc | acaatctatc | atctgcggaa | gaagcttgtg | 480 |
| gactcgactg | ataaggcgga | ccttagattg | atctacctcg | ctctggcaca | catgattaag | 540 |
| ttcaggggcc | attttctgat | cgaggggggat | cttaacccgg | acaatagcga | tgtggacaag | 600 |
| ttgttcatcc | agctcgtcca | aacctacaat | cagctctttg | aggaaaaccc | aattaatgct | 660 |
| tcaggcgtcg | acgccaaggc | gatcctgtct | gcacgccttt | caaagtctcg | ccggcttgag | 720 |
| aacttgatcg | ctcaactccc | gggcgaaaag | aagaacggct | tgttcgggaa | tctcattgca | 780 |
| ctttcgttgg | ggctcacacc | aaacttcaag | agtaattttg | atctcgctga | ggacgcaaag | 840 |
| ctgcagcttt | ccaaggacac | ttatgacgat | gacctggata | accttttggc | ccaaatcggc | 900 |
| gatcagtacg | cggacttgtt | cctcgccgcg | aagaatttgt | cggacgcgat | cctcctgagt | 960 |
| gatattctcc | gcgtgaacac | cgagattaca | aaggccccgc | tctcggcgag | tatgatcaag | 1020 |
| cgctatgacg | agcaccatca | ggatctgacc | cttttgaagg | ctttggtccg | gcagcaactc | 1080 |
| ccagagaagt | acaaggaaat | cttctttgat | caatccaaga | acggctacgc | tggttatatt | 1140 |
| gacggcgggg | catcgcagga | ggaattctac | aagtttatca | agccaattct | ggagaagatg | 1200 |
| gatggcacag | aggaactcct | ggtgaagctc | aatagggagg | accttttgcg | gaagcaaaga | 1260 |
| actttcgata | acggcagcat | ccctcaccag | attcatctcg | ggagctgca | cgccatcctg | 1320 |
| agaaggcagg | aagacttcta | cccctttctt | aaggataacc | gggagaagat | cgaaaagatt | 1380 |
| ctgacgttca | gaattccgta | ctatgtcgga | ccactcgccc | gggtaattc | cagatttgcg | 1440 |
| tggatgacca | gaaagagcga | ggaaaccatc | acccttggga | acttcgagga | agtggtcgat | 1500 |
| aagggcgctt | ccgcacagag | cttcattgag | cgcatgacaa | attttgacaa | gaacctgcct | 1560 |
| aatgagaagg | tccttcccaa | gcattccctc | ctgtacgagt | atttcactgt | ttataacgaa | 1620 |
| ctcacgaagg | tgaagtatgt | gaccgaggga | atgcgcaagc | ccgccttcct | gagcggcgag | 1680 |

```
caaaagaagg cgatcgtgga cctttgtttt aagaccaatc ggaaggtcac agttaagcag    1740
ctcaaggagg actacttcaa gaagattgaa tgcttcgatt ccgttgagat cagcggcgtg    1800
gaagacaggt ttaacgcgtc actggggact taccacgatc tcctgaagat cattaaggat    1860
aaggacttct tggacaacga ggaaaatgag gatatcctcg aagacattgt cctgactctt    1920
acgttgtttg aggataggga aatgatcgag gaacgcttga agacgtatgc ccatctcttc    1980
gatgacaagg ttatgaagca gctcaagaga agaagataca ccggatgggg aaggctgtcc    2040
cgcaagctta tcaatggcat tagagacaag caatcaggga agacaatcct tgacttttg    2100 aagtctgatg gcttcgcgaa caggaatttt atgcagctga ttcacgatga ctcacttact    2160
ttcaaggagg atatccagaa ggctcaagtg tcgggacaag gtgacagtct gcacgagcat    2220
atcgccaacc ttgcgggatc tcctgcaatc aagaagggta ttctgcagac agtcaaggtt    2280
gtggatgagc ttgtgaaggt catgggacgg cataagcccg agaacatcgt tattgagatg    2340
gccagagaaa atcagaccac acaaaagggt cagaagaact cgagggagcg catgaagcgc    2400
atcgaggaag gcattaagga gctggggagt cagatcctta aggagcaccc ggtggaaaac    2460
acgcagttgc aaaatgagaa gctctatctg tactatctgc aaaatggcag ggatatgtat    2520
gtggaccagg agttggatat taaccgcctc tcggattacg acgtcgatca tatcgttcct    2580
cagtccttcc ttaaggatga cagcattgac aataaggttc tcaccaggtc gacaagaac    2640 cgcgggaagt ccgataatgt gcccagcgag gaagtcgtta agaagatgaa gaactactgg    2700
aggcaacttt tgaatgccaa gttgatcaca gaggaagt ttgataacct cactaaggcc    2760
gagcgcggag gtctcagcga actggacaag gcgggcttca ttaagcggca actggttgag    2820
actagacaga tcacgaagca cgtggcgcag attctcgatt cacgcatgaa cacgaagtac    2880
gatgagaatg acaagctgat ccgggaagtg aaggtcatca ccttgaagtc aaagctcgtt    2940
tctgacttca ggaaggattt ccaattttat aaggtgcgcg agatcaacaa ttatcaccat    3000
gctcatgacg catacctcaa cgctgtggtc ggaacagcat tgattaagaa gtacccgaag    3060
ctcgagtccg aattcgtgta cggtgactat aaggttacg atgtgcgcaa gatgatcgcc    3120
aagtcagagc aggaaattgg caaggccact gcgaagtatt tcttttactc taacattatg    3180 aatttctta agactgagat cacgctggct aatggcgaaa tccggaagag accacttatt    3240
gagaccaacg gcgagacagg ggaaatcgtg tgggacaagg ggagggattt cgccacagtc    3300
cgcaaggttc tctctatgcc tcaagtgaat attgtcaaga agactgaagt ccagacgggc    3360
gggttctcaa aggaatctat tctgcccaag cggaactcgg ataagcttat cgccagaaag    3420
aaggactggg acccgaagaa gtatggaggt ttcgactcac caacggtggc ttactctgtc    3480
ctggttgtgg caaggtgga gaagggaaag tcaaagaagc tcaagtctgt caaggagctc    3540
ctgggtatca ccattatgga gaggtccagc ttcgaaaaga atccgatcga ttttctcgag    3600
gcgaagggat ataaggaagt gaagaaggac ctgatcatta gcttccaaa gtacagtctt    3660 ttcgagttgg aaaacggcag gaagcgcatg ttggcttccg caggagagct ccagaagggt    3720
aacgagcttg ctttgccgtc caagtatgtg aacttcctct atctggcatc ccactacgag    3780
aagctcaagg gcagcccaga ggataacgaa cagaagcaac tgtttgtgga gcaacacaag    3840
cattatcttg acgagatcat tgaacagatt tcggagttca gtaagcgcgt catcctcgcc    3900
gacgcgaatt tggataaggt tctctcagcc tacaacaagc accgggacaa gcctatcaga    3960 gagcaggcg aaaatatcat tcatctcttc accctgacaa accttgggc tcccgctgca    4020 ttcaagtatt ttgacactac gattgatcgg aagagataca cttctacgaa ggaggtgctg    4080
```

-continued

```
gatgcaaccc ttatccacca atcgattact ggcctctacg agacgcggat cgacttgagt    4140
cagctcgggg gggataagag accagcggca accaagaagg caggacaagc gaagaagaag    4200
aagt                                                                 4204
```

<210> SEQ ID NO 10
<211> LENGTH: 1401
<212> TYPE: PRT
<213> ORGANISM: Artificial Sequence
<220> FEATURE:
<223> OTHER INFORMATION: Cas9 protein

<400> SEQUENCE: 10

```
Met Ala Pro Lys Lys Lys Arg Lys Val Gly Ile His Gly Val Pro Ala
1               5                   10                  15

Ala Met Asp Lys Lys Tyr Ser Ile Gly Leu Asp Ile Gly Thr Asn Ser
            20                  25                  30

Val Gly Trp Ala Val Ile Thr Asp Glu Tyr Lys Val Pro Ser Lys Lys
        35                  40                  45

Phe Lys Val Leu Gly Asn Thr Asp Arg His Ser Ile Lys Lys Asn Leu
    50                  55                  60

Ile Gly Ala Leu Leu Phe Asp Ser Gly Glu Thr Ala Glu Ala Thr Arg
65                  70                  75                  80

Leu Lys Arg Thr Ala Arg Arg Arg Tyr Thr Arg Arg Lys Asn Arg Ile
                85                  90                  95

Cys Tyr Leu Gln Glu Ile Phe Ser Asn Glu Met Ala Lys Val Asp Asp
            100                 105                 110

Ser Phe Phe His Arg Leu Glu Glu Ser Phe Leu Val Glu Glu Asp Lys
        115                 120                 125

Lys His Glu Arg His Pro Ile Phe Gly Asn Ile Val Asp Glu Val Ala
    130                 135                 140

Tyr His Glu Lys Tyr Pro Thr Ile Tyr His Leu Arg Lys Lys Leu Val
145                 150                 155                 160

Asp Ser Thr Asp Lys Ala Asp Leu Arg Leu Ile Tyr Leu Ala Leu Ala
                165                 170                 175

His Met Ile Lys Phe Arg Gly His Phe Leu Ile Glu Gly Asp Leu Asn
            180                 185                 190

Pro Asp Asn Ser Asp Val Asp Lys Leu Phe Ile Gln Leu Val Gln Thr
        195                 200                 205

Tyr Asn Gln Leu Phe Glu Glu Asn Pro Ile Asn Ala Ser Gly Val Asp
    210                 215                 220

Ala Lys Ala Ile Leu Ser Ala Arg Leu Ser Lys Ser Arg Arg Leu Glu
225                 230                 235                 240

Asn Leu Ile Ala Gln Leu Pro Gly Glu Lys Lys Asn Gly Leu Phe Gly
                245                 250                 255

Asn Leu Ile Ala Leu Ser Leu Gly Leu Thr Pro Asn Phe Lys Ser Asn
            260                 265                 270

Phe Asp Leu Ala Glu Asp Ala Lys Leu Gln Leu Ser Lys Asp Thr Tyr
        275                 280                 285

Asp Asp Asp Leu Asp Asn Leu Leu Ala Gln Ile Gly Asp Gln Tyr Ala
    290                 295                 300

Asp Leu Phe Leu Ala Ala Lys Asn Leu Ser Asp Ala Ile Leu Leu Ser
305                 310                 315                 320

Asp Ile Leu Arg Val Asn Thr Glu Ile Thr Lys Ala Pro Leu Ser Ala
                325                 330                 335
```

```
Ser Met Ile Lys Arg Tyr Asp Glu His His Gln Asp Leu Thr Leu Leu
            340                 345                 350

Lys Ala Leu Val Arg Gln Gln Leu Pro Glu Lys Tyr Lys Glu Ile Phe
            355                 360                 365

Phe Asp Gln Ser Lys Asn Gly Tyr Ala Gly Tyr Ile Asp Gly Gly Ala
            370                 375                 380

Ser Gln Glu Glu Phe Tyr Lys Phe Ile Lys Pro Ile Leu Glu Lys Met
385                 390                 395                 400

Asp Gly Thr Glu Glu Leu Leu Val Lys Leu Asn Arg Glu Asp Leu Leu
                405                 410                 415

Arg Lys Gln Arg Thr Phe Asp Asn Gly Ser Ile Pro His Gln Ile His
            420                 425                 430

Leu Gly Glu Leu His Ala Ile Leu Arg Arg Gln Glu Asp Phe Tyr Pro
            435                 440                 445

Phe Leu Lys Asp Asn Arg Glu Lys Ile Glu Lys Ile Leu Thr Phe Arg
            450                 455                 460

Ile Pro Tyr Tyr Val Gly Pro Leu Ala Arg Gly Asn Ser Arg Phe Ala
465                 470                 475                 480

Trp Met Thr Arg Lys Ser Glu Glu Thr Ile Thr Pro Trp Asn Phe Glu
                485                 490                 495

Glu Val Val Asp Lys Gly Ala Ser Ala Gln Ser Phe Ile Glu Arg Met
                500                 505                 510

Thr Asn Phe Asp Lys Asn Leu Pro Asn Glu Lys Val Leu Pro Lys His
            515                 520                 525

Ser Leu Leu Tyr Glu Tyr Phe Thr Val Tyr Asn Glu Leu Thr Lys Val
            530                 535                 540

Lys Tyr Val Thr Glu Gly Met Arg Lys Pro Ala Phe Leu Ser Gly Glu
545                 550                 555                 560

Gln Lys Lys Ala Ile Val Asp Leu Leu Phe Lys Thr Asn Arg Lys Val
                565                 570                 575

Thr Val Lys Gln Leu Lys Glu Asp Tyr Phe Lys Lys Ile Glu Cys Phe
            580                 585                 590

Asp Ser Val Glu Ile Ser Gly Val Glu Asp Arg Phe Asn Ala Ser Leu
            595                 600                 605

Gly Thr Tyr His Asp Leu Leu Lys Ile Ile Lys Asp Lys Asp Phe Leu
            610                 615                 620

Asp Asn Glu Glu Asn Glu Asp Ile Leu Glu Asp Ile Val Leu Thr Leu
625                 630                 635                 640

Thr Leu Phe Glu Asp Arg Glu Met Ile Glu Glu Arg Leu Lys Thr Tyr
                645                 650                 655

Ala His Leu Phe Asp Asp Lys Val Met Lys Gln Leu Lys Arg Arg Arg
            660                 665                 670

Tyr Thr Gly Trp Gly Arg Leu Ser Arg Lys Leu Ile Asn Gly Ile Arg
            675                 680                 685

Asp Lys Gln Ser Gly Lys Thr Ile Leu Asp Phe Leu Lys Ser Asp Gly
            690                 695                 700

Phe Ala Asn Arg Asn Phe Met Gln Leu Ile His Asp Asp Ser Leu Thr
705                 710                 715                 720

Phe Lys Glu Asp Ile Gln Lys Ala Gln Val Ser Gly Gln Gly Asp Ser
                725                 730                 735

Leu His Glu His Ile Ala Asn Leu Ala Gly Ser Pro Ala Ile Lys Lys
            740                 745                 750
```

```
Gly Ile Leu Gln Thr Val Lys Val Val Asp Glu Leu Val Lys Val Met
            755                 760                 765
Gly Arg His Lys Pro Glu Asn Ile Val Ile Glu Met Ala Arg Glu Asn
    770                 775                 780
Gln Thr Thr Gln Lys Gly Gln Lys Asn Ser Arg Glu Arg Met Lys Arg
785                 790                 795                 800
Ile Glu Glu Gly Ile Lys Glu Leu Gly Ser Gln Ile Leu Lys Glu His
                805                 810                 815
Pro Val Glu Asn Thr Gln Leu Gln Asn Glu Lys Leu Tyr Leu Tyr Tyr
        820                 825                 830
Leu Gln Asn Gly Arg Asp Met Tyr Val Asp Gln Glu Leu Asp Ile Asn
    835                 840                 845
Arg Leu Ser Asp Tyr Asp Val Asp His Ile Val Pro Gln Ser Phe Leu
850                 855                 860
Lys Asp Asp Ser Ile Asp Asn Lys Val Leu Thr Arg Ser Asp Lys Asn
865                 870                 875                 880
Arg Gly Lys Ser Asp Asn Val Pro Ser Glu Glu Val Val Lys Lys Met
                885                 890                 895
Lys Asn Tyr Trp Arg Gln Leu Leu Asn Ala Lys Leu Ile Thr Gln Arg
        900                 905                 910
Lys Phe Asp Asn Leu Thr Lys Ala Glu Arg Gly Gly Leu Ser Glu Leu
    915                 920                 925
Asp Lys Ala Gly Phe Ile Lys Arg Gln Leu Val Glu Thr Arg Gln Ile
930                 935                 940
Thr Lys His Val Ala Gln Ile Leu Asp Ser Arg Met Asn Thr Lys Tyr
945                 950                 955                 960
Asp Glu Asn Asp Lys Leu Ile Arg Glu Val Lys Val Ile Thr Leu Lys
                965                 970                 975
Ser Lys Leu Val Ser Asp Phe Arg Lys Asp Phe Gln Phe Tyr Lys Val
        980                 985                 990
Arg Glu Ile Asn Asn Tyr His His Ala His Asp Ala Tyr Leu Asn Ala
    995                 1000                1005
Val Val Gly Thr Ala Leu Ile Lys Lys Tyr Pro Lys Leu Glu Ser
    1010                1015                1020
Glu Phe Val Tyr Gly Asp Tyr Lys Val Tyr Asp Val Arg Lys Met
    1025                1030                1035
Ile Ala Lys Ser Glu Gln Glu Ile Gly Lys Ala Thr Ala Lys Tyr
    1040                1045                1050
Phe Phe Tyr Ser Asn Ile Met Asn Phe Phe Lys Thr Glu Ile Thr
    1055                1060                1065
Leu Ala Asn Gly Glu Ile Arg Lys Arg Pro Leu Ile Glu Thr Asn
    1070                1075                1080
Gly Glu Thr Gly Glu Ile Val Trp Asp Lys Gly Arg Asp Phe Ala
    1085                1090                1095
Thr Val Arg Lys Val Leu Ser Met Pro Gln Val Asn Ile Val Lys
    1100                1105                1110
Lys Thr Glu Val Gln Thr Gly Gly Phe Ser Lys Glu Ser Ile Leu
    1115                1120                1125
Pro Lys Arg Asn Ser Asp Lys Leu Ile Ala Arg Lys Lys Asp Trp
    1130                1135                1140
Asp Pro Lys Lys Tyr Gly Gly Phe Asp Ser Pro Thr Val Ala Tyr
    1145                1150                1155
Ser Val Leu Val Val Ala Lys Val Glu Lys Gly Lys Ser Lys Lys
```

```
Leu Lys Ser Val Lys Glu Leu Leu Gly Ile Thr Ile Met Glu Arg
    1175                1180                1185

Ser Ser Phe Glu Lys Asn Pro Ile Asp Phe Leu Glu Ala Lys Gly
    1190                1195                1200

Tyr Lys Glu Val Lys Lys Asp Leu Ile Ile Lys Leu Pro Lys Tyr
    1205                1210                1215

Ser Leu Phe Glu Leu Glu Asn Gly Arg Lys Arg Met Leu Ala Ser
    1220                1225                1230

Ala Gly Glu Leu Gln Lys Gly Asn Glu Leu Ala Leu Pro Ser Lys
    1235                1240                1245

Tyr Val Asn Phe Leu Tyr Leu Ala Ser His Tyr Glu Lys Leu Lys
    1250                1255                1260

Gly Ser Pro Glu Asp Asn Glu Gln Lys Gln Leu Phe Val Glu Gln
    1265                1270                1275

His Lys His Tyr Leu Asp Glu Ile Ile Glu Gln Ile Ser Glu Phe
    1280                1285                1290

Ser Lys Arg Val Ile Leu Ala Asp Ala Asn Leu Asp Lys Val Leu
    1295                1300                1305

Ser Ala Tyr Asn Lys His Arg Asp Lys Pro Ile Arg Glu Gln Ala
    1310                1315                1320

Glu Asn Ile Ile His Leu Phe Thr Leu Thr Asn Leu Gly Ala Pro
    1325                1330                1335

Ala Ala Phe Lys Tyr Phe Asp Thr Thr Ile Asp Arg Lys Arg Tyr
    1340                1345                1350

Thr Ser Thr Lys Glu Val Leu Asp Ala Thr Leu Ile His Gln Ser
    1355                1360                1365

Ile Thr Gly Leu Tyr Glu Thr Arg Ile Asp Leu Ser Gln Leu Gly
    1370                1375                1380

Gly Asp Lys Arg Pro Ala Ala Thr Lys Lys Ala Gly Gln Ala Lys
    1385                1390                1395

Lys Lys Lys
    1400

<210> SEQ ID NO 11
<211> LENGTH: 104
<212> TYPE: RNA
<213> ORGANISM: Artificial Sequence
<220> FEATURE:
<223> OTHER INFORMATION: sgRNA-GASR7-C5

<400> SEQUENCE: 11
cuuguugccg uaggugcccg gguuuuagag cuagaaauag caaguuaaaa uaaggcuagu      60
ccguuaucaa cuugaaaaag uggcaccgag ucggugcuuu uuuu                     104

<210> SEQ ID NO 12
<211> LENGTH: 103
<212> TYPE: RNA
<213> ORGANISM: Artificial Sequence
<220> FEATURE:
<223> OTHER INFORMATION: sgRNA-IPK-C2

<400> SEQUENCE: 12
gucggcggcg uggucgagcu guuuuagagc uagaaauagc aaguuaaaau aaggcuaguc      60
cguuaucaac uugaaaaagu ggcaccgagu cggugcuuuu uuu                       103
```

<210> SEQ ID NO 13
<211> LENGTH: 5100
<212> TYPE: DNA
<213> ORGANISM: Artificial Sequence
<220> FEATURE:
<223> OTHER INFORMATION: NtPVY gene
<220> FEATURE:
<221> NAME/KEY: misc_feature
<222> LOCATION: (4265)..(4292)
<223> OTHER INFORMATION: n is a, c, g, or t

<400> SEQUENCE: 13
atggcagagg aagctgagaa attgcgggta gatgaagtag aagtagtcga cgatggacct 60
gaagaaggag aaattgtgga tgaatctgat gatacggcgt cgtatttggg caaagaaatc 120
aaacctaagc atccattaga gaattcttgg actttttggt ttgataatcc tatggctaaa 180
tctagacaag ctgcttgggg cagttccctt cgcgaacttt acactttttc cactgtcgaa 240
gatttttggg ggtaagttat ttcatattcc ctcggttcca atttaggtta cagtctttcc 300
tttttagtca acttttagtc tccttaaatg atatatttct atatttagta ataatttaat 360
atttatagtg acacaaatgt atcactcatt ttagatgaat tttttttttc ttaaactccg 420
taccaaatca aacactacta atgtaaattg ggacgaagcg agtattatat ttcgtgttaa 480
gctgttgtgt tctttggttg taaataaatc atggggtttt attttactgt tcaagaattt 540
tgtgggtgct gtaggatttt gttgaattat ggttttgaat agctcctgaa tatcttgcct 600
tcatataggg aaaattgggt aaaatcttca attttatgtg acactaattc tgttaaaaaa 660 aacacccttta tatatttcga aataatttaa ctttaaactt ctcattgtac tgttaatgtg 720
atgatttgta gtcacacaaa tgtctatctt gttttaaaaa ttttattttt ccttattaaa 780
ctccatgctc agtcaaataa tgggtctatt ggaaacagtc tctctatcct cacaaggtag 840
gagtaaggtc tgcttacaca ctaccctcct cagaccccac ggtatgggat aatactggtt 900
atcttgttgt tgttgctaag tcaaacaaca ttacataaat tgggacggag ggactatctt 960
gtttgatttt cagcttaagg aacttttgtt tcacaattat cagatttttc ctgtccttgc 1020
attttaagtt aaagcagcaa cgaggggcaa tcttactttg gagtgcccga attggtttga 1080
gcttaaattt atgcaagttg tattagtacc tacattgctt tgttgatgct gttgtaatgt 1140
gtaactgact tttccagttt gttacttaaa aaaaggaatt ttttctctca gttacttacc 1200
aattttagtt ttggttcatg gatcgaacta attacattta actttcaatg aatagatata 1260
tcctctttgg tggttggaag acagatagag aattatctgg tgtaaagtag gaaagtgcaa 1320
atatgaacag agattgagac attttggatg gggtaaagaa ttaccttaga agttctagga 1380
aagtaaaagt taaccttgtt aaaagtccgt tctcttcggt tatattgtcg ggtagttctt 1440
ttgcttcaaa tataagaaca tctgacctgt tagtcaaatg tccatattag caactaaaga 1500
tatgttgcaa acactatttt gagctaataa ggtagtggat aatgctttgg tcttagtttt 1560
ctctcctaag caggatatta tagttactat tttccaagta tcaattacac ttttcttaaa 1620
tgcacatata agagcatggt catgtgtatt tcatataggg ctgtcaaatt tggcccaagc 1680
cccaatgacc tgcccaacac gcccaaggtt gggctgtttg ttgacccgcc catttattga 1740
actcaaccca acttgaccca acccattaaa agttgggctg atttttagcc caaattgatc 1800
catgagtaac tttgccagaa taacttagaa ataattcttt tctgtttgat atgttatata 1860
tggccataag aaaagaaaaa gtcttattta gtattataca attcataaga aaacaacaca 1920
tattaattaa agtttggtaa gagttggacg ggttaggcta tgacccaaat tttagcccat 1980

```
cttgacccaa ccaatctcag cccaagtaat ttttgggcgg atcagtgacc cgcccatttg    2040
acaccataag ttcatacgtg tgacgtctct acgtgcattt gtcttcatat accaagctga    2100
ttattcattt aaaaagataa agatatctgc ttttctattc cttaattagg ctaagattac    2160
actaatctcc cctctagatt gatgagacta aacgtagctg cagaccagta tttcaatgtc    2220
attcttggat ctttatttaa gtcgtccgtt ttgagttagg tggtgatgat ttgaaatttg    2280
tgtctgcctt agatgcatgt tgtgttgctc ggatgggggc gcgggtatcc cataatggtg    2340
cagatctaaa ggtcggattt gtcatcacat aaatttttagg attcgaggat atgaattcaa    2400
ctacggttac gggtgctggg atacaaccaa taaatgtatg ttactacata tataagtata    2460
tatttcgatt aattaaagtt atcaaactaa atctaataat tttttcttat aaaatataaa    2520
cacgtaatcc ggtgtggatt ccacacccat gtcgtgttga tacgggtgcg gcaaagattt    2580
tgaagagtcc gcgcaactta ggatgcatgc accttgtttg gtgagttctt tatcagtcta    2640
atttctcaag gcacttgagt tattgtgcaa cttggactat gtcatgccta ttttgatatt    2700
ctgcatcttg gattagatgt tttcaaatgc tattatcctg ttagcttttg atgaaatcct    2760
tgaaccatgt tgcttaaatt ctgcaaacag tgtttacaat aatatcaacc acccaagcaa    2820
gttagttgtg ggagcagact ttcattgttt taagcataaa attgagccaa agtgggaaga    2880
tcctgtatgt gcgaatggag ggaattggac aatgagcttt agtaagggta aatctgatac    2940
cagctggcta tacacggtat gctgaggata ttttaatcca gttcttaatg ttagggcgca    3000
gtctcgtaaa gttatttttcc cctttgatat tatttcaact cttatttttct catttgggat    3060 tattgtagct gctggcaatg attggacatc aattcgatca tggagaggaa atttgtggag    3120
cagtagttag cgtccgaaat aagggggata aaatagcttt atggaccaag aatgctgcaa    3180
atgaaacagc tcaggtaatt tactttttac caatgaaata gcctatttat attactccct    3240
ttgttccaat ttatgtgatg catttttcttt ttttgtccgt ccccaaaaga atgatatctt    3300
tctatattta ggaacaattt aactttgaac tttcgatttt acctttaatg agacaattta    3360
cagccacaca tctatagctt gttttaccac aagtatcaaa agtcattctt tctttcttaa    3420
actccgtgcc cagtcaaaga gaaaaaatag atcgagggag tgcttttat ttttgacgtc    3480 aatgactagg tttgtcattt tcgtggacca agtgggcaga caattttgtt gtgtgcatat    3540
gtggtgctga tgtttattca agaaatacat catctaaacc atcttgtgat gccatttaac    3600
aataatgcgc aagataacaa gggtgtggcc tagtgatcaa tgaagtgggt tgagaaccat    3660
gaggtctcaa gttcaaatcc caatggaggc aaaaacacta gatgatttct tcctgttttgt    3720 ccaagcttgg tggacagaat tactcggtgc ctctgctggt gggaggtagt aagtaacccg    3780
tggaatagtc gaggtgcgcg caagttggca tggacactag ggttataaaa agaataataa    3840
taataatgat aatgattatg tcagctacta ttagttttga tgtgtgcgtg cgtgtgtgta    3900
tatattagtt tcattcctga cataacttct tttgacaact agaaactgat gtatagtacc    3960
gtatgatgta acattgggga tattagaagt tagagggggac gccatcagat atatataggc    4020
atatagtaca gttgtcaaac ttttagctt ttgatagtga gttactttca tgaaaagctg    4080
gaagccaaaa agaaatatgc taatttgtct gcgataaatt attgtttcat tggcaattga    4140
gttatgtgaa gcttggacaa agagaactta tagagtaaaa gatattgttg aggactggtc    4200
caggtgtagg atgttatttc tgtgaagcag tgatttcgtt gtcaaatagt ctgttgcatt    4260
cctgnnnnnn nnnnnnnnnn nnnnnnnnnn nnttcctgct tgatatgtcg ttactaatta    4320
tttagtgtta ggagattctg gcatcattca gccggttcga aaagtctttg caattcttta    4380
```

```
tcccaaaggt taagtaattt tttttgtgta ccatctggta tctggtactc actggcccca    4440
gtaatcggaa ttcgtgccac gttagggccc cttaaaaggg gaagcgctcc ctatcatata    4500
tttctccatt catagggctc gaacccgaga cctttggtta agggcatagg gaatcccttg    4560
gtggttccaa gggttaagta ttattatata cttgataaaa tacctttttc tgtcaacccc    4620
cttcccgtag ttttttttcct ccaatatata gaggtcgacc gtcgacgttc cccgattccc    4680 cctttttttga tggcctcatt catttgaagt accaggccgt tttagtctaa tttcgcaagt    4740
ggatcccctt ttgcgcgtca ttgaaaatat tgaatccttt cagctgttta acggttcatc    4800 aattttttgct ttaatgctta ttgttagcct ttgtttctat atcgttgtaa ctacacttaa    4860
catcatgctt gtcccatctc ctgaaacttc tctctgcagg ttagcattgg taagcaatgg    4920
aaggagtttc tggattacag caactcgatt ggcttcatat ttcatgtatg acatcttatt    4980
tatggtatgc cttgaaatca gtttctcata atttgctact cataaagaat catcttcttt    5040
tgcaaattgc aggacgactc aatgaggctc ggcagaggtg ccaagaatcg ttatacagta    5100
```

<210> SEQ ID NO 14
<211> LENGTH: 660
<212> TYPE: DNA
<213> ORGANISM: Artificial Sequence
<220> FEATURE:
<223> OTHER INFORMATION: NtPVY conding sequence

<400> SEQUENCE: 14

```
atggcagagg aagctgagaa attgcgggta gatgaagtag aagtagtcga cgatggacct      60
gaagaaggag aaattgtgga tgaatctgat gatacggcgt cgtatttggg caaagaaatc     120
aaacctaagc atccattaga gaattcttgg acttttttggt ttgataatcc tatggctaaa     180
tctagacaag ctgcttgggg cagttcccct cgcgaacttt acacttttttc cactgtcgaa     240 gattttttggg gtgtttacaa taatatcaac cacccaagca agttagttgt gggagcagac     300
tttcattgtt ttaagcataa aattgagcca agtgggaag atcctgtatg tgcgaatgga     360
gggaattgga caatgagctt tagtaagggt aaatctgata ccagctggct atacacgctg     420
ctggcaatga ttggacatca attcgatcat ggagaggaaa tttgtggagc agtagttagc     480
gtccgaaata gggggataa atagctttta tggaccaaga atgctgcaaa tgaaacagct     540
caggttagca ttggtaagca atggaaggag tttctggatt acagcaactc gattggcttc     600
atatttcatg acgactcaat gaggctcggc agaggtgcca agaatcgtta tacagtatag    660
```

<210> SEQ ID NO 15
<211> LENGTH: 219
<212> TYPE: PRT
<213> ORGANISM: Artificial Sequence
<220> FEATURE:
<223> OTHER INFORMATION: NtPVY protein

<400> SEQUENCE: 15

```
Met Ala Glu Glu Ala Glu Lys Leu Arg Val Asp Glu Val Glu Val Val
1               5                   10                  15

Asp Asp Gly Pro Glu Glu Gly Glu Ile Val Asp Glu Ser Asp Asp Thr
            20                  25                  30

Ala Ser Tyr Leu Gly Lys Glu Ile Lys Pro Lys His Pro Leu Glu Asn
        35                  40                  45

Ser Trp Thr Phe Trp Phe Asp Asn Pro Met Ala Lys Ser Arg Gln Ala
    50                  55                  60
```

```
Ala Trp Gly Ser Ser Leu Arg Glu Leu Tyr Thr Phe Ser Thr Val Glu
 65                  70                  75                  80

Asp Phe Trp Gly Val Tyr Asn Asn Ile Asn His Pro Ser Lys Leu Val
                 85                  90                  95

Val Gly Ala Asp Phe His Cys Phe Lys His Lys Ile Glu Pro Lys Trp
            100                 105                 110

Glu Asp Pro Val Cys Ala Asn Gly Gly Asn Trp Thr Met Ser Phe Ser
        115                 120                 125

Lys Gly Lys Ser Asp Thr Ser Trp Leu Tyr Thr Leu Leu Ala Met Ile
    130                 135                 140

Gly His Gln Phe Asp His Gly Glu Glu Ile Cys Gly Ala Val Val Ser
145                 150                 155                 160

Val Arg Asn Lys Gly Asp Lys Ile Ala Leu Trp Thr Lys Asn Ala Ala
                165                 170                 175

Asn Glu Thr Ala Gln Val Ser Ile Gly Lys Gln Trp Lys Glu Phe Leu
            180                 185                 190

Asp Tyr Ser Asn Ser Ile Gly Phe Ile Phe His Asp Asp Ser Met Arg
        195                 200                 205

Leu Gly Arg Gly Ala Lys Asn Arg Tyr Thr Val
    210                 215

<210> SEQ ID NO 16
<211> LENGTH: 105
<212> TYPE: RNA
<213> ORGANISM: Artificial Sequence
<220> FEATURE:
<223> OTHER INFORMATION: sgRNA-PVY-P4

<400> SEQUENCE: 16
gugauaccag cuggcuauac aguuuuagag cuagaaauag caaguuaaaa uaaggcuagu      60
ccguuaucaa cuugaaaaag uggcaccgag ucggugcuuu uuuuu                     105

<210> SEQ ID NO 17
<211> LENGTH: 104
<212> TYPE: RNA
<213> ORGANISM: Artificial Sequence
<220> FEATURE:
<223> OTHER INFORMATION: sgRNA-GW2-C14

<400> SEQUENCE: 17
gcaggauggg guauuucuag guuuuagagc uagaaauagc aaguuaaaau aaggcuaguc      60
cguuaucaac uugaaaaagu ggcaccgagu cggugcuuuu uuuu                      104

<210> SEQ ID NO 18
<211> LENGTH: 23
<212> TYPE: DNA
<213> ORGANISM: Triticum aestivum

<400> SEQUENCE: 18
ccaggatggg gtatttctag agg                                              23

<210> SEQ ID NO 19
<211> LENGTH: 23
<212> TYPE: DNA
<213> ORGANISM: Artificial Sequence
<220> FEATURE:
<223> OTHER INFORMATION: C14F primer

<400> SEQUENCE: 19
cttgcaggat ggggtatttc tag                                              23
```

<210> SEQ ID NO 20
<211> LENGTH: 23
<212> TYPE: DNA
<213> ORGANISM: Artificial Sequence
<220> FEATURE:
<223> OTHER INFORMATION: C14R primer

<400> SEQUENCE: 20
aaacctagaa atacccate ctg                                              23

<210> SEQ ID NO 21
<211> LENGTH: 38
<212> TYPE: DNA
<213> ORGANISM: Artificial Sequence
<220> FEATURE:
<223> OTHER INFORMATION: T7-TaGW2-F

<400> SEQUENCE: 21
taatacgact cactataggc aggatggggt atttctag                             38

<210> SEQ ID NO 22
<211> LENGTH: 21
<212> TYPE: DNA
<213> ORGANISM: Artificial Sequence
<220> FEATURE:
<223> OTHER INFORMATION: gRNA-PCR-R

<400> SEQUENCE: 22
agcaccgact cggtgccact t                                               21

<210> SEQ ID NO 23
<211> LENGTH: 27
<212> TYPE: DNA
<213> ORGANISM: Artificial Sequence
<220> FEATURE:
<223> OTHER INFORMATION: TaGW2-AF

<400> SEQUENCE: 23
ctgccattac tttgtatttt ggtaata                                         27

<210> SEQ ID NO 24
<211> LENGTH: 23
<212> TYPE: DNA
<213> ORGANISM: Artificial Sequence
<220> FEATURE:
<223> OTHER INFORMATION: TaGW2-BF

<400> SEQUENCE: 24
gttcagatgg caatctaaaa gtt                                             23

<210> SEQ ID NO 25
<211> LENGTH: 25
<212> TYPE: DNA
<213> ORGANISM: Artificial Sequence
<220> FEATURE:
<223> OTHER INFORMATION: TaGW2-DF

<400> SEQUENCE: 25
gcatgtactt tgattgtttg cgtga                                           25

<210> SEQ ID NO 26
<211> LENGTH: 23
<212> TYPE: DNA
<213> ORGANISM: Artificial Sequence
<220> FEATURE:

```
<223> OTHER INFORMATION: TaGW2-R

<400> SEQUENCE: 26
tccttcctct cttaccactt ccc                                        23

<210> SEQ ID NO 27
<211> LENGTH: 52
<212> TYPE: DNA
<213> ORGANISM: Oryza sativa

<400> SEQUENCE: 27
gctggatgct ttgagtactt tgcagatctt gcagaatcct tggacaaaag gc         52

<210> SEQ ID NO 28
<211> LENGTH: 26
<212> TYPE: DNA
<213> ORGANISM: Artificial Sequence
<220> FEATURE:
<223> OTHER INFORMATION: OsBADH-F

<400> SEQUENCE: 28
gatcccgcag cggcagctct tcgtcg                                     26

<210> SEQ ID NO 29
<211> LENGTH: 30
<212> TYPE: DNA
<213> ORGANISM: Artificial Sequence
<220> FEATURE:
<223> OTHER INFORMATION: OsBADH2-R

<400> SEQUENCE: 29
gaggaataaa atctcaaatg tcttcaactt                                 30

<210> SEQ ID NO 30
<211> LENGTH: 53
<212> TYPE: DNA
<213> ORGANISM: Triticum aestivum

<400> SEQUENCE: 30
tcgctgctgc tcgccgtcac gcaggaccca atctccggga tatgcatctc cca        53

<210> SEQ ID NO 31
<211> LENGTH: 53
<212> TYPE: DNA
<213> ORGANISM: Triticum aestivum

<400> SEQUENCE: 31
tcgctgctgc tcgccgtgac gcaggacccc atctccggga tatgcatctc cga        53

<210> SEQ ID NO 32
<211> LENGTH: 53
<212> TYPE: DNA
<213> ORGANISM: Triticum aestivum

<400> SEQUENCE: 32
tcgctgctgc tcgccgtgac gcaggaccca atctccggga tatgcatctc cga        53

<210> SEQ ID NO 33
<211> LENGTH: 25
<212> TYPE: DNA
<213> ORGANISM: Artificial Sequence
<220> FEATURE:
<223> OTHER INFORMATION: TaMLO-F

<400> SEQUENCE: 33
```
tcatcgtctc cgtcctcctg gagca                                            25

<210> SEQ ID NO 34
<211> LENGTH: 28
<212> TYPE: DNA
<213> ORGANISM: Artificial Sequence
<220> FEATURE:
<223> OTHER INFORMATION: TaMLO-R

<400> SEQUENCE: 34
tggtattcca aggaggcggt ctctgtct                                         28

<210> SEQ ID NO 35
<211> LENGTH: 21
<212> TYPE: DNA
<213> ORGANISM: Triticum aestivum

<400> SEQUENCE: 35
ccgccgggca cctacggcaa c                                                21

<210> SEQ ID NO 36
<211> LENGTH: 21
<212> TYPE: DNA
<213> ORGANISM: Artificial Sequence
<220> FEATURE:
<223> OTHER INFORMATION: C5F

<400> SEQUENCE: 36
cttgttgccg taggtgcccg g                                                21

<210> SEQ ID NO 37
<211> LENGTH: 21
<212> TYPE: DNA
<213> ORGANISM: Artificial Sequence
<220> FEATURE:
<223> OTHER INFORMATION: C5R

<400> SEQUENCE: 37
aaacccgggc acctacggca a                                                21

<210> SEQ ID NO 38
<211> LENGTH: 21
<212> TYPE: DNA
<213> ORGANISM: Artificial Sequence
<220> FEATURE:
<223> OTHER INFORMATION: TaGASR7-F

<400> SEQUENCE: 38
ggaggtgatg ggaggtgggg g                                                21

<210> SEQ ID NO 39
<211> LENGTH: 23
<212> TYPE: DNA
<213> ORGANISM: Artificial Sequence
<220> FEATURE:
<223> OTHER INFORMATION: TaGASR7-R

<400> SEQUENCE: 39
ctgggagggc aattcacatg cca                                              23

<210> SEQ ID NO 40
<211> LENGTH: 23
<212> TYPE: DNA
<213> ORGANISM: Zea mays

<400> SEQUENCE: 40
ccgagctcga ccacgccgcc gac                                    23

<210> SEQ ID NO 41
<211> LENGTH: 24
<212> TYPE: DNA
<213> ORGANISM: Artificial Sequence
<220> FEATURE:
<223> OTHER INFORMATION: C2-1F

<400> SEQUENCE: 41
agcagtcggc ggcgtggtcg agct                                   24

<210> SEQ ID NO 42
<211> LENGTH: 24
<212> TYPE: DNA
<213> ORGANISM: Artificial Sequence
<220> FEATURE:
<223> OTHER INFORMATION: C2-1R

<400> SEQUENCE: 42
aaacagctcg accacgccgc cgac                                   24

<210> SEQ ID NO 43
<211> LENGTH: 21
<212> TYPE: DNA
<213> ORGANISM: Artificial Sequence
<220> FEATURE:
<223> OTHER INFORMATION: ZmIPK-1F

<400> SEQUENCE: 43
tcgcagcccc tggcagagca a                                      21

<210> SEQ ID NO 44
<211> LENGTH: 26
<212> TYPE: DNA
<213> ORGANISM: Artificial Sequence
<220> FEATURE:
<223> OTHER INFORMATION: ZmIPK-1R

<400> SEQUENCE: 44
gagacctggg agaaggagac ggatcc                                 26

<210> SEQ ID NO 45
<211> LENGTH: 23
<212> TYPE: DNA
<213> ORGANISM: Nicotiana tabacum

<400> SEQUENCE: 45
tgataccagc tggctataca cgg                                    23

<210> SEQ ID NO 46
<211> LENGTH: 24
<212> TYPE: DNA
<213> ORGANISM: Artificial Sequence
<220> FEATURE:
<223> OTHER INFORMATION: P4-F

<400> SEQUENCE: 46
attgtgatac cagctggcta taca                                   24

<210> SEQ ID NO 47
<211> LENGTH: 24
<212> TYPE: DNA
<213> ORGANISM: Artificial Sequence

```
<220> FEATURE:
<223> OTHER INFORMATION: P4-R

<400> SEQUENCE: 47
aaactgtata gccagctggt atca                                          24

<210> SEQ ID NO 48
<211> LENGTH: 22
<212> TYPE: DNA
<213> ORGANISM: Artificial Sequence
<220> FEATURE:
<223> OTHER INFORMATION: NtPVY-F

<400> SEQUENCE: 48
tggattagat gttttcaaat gc                                            22

<210> SEQ ID NO 49
<211> LENGTH: 22
<212> TYPE: DNA
<213> ORGANISM: Artificial Sequence
<220> FEATURE:
<223> OTHER INFORMATION: NtPVY-R

<400> SEQUENCE: 49
cattcttttg gggacggaca aa                                            22

<210> SEQ ID NO 50
<211> LENGTH: 22
<212> TYPE: DNA
<213> ORGANISM: Triticum aestivum

<400> SEQUENCE: 50
caggatgggg catttctaga gg                                            22

<210> SEQ ID NO 51
<211> LENGTH: 22
<212> TYPE: DNA
<213> ORGANISM: Triticum aestivum

<400> SEQUENCE: 51
caggatgggg tatttctaga gg                                            22

<210> SEQ ID NO 52
<211> LENGTH: 22
<212> TYPE: DNA
<213> ORGANISM: Triticum aestivum

<400> SEQUENCE: 52
caggatgggg tatttctaga gg                                            22

<210> SEQ ID NO 53
<211> LENGTH: 21
<212> TYPE: DNA
<213> ORGANISM: Artificial Sequence
<220> FEATURE:
<223> OTHER INFORMATION: T-1 A1 mutated target sequence

<400> SEQUENCE: 53
caggatgggg cattttagag g                                             21

<210> SEQ ID NO 54
<211> LENGTH: 23
<212> TYPE: DNA
<213> ORGANISM: Artificial Sequence
<220> FEATURE:
```

```
<223> OTHER INFORMATION: T-1 A1 mutated target sequence

<400> SEQUENCE: 54
caggatgggg catttcttag agg                                              23

<210> SEQ ID NO 55
<211> LENGTH: 18
<212> TYPE: DNA
<213> ORGANISM: Artificial Sequence
<220> FEATURE:
<223> OTHER INFORMATION: T-1 B1 mutated target sequence

<400> SEQUENCE: 55
caggatgggg tatagagg                                                    18

<210> SEQ ID NO 56
<211> LENGTH: 134
<212> TYPE: DNA
<213> ORGANISM: Artificial Sequence
<220> FEATURE:
<223> OTHER INFORMATION: T-1 B1 mutated target sequence
<220> FEATURE:
<221> NAME/KEY: misc_feature
<222> LOCATION: (17)..(128)
<223> OTHER INFORMATION: n is a, c, g, or t

<400> SEQUENCE: 56
caggatgggg tatttcnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnta gagg                                                       134

<210> SEQ ID NO 57
<211> LENGTH: 23
<212> TYPE: DNA
<213> ORGANISM: Artificial Sequence
<220> FEATURE:
<223> OTHER INFORMATION: T-1 D1 mutated target sequence+

<400> SEQUENCE: 57
caggatgggg tatttcttag agg                                              23

<210> SEQ ID NO 58
<211> LENGTH: 23
<212> TYPE: DNA
<213> ORGANISM: Artificial Sequence
<220> FEATURE:
<223> OTHER INFORMATION: T-3 B1 mutated target sequence

<400> SEQUENCE: 58
caggatgggg tatttcttag agg                                              23

<210> SEQ ID NO 59
<211> LENGTH: 23
<212> TYPE: DNA
<213> ORGANISM: Artificial Sequence
<220> FEATURE:
<223> OTHER INFORMATION: T-3 D1 mutated target sequence

<400> SEQUENCE: 59
caggatgggg tatttcctag agg                                              23

<210> SEQ ID NO 60
<211> LENGTH: 13
<212> TYPE: DNA
<213> ORGANISM: Artificial Sequence
```

```
<220> FEATURE:
<223> OTHER INFORMATION: T-4 A1 mutated target sequence

<400> SEQUENCE: 60
caggatgggg agg                                                      13

<210> SEQ ID NO 61
<211> LENGTH: 17
<212> TYPE: DNA
<213> ORGANISM: Artificial Sequence
<220> FEATURE:
<223> OTHER INFORMATION: T-4 A1 mutated target sequence

<400> SEQUENCE: 61
caggatgggg ctagagg                                                  17

<210> SEQ ID NO 62
<211> LENGTH: 15
<212> TYPE: DNA
<213> ORGANISM: Artificial Sequence
<220> FEATURE:
<223> OTHER INFORMATION: T-4 B1 mutated target sequence

<400> SEQUENCE: 62
caggatgggt agagg                                                    15

<210> SEQ ID NO 63
<211> LENGTH: 23
<212> TYPE: DNA
<213> ORGANISM: Artificial Sequence
<220> FEATURE:
<223> OTHER INFORMATION: T-4 D1 mutated target sequence

<400> SEQUENCE: 63
caggatgggg tatttcatag agg                                           23

<210> SEQ ID NO 64
<211> LENGTH: 20
<212> TYPE: DNA
<213> ORGANISM: Artificial Sequence
<220> FEATURE:
<223> OTHER INFORMATION: T-4 D1 mutated target sequence

<400> SEQUENCE: 64
caggatgggg tatttcgagg                                               20

<210> SEQ ID NO 65
<211> LENGTH: 23
<212> TYPE: DNA
<213> ORGANISM: Artificial Sequence
<220> FEATURE:
<223> OTHER INFORMATION: T-5 B1 mutated target sequence

<400> SEQUENCE: 65
caggatgggg tatttcgtag agg                                           23

<210> SEQ ID NO 66
<211> LENGTH: 19
<212> TYPE: DNA
<213> ORGANISM: Artificial Sequence
<220> FEATURE:
<223> OTHER INFORMATION: T-5 B1 mutated target sequence

<400> SEQUENCE: 66
caggatgggg tattagagg                                                19
```

```
<210> SEQ ID NO 67
<211> LENGTH: 19
<212> TYPE: DNA
<213> ORGANISM: Artificial Sequence
<220> FEATURE:
<223> OTHER INFORMATION: T-5 D1 mutated target sequence

<400> SEQUENCE: 67
caggatgggg tattagagg                                                   19

<210> SEQ ID NO 68
<211> LENGTH: 23
<212> TYPE: DNA
<213> ORGANISM: Artificial Sequence
<220> FEATURE:
<223> OTHER INFORMATION: T-7 B1 mutated target sequence

<400> SEQUENCE: 68
caggatgggg tatttcctag agg                                              23

<210> SEQ ID NO 69
<211> LENGTH: 23
<212> TYPE: DNA
<213> ORGANISM: Artificial Sequence
<220> FEATURE:
<223> OTHER INFORMATION: T-7 D1 mutated target sequence

<400> SEQUENCE: 69
caggatgggg tatttcttag agg                                              23

<210> SEQ ID NO 70
<211> LENGTH: 11
<212> TYPE: DNA
<213> ORGANISM: Artificial Sequence
<220> FEATURE:
<223> OTHER INFORMATION: T-7 D1 mutated target sequence

<400> SEQUENCE: 70
caggatgggg t                                                           11

<210> SEQ ID NO 71
<211> LENGTH: 23
<212> TYPE: DNA
<213> ORGANISM: Artificial Sequence
<220> FEATURE:
<223> OTHER INFORMATION: T-8 B1 mutated target sequence

<400> SEQUENCE: 71
caggatgggg tatttcctag agg                                              23

<210> SEQ ID NO 72
<211> LENGTH: 23
<212> TYPE: DNA
<213> ORGANISM: Artificial Sequence
<220> FEATURE:
<223> OTHER INFORMATION: T-8 D1 mutated target sequence

<400> SEQUENCE: 72
caggatgggg tatttcttag agg                                              23

<210> SEQ ID NO 73
<211> LENGTH: 11
<212> TYPE: DNA
<213> ORGANISM: Artificial Sequence
<220> FEATURE:
<223> OTHER INFORMATION: T-8 D1 mutated target sequence
```

<400> SEQUENCE: 73
caggatgggg t                                                                       11

<210> SEQ ID NO 74
<211> LENGTH: 54
<212> TYPE: DNA
<213> ORGANISM: Oryza sativa

<400> SEQUENCE: 74
tgctggatgc tttgagtact ttgcagatct tgcagaatcc ttggacaaaa ggca         54

<210> SEQ ID NO 75
<211> LENGTH: 49
<212> TYPE: DNA
<213> ORGANISM: Artificial Sequence
<220> FEATURE:
<223> OTHER INFORMATION: mRNA-T-OsBADH2b mutated sequence

<400> SEQUENCE: 75
tgctggatgc tttgagtact ttgcttgcag aatccttgga caaaaggca               49

<210> SEQ ID NO 76
<211> LENGTH: 54
<212> TYPE: DNA
<213> ORGANISM: Artificial Sequence
<220> FEATURE:
<223> OTHER INFORMATION: mRNA-T-OsBADH2b mutated sequence

<400> SEQUENCE: 76
tgctggatgc tttgagtact ttgcaggtct tgcagaatcc ttggacaaaa ggca         54

<210> SEQ ID NO 77
<211> LENGTH: 54
<212> TYPE: DNA
<213> ORGANISM: Artificial Sequence
<220> FEATURE:
<223> OTHER INFORMATION: mRNA-T-OsBADH2b mutated sequence

<400> SEQUENCE: 77
tgctggatgc tttgagtact ttgccgatct tgcagaatcc ttggacaaaa ggca         54

<210> SEQ ID NO 78
<211> LENGTH: 54
<212> TYPE: DNA
<213> ORGANISM: Artificial Sequence
<220> FEATURE:
<223> OTHER INFORMATION: mRNA-T-OsBADH2b mutated sequence

<400> SEQUENCE: 78
tgctggatgc tttgagtact ttgcagttct tgcagaatcc ttggacaaaa ggca         54

<210> SEQ ID NO 79
<211> LENGTH: 54
<212> TYPE: DNA
<213> ORGANISM: Artificial Sequence
<220> FEATURE:
<223> OTHER INFORMATION: mRNA-T-OsBADH2b mutated sequence

<400> SEQUENCE: 79
tgctggatgc tttgagtact ttgcagatcc tgcagaatcc ttggacaaaa ggca         54

<210> SEQ ID NO 80
<211> LENGTH: 53
<212> TYPE: DNA

<213> ORGANISM: Triticum aestivum

<400> SEQUENCE: 80
tcgctgctgc tcgccgtgac gcaggacccc atctccggga tatgcatctc cga         53

<210> SEQ ID NO 81
<211> LENGTH: 53
<212> TYPE: DNA
<213> ORGANISM: Artificial Sequence
<220> FEATURE:
<223> OTHER INFORMATION: TaML02 mutated sequence

<400> SEQUENCE: 81
tcgctgctgc tcgccgtcac gcaggaccca atctccggga tatgcatctc cca         53

<210> SEQ ID NO 82
<211> LENGTH: 50
<212> TYPE: DNA
<213> ORGANISM: Artificial Sequence
<220> FEATURE:
<223> OTHER INFORMATION: TaML02 mutated sequence

<400> SEQUENCE: 82
tcgctgctgc tcgccgtcac gcaggaaatc tccgggatat gcatctccca            50

<210> SEQ ID NO 83
<211> LENGTH: 49
<212> TYPE: DNA
<213> ORGANISM: Artificial Sequence
<220> FEATURE:
<223> OTHER INFORMATION: TaML02 mutated sequence

<400> SEQUENCE: 83
tcgctgctgc tcgccgtcac gcaggaatct ccgggatatg catctccca             49

<210> SEQ ID NO 84
<211> LENGTH: 44
<212> TYPE: DNA
<213> ORGANISM: Artificial Sequence
<220> FEATURE:
<223> OTHER INFORMATION: TaML02 mutated sequence

<400> SEQUENCE: 84
tcgctggtgc tccccgtcac gatctccggg atatgcatct ccca                  44

<210> SEQ ID NO 85
<211> LENGTH: 46
<212> TYPE: DNA
<213> ORGANISM: Artificial Sequence
<220> FEATURE:
<223> OTHER INFORMATION: TaML02 mutated sequence

<400> SEQUENCE: 85
tcgctgctgc tcgccgtcac gcaatctccg gtctatgcat ctccca                46

<210> SEQ ID NO 86

<400> SEQUENCE: 86

000

<210> SEQ ID NO 87
<211> LENGTH: 136
<212> TYPE: DNA
<213> ORGANISM: Artificial Sequence
<220> FEATURE:

```
<223> OTHER INFORMATION: TaML02 mutated sequence
<220> FEATURE:
<221> NAME/KEY: misc_feature
<222> LOCATION: (27)..(117)
<223> OTHER INFORMATION: n is a, c, g, or t

<400> SEQUENCE: 87
tcgctgctgc tcgccgtgac gcaggannnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnccg     120
ggatatgcat ctccga                                                     136

<210> SEQ ID NO 88
<211> LENGTH: 38
<212> TYPE: DNA
<213> ORGANISM: Triticum aestivum

<400> SEQUENCE: 88
cctctgcgtg ccgccgggca cctacggcaa caagggcg                              38

<210> SEQ ID NO 89
<211> LENGTH: 37
<212> TYPE: DNA
<213> ORGANISM: Artificial Sequence
<220> FEATURE:
<223> OTHER INFORMATION: TaGASR7 mutated sequence

<400> SEQUENCE: 89
cctctgcgtg ccgccggcac ctacggcaac aagggcg                               37

<210> SEQ ID NO 90
<211> LENGTH: 39
<212> TYPE: DNA
<213> ORGANISM: Artificial Sequence
<220> FEATURE:
<223> OTHER INFORMATION: TaGASR7 mutated sequence

<400> SEQUENCE: 90
cctctgcgtg ccgccgtggc acctacggca acaagggcg                             39

<210> SEQ ID NO 91
<211> LENGTH: 71
<212> TYPE: DNA
<213> ORGANISM: Artificial Sequence
<220> FEATURE:
<223> OTHER INFORMATION: TaGASR7 mutated sequence
<220> FEATURE:
<221> NAME/KEY: misc_feature
<222> LOCATION: (17)..(49)
<223> OTHER INFORMATION: n is a, c, g, or t

<400> SEQUENCE: 91
cctctgcgtg ccgccgnnnn nnnnnnnnnn nnnnnnnnnn nnnnnnnnng gcacctacgg       60
caacaagggc g                                                           71

<210> SEQ ID NO 92
<211> LENGTH: 102
<212> TYPE: DNA
<213> ORGANISM: Artificial Sequence
<220> FEATURE:
<223> OTHER INFORMATION: TaGASR7 mutated sequence
<220> FEATURE:
<221> NAME/KEY: misc_feature
<222> LOCATION: (17)..(80)
<223> OTHER INFORMATION: n is a, c, g, or t

<400> SEQUENCE: 92
```

```
cctctgcgtg ccgccgnnnn nnnnnnnnnn nnnnnnnnnn nnnnnnnnnn nnnnnnnnnn      60
nnnnnnnnnn nnnnnnnnnn ggcacctacg gcaacaaggg cg                         102
```

<210> SEQ ID NO 93
<211> LENGTH: 100
<212> TYPE: DNA
<213> ORGANISM: Artificial Sequence
<220> FEATURE:
<223> OTHER INFORMATION: TaGASR7 mutated sequence
<220> FEATURE:
<221> NAME/KEY: misc_feature
<222> LOCATION: (17)..(78)
<223> OTHER INFORMATION: n is a, c, g, or t

<400> SEQUENCE: 93

```
cctctgcgtg ccgccgnnnn nnnnnnnnnn nnnnnnnnnn nnnnnnnnnn nnnnnnnnnn      60
nnnnnnnnnn nnnnnnnngg cacctacggc aacaagggcg                            100
```

<210> SEQ ID NO 94
<211> LENGTH: 30
<212> TYPE: DNA
<213> ORGANISM: Artificial Sequence
<220> FEATURE:
<223> OTHER INFORMATION: TaGASR7 mutated sequence

<400> SEQUENCE: 94

```
cctctgcgtg ccgccgcggc aacaagggcg                                       30
```

<210> SEQ ID NO 95
<211> LENGTH: 23
<212> TYPE: DNA
<213> ORGANISM: Artificial Sequence
<220> FEATURE:
<223> OTHER INFORMATION: NtPVY sgRNA target site

<400> SEQUENCE: 95

```
tgataccagc tggctataca cgg                                              23
```

<210> SEQ ID NO 96
<211> LENGTH: 54
<212> TYPE: DNA
<213> ORGANISM: Nicotiana tabacum

<400> SEQUENCE: 96

```
agtaagggta atctgatac cagctggcta tacacggtat gctgaggata tttt             54
```

<210> SEQ ID NO 97
<211> LENGTH: 24
<212> TYPE: DNA
<213> ORGANISM: Artificial Sequence
<220> FEATURE:
<223> OTHER INFORMATION: NtPVY target site mutation

<400> SEQUENCE: 97

```
agtaagggtt gctgaggata tttt                                             24
```

<210> SEQ ID NO 98
<211> LENGTH: 48
<212> TYPE: DNA
<213> ORGANISM: Artificial Sequence
<220> FEATURE:
<223> OTHER INFORMATION: NtPVY target site mutation

<400> SEQUENCE: 98

```
agtaaggta aatctgatac cagctacacg gtatgctgag gatatttt        48

<210> SEQ ID NO 99
<211> LENGTH: 55
<212> TYPE: DNA
<213> ORGANISM: Nicotiana tabacum

<400> SEQUENCE: 99
tagtaagggt aaatctgata ccagctggct atacacggta tgctgaggat atttt        55

<210> SEQ ID NO 100
<211> LENGTH: 26
<212> TYPE: DNA
<213> ORGANISM: Artificial Sequence
<220> FEATURE:
<223> OTHER INFORMATION: PVY4 mutated sequences

<400> SEQUENCE: 100
tagtaacggt atgctgagga tatttt        26

<210> SEQ ID NO 101
<211> LENGTH: 47
<212> TYPE: DNA
<213> ORGANISM: Artificial Sequence
<220> FEATURE:
<223> OTHER INFORMATION: PVY4 mutated sequence

<400> SEQUENCE: 101
tagtaagggt aaatctgata ccatacacgg tatgctgagg atatttt        47

<210> SEQ ID NO 102
<211> LENGTH: 48
<212> TYPE: DNA
<213> ORGANISM: Artificial Sequence
<220> FEATURE:
<223> OTHER INFORMATION: PVY4 mutated sequence

<400> SEQUENCE: 102
tagtaagggt aaatctgata ccagctcacg gtatgctgag gatatttt        48
```